(12) United States Patent
Lv et al.

(10) Patent No.: US 12,016,286 B2
(45) Date of Patent: Jun. 25, 2024

(54) WHEAT CENH3 ALLELES

(71) Applicant: Syngenta Crop Protection AG, Basel (CH)

(72) Inventors: Jian Lv, Beijing (CN); Kun Yu, Beijing (CN); Juan Wei, Beijing (CN); Chunxia Liu, Beijing (CN); Hongju Zhou, Beijing (CN); Timothy Joseph Kelliher, RTP, NC (US)

(73) Assignee: Syngenta Crop Protection AG, Basel (CH)

( * ) Notice: Subject to any disclaimer, the term of this patent is extended or adjusted under 35 U.S.C. 154(b) by 223 days.

(21) Appl. No.: 17/286,950

(22) PCT Filed: Oct. 10, 2019

(86) PCT No.: PCT/CN2019/110404
§ 371 (c)(1),
(2) Date: Apr. 20, 2021

(87) PCT Pub. No.: WO2020/073963
PCT Pub. Date: Apr. 16, 2020

(65) Prior Publication Data
US 2021/0378192 A1 Dec. 9, 2021

(30) Foreign Application Priority Data

Oct. 12, 2018 (WO) ................ PCT/CN2018/110063

(51) Int. Cl.
*A01H 6/46* (2018.01)
*A01H 5/10* (2018.01)

(52) U.S. Cl.
CPC .................................. *A01H 6/4678* (2018.05)

(58) Field of Classification Search
None
See application file for complete search history.

(56) References Cited

FOREIGN PATENT DOCUMENTS

| RU | 2551781 C2 | 5/2015 | | |
|---|---|---|---|---|
| WO | 2009088313 A2 | 6/2009 | | |
| WO | 2016138021 A1 | 9/2016 | | |
| WO | WO-2016138021 A1 * | 9/2016 | ............... | A01H 1/02 |
| WO | 2017058022 A1 | 4/2017 | | |
| WO | WO-2017058022 A1 * | 4/2017 | ............... | A01H 1/08 |

OTHER PUBLICATIONS

Miao, Jin, et al. "Targeted mutagenesis in rice using CRISPR-Cas system." Cell research 23.10 (2013): 1233-1236. (Year: 2013).*
Yuan, Jing, et al. "Characterization of two CENH 3 genes and their roles in wheat evolution." New Phytologist 206.2 (2015): 839-851. (Year: 2015).*
Pauwels, Laurens, et al. "A dual sgRNA approach for functional genomics in *Arabidopsis thaliana*." G3: Genes, Genomes, Genetics 8.8 (2018): 2603-2615. (Year: 2018).*
Ceccherini, Isabella, et al., Strategies for the Identification of Intron-Exon Boundaries and Point Mutations: The Example of the RET Proto-Oncogene, Ethods: A Companion to Methods in Enzymology 9, 98-105 (1996) Article No. 0013.
Muiruri, Kariuki S., et al., "Expressed Centromere Specific Histone 3 (CENH3) Variants in Cultivated Triploid and Wild Diploid Bananas (*Musa* spp.)", Front. Plant Sci., Jun. 29, 2017 Sec. Plant Biotechnology vol. 8—2017 |https://doi.org/10.3389/fpls.2017.01034.
Xue, Chenxiao, et al., Manipulating mRNA splicing by base editing in plants', Sci China Life Sci 61, https://doi.org/10.1007/s11427-018-9392-7, received Sep. 14, 2018; accepted Sep. 20, 2018; published online Sep. 27, 2018.
Brown, John W.S., et al., "*Aradidopsis* intron mutations and pre-mRNA splicing", The Plant Journal, 1996, 10(5), pp. 771-780.
Oneil, J. Patrick, et al., "Mutations that alter RNA splicing of the human HPRT gene: a review of the spectrum" Mutation Research 411, 1998, pp. 179-214.
Li, Chaokun, et al. "CRISPR/Cas9-mediated editing of GABRR2 gene in RGC-5 cells induces random exon deletion, exon splicing and new exon recruitment", Biochemical Engineering Journal (2018), https://doi.org/10.1016/j.bej.2018.08.005.
Mou, Haiwei, et al. "CRISPR/Cas9-mediated genome editing induces exon skipping by alternative splicing or exon deletion", Mou et al. Genome Biology (2017) 18:108 DOI 10.1186/s13059-017-1237-8.
Sharpe, Joshua J., et al., "Unexpected consequences: exon skipping caused by CRISPR-generated mutations", Sharpe and Cooper Genome Biology (2017) 18:109 DOI 10.1186/s13059-017-1240-0.
Gapinske, Michael, et al., "CRISPR-SKIP: programmable gene splicing with single base editors", Genome Biology (2018) 19:107 https://doi.org/10.1186/s13059-018-1482-5.
Eckardt, Nancy A., "The Plant Cell Reviews Alternative Splicing", The Plant Cell, vol. 25: 3639, Oct. 2013, www.plantcell.org.
Staiger, Dorothee, et al., et al., "Alternative Splicing at the Intersection of Biological Timing, Development, and Stress Responses", The Plant Cell, vol. 25: 3640-3656, Oct. 2013, www.plantcell.org.
Reddy, Anireddy S., et al., "Complexity of the Alternative Splicing Landscape in Plants", The Plant Cell, vol. 25: 3657-3683, Oct. 2013, www.plantcell.org.
International Search Report dated Jan. 16, 2020, mailed in International Application No. PCT/CN2019/110404.
Duan Minxiao et al. Progress of CENHJ-mediated Haploid Induction Technology Molecular Plant Breeding Aug. 25, 2017(Aug. 25, 2017) No. 10 VaLIS ISSN: 1672-416X sec pp. 4127-4131.

(Continued)

*Primary Examiner* — Weihua Fan
(74) *Attorney, Agent, or Firm* — Christopher Leming

(57) ABSTRACT

The present invention relates to wheat plants comprising a mutation causing an alteration of the amino acid sequence in centromere histone H3 (CENH3), which have the biological activity of a haploid inducer. Further, the present invention provides methods of generating the wheat plants of the present invention and haploid and doubled haploid wheat plants obtainable by crossing the wheat plants of the present invention with wildtype wheat plants.

11 Claims, 1 Drawing Sheet
Specification includes a Sequence Listing.

(56) References Cited

OTHER PUBLICATIONS

Ravi, M et al. Haploid plants produced by centromere-mediated genome elimination Nature Mar. 25, 2010 (Mar. 25, 2010) No. 7288 vol. 464 ISSN:0028-0836 see pp. 615-618.

E.V. Evtushenko et al., "Conserved Molecular Structure of the Centromeric Histone CENH3 in Secale and its Phylogenetic Relationships", www.nature.com/scientificreports, May 31, 2017, pp. 1-10.

Pauwels, Laurens et al.: "A Dual sgRNA Approach for Functional Genomics in *Arabidopsis thaliana*", G3 Genesigenomesigenetics, vol. 8, No. 8, Jun. 8, 2018 (Jun. 8, 2018), pp. 2603-2615, XP055922111, DOI: 10.1534/g3.118.200046 Retrieved from the Internet: URL:http://academic.oup.com/g3journal/article-pdf/8/8/2603/37126009/g3journal2603.pdf.

Extended ESR for EP19870975.0, mailed on Jun. 2, 2022.

* cited by examiner

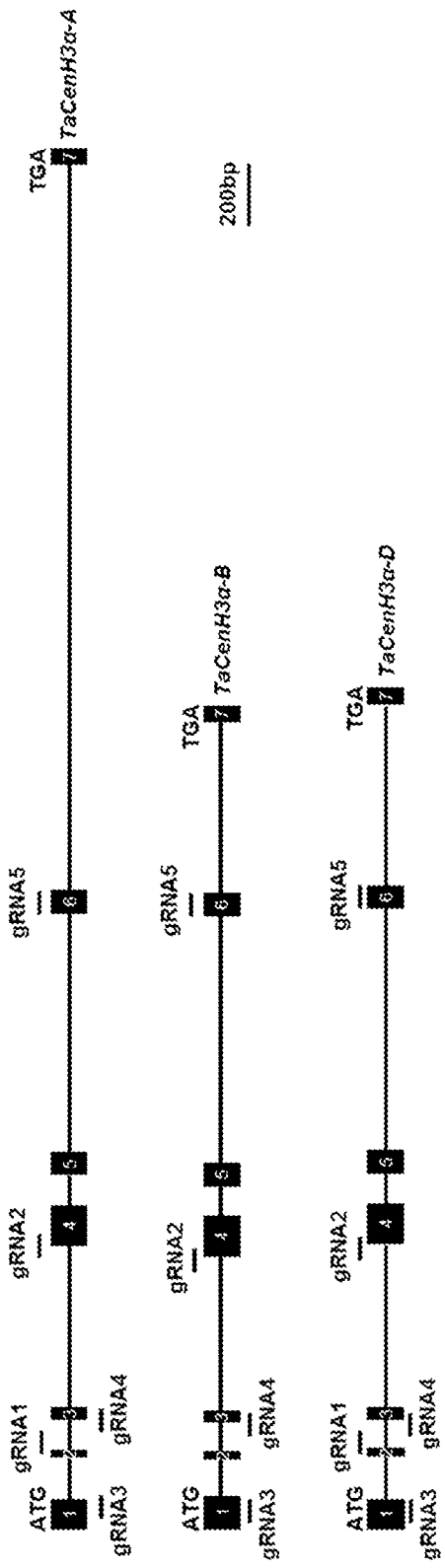

WHEAT CENH3 ALLELES

RELATED APPLICATION INFORMATION

This application is a 371 of International Application No. PCT/CN2019/110404, filed Oct. 10, 2019, which claims priority to CN Application No. 201980063899.2, filed Oct. 12, 2018, the contents of which are incorporated herein by reference herein.

STATEMENT REGARDING ELECTRONIC SUBMISSION OF A SEQUENCE LISTING

A Sequence Listing in ASCII text format, submitted under 37 C.F.R. § 1.821, entitled "81696WOPCT_ST25.txt", 128 kilobytes in size, generated on Oct. 1, 2019 and filed via EFS-Web is provided in lieu of a paper copy. This Sequence Listing is hereby incorporated by reference into the specification for its disclosures.

FIELD OF THE INVENTION

The disclosure relates to the field of agriculture. In particular, the disclosure relates to CenH3 proteins and polynucleotides encoding them, methods for the production of haploid as well as subsequent doubled haploid plants, and plants and seeds derived thereof, particularly in wheat species.

CLAIM FOR PRIORITY

This application claims priority under the Paris Convention to PCT/CN2018/110063, filed Oct. 12, 2018, which is incorporated herein in its entirety.

SEQUENCE LISTING

This application is accompanied by a sequence listing entitled 81696WOPCT_ST25.txt, created Sep. 30, 2019, which is approximately 112 kilobytes in size. This sequence listing is incorporated herein by reference in its entirety. This sequence listing is submitted herewith via EFS-Web, and is in compliance with 37 C.F.R. § 1.824(a)(2)-(6) and (b).

BACKGROUND

A high degree of heterozygosity in breeding material can make plant breeding and selection for beneficial traits a very time consuming process. Extensive population screening, even with the latest molecular breeding tools, is both laborious and costly. The creation of haploid plants followed by chemical or spontaneous genome doubling has proven to be an efficient way to solve the problem of high heterozygosity and accelerate the breeding process. Such technology is also referred to as doubled haploid production system. The use of the doubled haploid production system has allowed breeders to achieve homozygosity at all loci in a single generation via whole-genome duplication. This effectively obviates the need for selfing or backcrossing, where normally at least 7 generations of selfing or backcrossing would be needed to reduce the heterozygosity to an acceptable level.

Haploid plants can be generated according to different methodologies. For instance, haploid plants can be produced in some crops by using a method referred to as microspore culture. However, this method is costly, time-consuming, and does not work in all crops. In some crop species, (doubled) haploid plants can be obtained by parthenogenesis of the egg cell or by elimination of one of the parental genomes. However, such methods are not optimal as they only work in few selected crop species and yield rather low rates of (doubled) haploid plants.

WO2011/044132 discloses a method for producing haploid plants consisting of inactivating or altering or knocking out the centromere-specific H3 (CenH3) protein in a plant. In a first step, the method consists of eliminating or knocking down the endogenous CenH3 gene in plant. In a second step, an expression cassette encoding a mutated or altered CenH3 protein is introduced in the plant. The mutated or altered CenH3 protein is generated by fusing an, optionally GFP-tagged, H3.3 N-terminal domain to the endogenous CenH3 histone-fold domain. Such methodology is also known as "GFP-tailswap" or "tailswap" (also reviewed in Britt and Kuppu, Front Plant Sci. 2016; 7: 357). The crossing of the plant harboring such tailswap with a wildtype plant (i.e., having functional endogenous CenH3 protein without a tailswap), causes uniparental genome elimination, which in turn results in the production of a haploid plant. Some haploid induction, though less frequent, was also found with N-terminal addition of GFP to endogenous CenH3 (no tailswap). However, this methodology is not ideal as it laborious, time-consuming and requires generating a transgenic plant.

WO2014/110274 describes a method for producing haploid plants consisting of crossing a first plant expressing an endogenous CenH3 gene to a second plant referred to as a haploid inducer plant having a genome from at least two species, w % herein a majority of the genome is from a first species and the genome comprises a heterologous genomic region from a second species, wherein the heterologous genomic region encodes a CenH3 polypeptide different from the CenH3 of the first species (also described in Maheshwari et al, PLoS Genet. 2015 Jan. 26; 11(1):e1004970)). However, this methodology is not optimal as it suffers from the same pitfall as above—it is laborious, time-consuming and requires generating a transgenic plant. Further, the method is associated with low yield of haploid plants.

Other methods consist of introducing one or more point mutations leading to single amino acid change in the C-terminal histone fold domain of CenH3 protein or CenH3 gene coding the CenH3 protein. Examples of such mutations in the C-terminal histone fold domain of the CenH3 protein were reported in Karimi-Ashtiyani et al (2015) Proc Natl Acad Sci USA. 2015 Sep. 8; 112(36):11211-16; Kuppu, et al. (2015) PLoS Genet. 2015 Sep. 9; 11(9):e1005494. However, the success of such methods is mitigated as some, as not all of these mutations were found to be sufficient to induce uniparental genome elimination after crossing with a wildtype plant to produce a haploid plant.

Wheat (*Triticum aestivum*) is a particularly complex organism for editing or mutating its genes, as it is a hexaploid organism. Evolved over thousands of years and several cross-breedings with ancestor wheat species, *Triticum aestivum* comprises three genomes: A (possibly from *T. monoccum* or Einkorn wheat), B (possibly from *T. searsii*), and D (possibly from *T. tauschii*). Each genome has 7 chromosomes. *Triticum aestivum* has two copies of each genome, i.e. AA BB DD: thus it has 42 chromosomes total (6 complete genomes each with 7 chromosomes). See generally *The Evolution of Wheat* at www.cerealsdb.uk.net/cerealgenomics/WheatBP/Documents/DOC_Evolution.php, last accessed 10 Jul. 2019. Furthermore, an edit or mutation in one copy of one gene may not present observable effects in *Triticum aestivum*, as the additional 5 copies likely would compensate for the mutant copy. In order to truly observe a knockout mutation's effect, one would have to mutate all 6 copies.

Therefore, it remains elusive which mutation(s) or modification(s) in the CenH3 protein or CenH3 gene coding for the CenH3 protein are capable or sufficient to induce uniparental genome elimination to produce haploid plants. Thus, there remains a need in the art for alternative or improved methods that allow efficient generation of haploid plants (e.g. less labor-intensive, less-time consuming, less expensive, and/or do not necessarily require making a transgenic plant), which can subsequently be doubled to produce doubled haploid plants. With doubled haploid production systems, homozygosity may be achieved in one generation.

SUMMARY

To meet this need, one embodiment of the invention is a wheat plant comprising at least an A genome, a B genome, and a D genome, wherein the B genome comprises a knock-out mutation in a CENH3 gene, and optionally wherein the D genome comprises a knock-out mutation in a CENH3 gene, and further wherein the A genome comprises a mutated CENH3 gene comprising at least one knock-down mutation at a 5' splice site of an intron. In one aspect, the knock-down mutation is a restored frame shift mutation or a large deletion mutation. In another embodiment, the wheat plant is homozygous for a knock-out mutation in a CENH3 gene in the B genome. In an alternate embodiment, the wheat plant is biallelic for a knock-out mutation in a CENH3 gene in the B genome. In another embodiment, the wheat plant is homozygous for a knock-out mutation in a CENH3 gene in the D genome. In an alternate embodiment, the wheat plant is biallelic for a knock-out mutation in a CENH3 gene in the D genome. In yet another embodiment, the wheat plant is homozygous, biallelic, or a combination thereof for a knock-out mutation in a CENH3 gene in the B genome and the D genome. In another embodiment, the wheat plant is homozygous for the restored frame shift CENH3 mutation; or it is heterozygous for the restored frame shift CENH3 mutation; or it is biallelic for the restored frame shift CENH3 mutation.

Another aspect of the invention is a method of generating a haploid-inducing wheat plant, the method comprising: (a) obtaining at least a wheat plant cell comprising at least three genomes: (b) mutating two of the three genomes to obtain homozygous knock-out mutations in a CENH3 gene: (c) mutating the third genome to obtain a homozygous knock-down mutation in a CENH3 gene; and (d) generating a wheat plant therefrom comprising homozygous knock-out mutations in a CENH3 gene of two of the three genomes and further comprising a homozygous knock-down mutation in a CENH3 gene of the third genome; whereby the wheat plant generated from step (d) produces haploid progeny when crossed with a wildtype wheat plant. In one embodiment, the three genomes comprise an A genome, a B genome, and a D genome. In another, the knock-out mutations in a CENH3 gene occur in the B and D genomes. In yet another, the knock-down mutation in a CENH3 gene occurs in the A genome. In one aspect, the knock-down mutations in a CENH3 gene in the A genome are restored frame shift mutations. In another aspect, the restored frame shift mutations are selected from the group consisting of SEQ ID NO: 56, a nucleic acid sequence 70% identical to SEQ ID NO: 56, SEQ ID NO: 63, a nucleic acid sequence 70% identical to SEQ ID NO: 63, SEQ ID NO: 69, and a nucleic acid sequence 70% identical to SEQ ID NO: 69.

Another aspect of the invention is a wheat plant comprising a mutated CENH3 gene comprising at least one deletion mutation in the N-terminal domain resulting in a frame shift, a restored frame shift, or a large deletion. Yet another aspect is a wheat plant comprising a mutated CENH3 gene comprising at least one insertion mutation in the N-terminal domain resulting in a frame shift, a restored frame shift, or a large deletion.

Another aspect of the invention is a method of generating an engineered restored frame shift in a gene of a cell, comprising: (a) contacting the genome with a site-directed nuclease ("SDN") and at least two guide nucleic acids, wherein the at least two guide nucleic acids target at least two target sequences within the gene; (b) permitting the SDN to cut the gene at the at least two target sequences, thereby losing an intervening sequence between the at least two target sequences; and allowing endogenous DNA repairs to occur; whereby the endogenous DNA repairs results in a gene having an engineered restored frame shift. In one embodiment, the lost intervening sequence of step (b) comprises (N) base pairs, where (N) is a multiple of 3.

Yet another aspect of the invention is a method of generating a haploid wheat plant, comprising: (a) obtaining a wheat plant; (b) crossing the wheat plant to the wheat plant comprising a mutated CENH3 gene; and (c) selecting a progeny generated from the crossing step; wherein the progeny is a haploid wheat plant. In one embodiment, the wheat plant of step (a) is the paternal parent. In another embodiment, the wheat plant of step (a) is the maternal parent. In another embodiment, the method comprises a further step of converting the progeny wheat plant into a doubled haploid wheat plant.

It is another aspect of the invention to provide a wheat plant comprising a mutated CENH3 allele comprising a nucleic acid sequence at least 70% identical to a sequence selected from the group consisting of SEQ ID NO: 53-73, wherein the mutation is an restored frame shift mutation, and wherein the wheat plant generates haploid progeny when crossed with a wildtype diploid wheat plant. In one embodiment, the wheat plant comprises at least one copy of the mutated CENH3 allele: in another embodiment, the wheat plant comprises at least two copies of the mutated CENH3 allele: in yet another embodiment, the wheat plant comprises at least three copies of the mutated CENH3 allele. In one embodiment, the mutated CENH3 allele comprises a nucleic acid sequence 80, 90, 95, or 100% identical to SEQ ID NO: 53-73.

TABLE 1

BRIEF DESCRIPTION OF THE SEQUENCES IN THE SEQUENCE LISTING

| SEQ ID NO: | Pimer ID (or Probe ID) | Location or function | Brief Description |
|---|---|---|---|
| 1 | S2-α1A | 5' UTR of TaCenH3α-A | TaCenH3α-A genomic sequence cloning in Fielder |
| 2 | As-α1A/B/D | Exon 5 of TaCenH3α-A/B/D | |
| 3 | S-α1A/B/D | Exon 5 of TaCenH3α-A/B/D | |
| 4 | As-α1A | Exon 7 of TaCenH3α-A | |

TABLE 1-continued

BRIEF DESCRIPTION OF THE SEQUENCES IN THE SEQUENCE LISTING

| SEQ ID NO: | Pimer ID (or Probe ID) | Location or function | Brief Description |
|---|---|---|---|
| 5 | S-α1B | 5' UTR of TaCenH3α-B | TaCenH3α-B genomic sequence cloning in Fielder |
| 6 | As-α1A/B | Exon 5 of TaCenHBα-A/B | |
| 7 | S-α1A/B/D | Exon 5 of TaCenH3α-A/B/D | |
| 8 | As-α1B/D | Exon 7 of TaCenH3α-B/D | |
| 9 | S2-α1D | 5' UTR of TaCenH3α-D | TaCenH3α-D genomic sequence cloning in Fielder |
| 10 | As-α1A/B/D | Exon 5 of TaCenH3α-A/B/D | |
| 11 | S-α1A/B/D | Exon 5 of TaCenH3α-A/B/D | |
| 12 | As-α1B/D | Exon 7 of TaCenH3α-B/D | |
| 13 | qRT(A)-S | Sense primer | TaCenH3α-A expression |
| 14 | qRT(A)-As | Antisense primer | |
| 15 | qRT(A)-probe | Probe | |
| 16 | qRT(B)-S | Sense primer | TaCenH3α-B expression |
| 17 | qRT(B)-As | Antisense primer | |
| 18 | qRT(B)-probe | Probe | |
| 19 | qRT(B)-S | Sense primer | TaCenH3α-D expression |
| 20 | qRT(B)-As | Antisense primer | |
| 21 | qRT(B)-probe | Probe | |
| 22 | TQ1115-S | Sense primer | Control assay for the qRT-PCR, targeting ADP-ribosylation factor |
| 23 | TQ1115-As | Antisense primer | |
| 24 | TQ1115-probe | Probe | |
| 25 | gRNA1 | sgRNA targeting exon2-intron2 junction | |
| 26 | gRNA2 | sgRNA targeting intron3-exon4 junction | TaCenH3α sgRNAs |
| 27 | gRNA3 | sgRNA targeting exon1 | |
| 28 | gRNA4 | sgRNA targeting intron2-exon3 junction | |
| 29 | KW2917R | Antisense primer | |
| 30 | KW2917F1 | Sense primer | KASP assay - 2917 |
| 31 | KW2917F2 | Sense primer | |
| 32 | KWI1728R | Antisense primer | |
| 33 | KW11728F1 | Sense primer | KASP assay - 11728 |
| 34 | KW11728F2 | Sense primer | |
| 35 | KW11091R | Antisense primer | |
| 36 | KW11091F1 | Sense primer | KASP assay - 11091 |
| 37 | KW11091F2 | Sense primer | |
| 38 | KW11511R | Antisense primer | |
| 39 | KW11511F1 | Sense primer | RASP assay - 11511 |
| 40 | KW11511F2 | Sense primer | |
| 41 | KW11129R | Antisense primer | |
| 42 | KW11129F1 | Sense primer | KASP assay - 11129 |
| 43 | KW11129F2 | Sense primer | |
| 44 | e35S -S | Sense primer | |
| 45 | e35S -As | Antisense primer | Transgenic copy number check |
| 46 | e35S-probe | Probe | |
| 47 | PMI - S | Sense primer | |
| 48 | PMI - As | Antisense primer | Transgenic copy number check |
| 49 | PMI - probe | Probe | |
| 50 | FA | Sense primer | TaCENH3α-A edit sequencing primers |
| 51 | R3 | Antisense primer | |
| 52 | M13R | Antisense primer | Clone sequence primer |
| 53 | M13F | Sense primer | |
| 54 | F1 | Sense primer | TaCENH3α RT-PCR primer |
| 55 | R1 | Antisense primer | |
| 56 | A* genomic sequence in A004A | gRNA1, ins A; gRNA2, ins A | Genomic sequence in TaCENH3α-A |
| 57 | A* CDS sequence in A004A | Restored frame shift in N terminal | Restored frame shift in N terminal in TaCENH3α-A |
| 58 | a CDS sequence in A004A | Premature stop | Loss of function in TaCENH3α-A |
| 59 | A* protein sequence in A004A | Restored frame shift in N terminal | Restored frame shift in N terminal in TaCENH3α-A |
| 60 | a protein sequence in A004A | Premature stop | Loss of function in TaCENH3α-A |
| 61 | B genomic sequence in A004A | gRNA1, WT; gRNA2, WT | WT TaCENH3α-B |
| 62 | d genomic sequence in A004A | gRNA1, WT; gRNA2, ˆA | Loss of function in TaCENH3α-D |
| 63 | A* genome sequence in C003A | gRNA1, ΔG; gRNA2 ˆA | Transgenic copy number check |
| 64 | A* CDS sequence in C003A | gRNA1, ΔG; gRNA2, ˆA | Restored frame shift in N terminal in TaCENH3α-A |
| 65 | A* protein sequence in C003A | gRNA1, ΔG; gRNA2, ˆA | Restored frame shift in N terminal in TaCENH3α-A |
| 66 | b genomic sequence in C003A | gRNA1, WT; gRNA2, ˆA | Loss of function in TaCSENH3α-B |
| 67 | b protein sequence in C003A | gRNA1, WT; gRNA2, ˆA | Loss of function in TaCENH3α-B |
| 68 | d genomic sequence in C003A | gRNA1, WT; gRNA2, ˆA | Loss of function in TaCENH3α-D |
| 69 | A* genomic sequence in A073A | gRNA3, ˆA; gRNA4, ΔG | Restored frame- shift in N terminal in TaCENH3α-A |
| 70 | A* CDS sequence in A073A | gRNA3, ˆA; gRNA4, ΔG | Restored frame shift in N terminal in TaCENH3α-A |
| 71 | A* protein sequence in A073A | gRKA3, ˆA; gRNA4, ΔG | Restored frame shift in N terminal in TaCENH3α-A |
| 72 | b genomic sequence in A073A | gRNA3, WT; gRNA4, ˆA | Loss of function in TaCENH3α-B |

TABLE 1-continued

BRIEF DESCRIPTION OF THE SEQUENCES IN THE SEQUENCE LISTING

| SEQ ID NO: | Pimer ID (or Probe ID) | Location or function | Brief Description |
| --- | --- | --- | --- |
| 73 | d genomic sequence in A073A | gRNA3, ΔGTC; gRNA4, ˆA | Loss of function in TaCENH3α-D |
| 74 | | | Construct 24195 |
| 75 | | | Construct 24194 |
| 76 | | | Amino acid sequence lost in RES |
| 77 | | | Amino acid sequence added in RES |
| 78 | | | Amino acid sequence added in RES |
| 79 | SQ-1 primer | | |

BRIEF DESCRIPTION OF THE FIGURES

FIG. 1 shows the TaCenH3α gene structure and relative gRNA locations. Exons are numbered and represented by thick bars. Introns are represented by thin lines. Length of both is represented by width.

DEFINITIONS

This invention is not limited to the particular methodology, protocols, cell lines, plant species or genera, constructs, and reagents described herein. The terminology used herein is for the purpose of describing particular embodiments only, and is not intended to limit the scope of the present invention, which will be limited only by the appended claims. It must be noted that as used herein and in the appended claims, the singular forms "a," "and," and "the" include plural reference unless the context clearly dictates otherwise. Thus, for example, reference to "a plant" is a reference to one or more plants and includes equivalents thereof known to those skilled in the art, and so forth. As used herein, the word "or" means any one member of a particular list and also includes any combination of members of that list (i.e., includes also "and").

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means±1° C., preferably +0.5° C. Where the term "about" is used in the context of this invention (e.g., in combinations with temperature or molecular weight values) the exact value (i.e., without "about") is preferred.

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, PERSING et al., Ed., American Society for Microbiology, Washington, D.C. (1993). The product of amplification is termed an "amplicon." The term "biallelic" refers to a gene pair that is neither homozygous (AA or aa) nor heterozygous (Aa). Rather, both genes in the pair have been edited but not identically. For example, the CenH3 gene pair on the A chromosome in this invention may comprise one RFS mutation in one allele resulting in a knock-down of the gene upon expression, while the other allele comprises a knock-out mutation. This may be indicated symbolically as "A*a" and is indicative of a biallelic mutation.

The term "specific DNA sequence" indicates a polynucleotide sequence having a nucleotide sequence homology of more than 80%, preferably more than 85%, more preferably more than 90%, even more preferably more than 95%, still more preferably more than 97%, most preferably more than 99% with another named sequence.

"cDNA" refers to a single-stranded or a double-stranded DNA that is complementary to and derived from mRNA. The term "centromere-specific variant of histone H3 protein" ("CenH3 protein" or simply "CENH3"), as used herein, refers to a protein that is a member of the kinetochore complex. CenH3 protein is also known as CENP-A protein. The kinetochore complex is located on chromatids where the spindle fibers attach during cell division to pull sister chromatids apart. CenH3 proteins belong to a well-characterized class of proteins that are variants of H3 histone proteins. These proteins are essential for proper formation and function of the kinetochore, and help the kinetochore associate with DNA. Cells that are deficient in CenH3 fail to localize kinetochore proteins on chromatids and show strong chromosome segregation defects (i.e., all chromosomes from the plant expressing the deficient CenH3 protein are eliminated or lost, leading to a change in the ploidy of somatic cells (e.g., reduction in the number of chromosome set such as diploid to haploid)). Therefore, CenH3 proteins have been subject to intensive research for their potential use in doubled haploid production system. CenH3 proteins are characterized by a variable tail domain (also referred to as "N-terminal domain" or "N-terminal tail domain") and a conserved histone fold domain (also referred to as "C-terminal domain") made up of three alpha-helical regions connected by loop sections. The CenH3 histone fold domain is relatively well conserved between CenH3 proteins from different species. The histone fold domain is located at the carboxyl terminus of an endogenous CenH3 protein. In contrast to the histone-fold domain, the N-terminal tail domain of CenH3 is highly variable even between closely related species.

"CenH3-encoding polynucleotide having one or more active mutations" refers to a non-endogenous or endogenous mutated CenH3-encoding polynucleotide that encodes a CenH3 protein having one or more active mutations, which when present in a plant in the absence of its endogenous CenH3-encoding polynucleotide and/or endogenous CenH3 protein, allows the plant to be viable, and allows generation of haploid progeny, or progeny with aberrant ploidy, when the plant is crossed with a wild-type plant. The plant comprising a CenH3-encoding polynucleotide having one or more active mutations may be referred to as a "modified plant." The percentage of haploid progeny or progeny with aberrant ploidy that is generated upon crossing with a wild-type plant can, for instance, be at least 0.1, 0.5, 1, 5, 10, 20 percent or more. A mutation that causes a transition from the endogenous CenH3-encoding polynucleotide to a CenH3-encoding polynucleotide having one or more active mutations is herein referred to as an active mutation. An active mutation in a CenH3 protein context may result, among other things, in reduced centromere loading, a less functional CenH3 protein and/or a reduced functionality in the separation of chromosomes during cell division. One or more active mutations may be introduced into the CenH3-encoding polynucleotide by any of several methods well-known to the skilled person, for example, by random mutagenesis, such as induced by treatment of seeds or plant cells with chemicals or radiation, targeted mutagenesis, the application of endonucleases, by generation of partial or complete protein domain deletions, or by fusion with heterologous sequences.

A plant may be made to lack the endogenous CenH3-encoding polynucleotide by knocking out or inactivating the endogenous CenH3-encoding polynucleotide. Alternatively, the endogenous CenH3-encoding polynucleotide may be modified to encode an inactive or non-functional CenH3 protein.

The modified plant comprising the CenH3-encoding polynucleotide having one or more active mutations as taught herein may be crossed to a wild-type plant either as a pollen parent or as an ovule parent. In an embodiment, a CenH3 protein having one or more active mutations may comprise 1, 2, 3, 4, 5, 6, 7, 8, 9, 10, 12, 15, 20 or more amino acid changes relative to the endogenous CenH3 protein. In an embodiment, a CenH3-encoding polynucleotide having one or more active mutations has 70, 75, 80, 85, 90, 95, 96, 97, 98, 99, 99.5 percent sequence identity to the endogenous CenH3-encoding polynucleotide, preferably over the full length. The skilled person would readily be able to ascertain whether or not a modified plant as taught herein comprises one or more active mutations. For example, the skilled person may make use of predictive tools such as SIFT (Kumar P, Henikoff S, Ng P C. (2009) Predicting the effects of coding non-synonymous variants on protein function using the SIFT algorithm. Nat Protoc; 4(7): 1073-81. doi: 10.1038/nprot.2009.86) to propose such active mutation. The one or more active mutations may then be made in a plant, and expression of endogenous CenH3 protein in the plant should be knocked out. The plant may be considered to comprise one or more active mutations when the percentage of haploid progeny or progeny with aberrant ploidy that is generated upon crossing with a wild-type plant is at least 0.1, 0.5, 1, 5, 10, 20 percent or more.

Crossing a plant that lacks an endogenous CenH3-encoding polynucleotide, or that lacks expression of endogenous CenH3 protein, and that expresses a CenH3 protein having one or more active mutations either as a pollen or as an ovule parent with a wildtype plant (i.e., it expresses an endogenous CenH3 protein) results in progeny that is haploid or shows aberrant ploidy. Such a plant comprises only chromosomes of the parent that expresses the endogenous CenH3 protein, and no chromosomes of the plant expressing the CenH3 protein having one or more active mutation.

The term "aberrant ploidy" as used herein refers to a situation where a cell comprises an aberrant or abnormal number of sets of chromosomes. For instance, a cell having one or three sets of chromosomes per cell when the usual number is two is a cell having aberrant ploidy. In the present invention, the active mutant CenH3 proteins and methods using them, can be used to generate mutant plants having aberrant ploidy, e.g., to generate haploid plants while the non-mutant plant is diploid. The haploid plants can be used to accelerate breeding programs to create homozygous lines and obviate the need for inbreeding.

The term "chimeric construct", "chimeric gene". "chimeric polynucleotide" or chimeric nucleic acid" (and similar terms) as used herein refers to a construct or molecule comprising two or more polynucleotides of different origin assembled into a single nucleic acid molecule. The term "chimeric construct", "chimeric gene". "chimeric polynucleotide" or "chimeric nucleic acid" refers to any construct or molecule that contains (1) polynucleotides (e.g., DNA), including regulatory and coding polynucleotides that are not found together in nature (i.e., at least one of polynucleotides is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In a preferred aspect of the present invention the chimeric construct, chimeric gene, chimeric polynucleotide or chimeric nucleic acid comprises an expression cassette comprising a polynucleotides of the present invention under the control of regulatory polynucleotides, particularly under the control of regulatory polynucleotides functional in plants.

The term "chromosome" is used herein as recognized in the art as meaning the self-replicating genetic structure in the cellular nucleus containing the cellular DNA and bearing the linear array of genes.

A "coding polynucleotide" is a polynucleotide that is transcribed into RNA, such as mRNA, rRNA, tRNA, snRNA, sense RNA or antisense RNA. Preferably the RNA is then translated in an organism to produce a protein. It may constitute an "uninterrupted coding polynucleotide", i.e., lacking an intron, such as in a cDNA, or it may include one or more introns bounded by appropriate splice junctions. An "intron" is a poly(ribo)nucleotide which is contained in the primary transcript but which is removed through cleavage and religation of the RNA within the cell to create the mature mRNA that can be translated into a protein.

The term "doubled haploid plant" as used herein refers to a genotype formed when haploid cells undergo chromosome doubling. Artificial production of doubled haploids is important in plant breeding. Doubled haploids can be produced in vivo or in vitro. Haploid embryos are produced in vivo by parthenogenesis, pseudogamy, or chromosome elimination. A wide variety of in vitro methods are known for generating doubled haploid organisms from haploid organisms. A non-limiting example of a method for generating doubled haploid in vitro consist of treating somatic haploid cells, haploid embryos, haploid seeds, or haploid plants produced from haploid seeds with a chromosome doubling agent such as colchicine. In the present invention, homozygous double haploid plants can be regenerated from haploid cells by contacting the haploid cells with chromosome doubling agents, such as colchicine, anti-microtubule herbicides, or nitrous oxide to create homozygous doubled haploid cells. Methods of chromosome doubling are disclosed in, for example, U.S. Pat. Nos. 5,770,788; 7,135,615, and US Patent Publication Nos. 2004/0210959 and 2005/0289673; Antoine-Michard, S. et al., Plant Cell, Tissue Organ Cult., Cordrecht, the Netherlands, Kluwer Academic Publishers 48(3):203-207 (1997): Kato, A., Maize Genetics Cooperation Newsletter 1997, 36-37; and Wan, Y. et al., Trends Genetics 77: 889-892 (1989). Wan. Y. et al., Trends Genetics 81: 205-21 1 (1991), the disclosures of which are incorporated herein by reference. Double haploid plants can be further crossed to other plants to generate F1, F2, or subsequent generations of plants with desired traits. Conventional inbreeding procedures take seven generations to achieve approximately complete homozygosity, whereas doubled haploidy achieves it in one generation.

The term "E0" refers to the edited plant in the first instance. That is, a plant cell which is edited by, e.g., CRISPR, and then allowed to mature into a plant has become the E0 plant. An E1 plant is the edit-comprising progeny (usually but not necessarily self-fertilized) of the E0. Likewise, an E2 plant is the edit-comprising progeny (usually but not necessarily self-fertilized) of the E1 plant. An E3, E4, E5, etc., plant is likewise generationally removed from the E0 plant.

The terms "gene editing," "editing," "genome editing," "GE," and the like refer to site-specific mutations made at a target sequence. This may also be referred to as "targeted mutagenesis." As used herein, the term "targeted mutagenesis" or "mutagenesis strategy" refers to any method of mutagenesis that results in the intentional mutagenesis of a chosen gene. Targeted mutagenesis includes the methods CRISPR, TILLING, TALEN, and other methods not yet discovered but which may be used to achieve the same outcome.

Mutagenesis may be performed in accordance with any of the techniques known in the art, such as, and not limited to, synthesizing an oligonucleotide having one or more mutations within the sequence of a particular regulatory sequence. In particular, site-specific mutagenesis is a technique useful in the preparation of promoter mutants, through specific mutagenesis of the underlying DNA. RNA-guided endonucleases ("RGEN," e.g., CRISPR/Cas9) may also be used. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered. See generally, U.S. Pat. No. 10,285,348, incorporated by reference herein in its entirety.

The terms "edited N-terminal tail" or "edited N-terminal domain" are used interchangeably here throughout.

The term "endogenous" as used in the context of the present invention in combination with protein or gene means that said protein or gene originates from the plant in which it is still contained. Often an endogenous gene will be present in its normal genetic context in the plant. In another context, the term "endogenous" can refer to normal functions of a cell. For example and not by way of limitation, "endogenous DNA repair" refers to a cell's normal DNA repair mechanisms, enzymes, and processes.

The term "expression" when used with reference to a polynucleotide, such as a gene, ORF or portion thereof, or a transgene in plants, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (e.g. if a gene encodes a protein), through "translation" of mRNA.

Gene expression can be regulated at many stages in the process. For example, in the case of antisense or dsRNA constructs, respectively, expression may refer to the transcription of the antisense RNA only or the dsRNA only. In embodiments, "expression" refers to the transcription and stable accumulation of sense (mRNA) or functional RNA. "Expression" may also refer to the production of protein.

The terms "homology", "sequence similarity" or "sequence identity" of nucleotide or amino acid sequences mean a degree of identity or similarity of two or more sequences and may be determined conventionally by using known software or computer programs such as the Best-Fit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2:482-489 (1981), to find the best segment of identity or similarity between two sequences. Sequence comparison between two or more polynucleotides or polypeptides is generally performed by comparing portions of the two sequences over a comparison window to identify and compare local regions of sequence similarity. The comparison window is generally from about 20 to 200 contiguous nucleotides. Gap performs global alignments: all of one sequence with all of another similar sequence using the method of Needleman and Wunsch, J. Mol. Biol. 48:443-453 (1970). When using a sequence alignment program such as BestFit to determine the degree of DNA sequence homology, similarity or identity, the default setting may be used, or an appropriate scoring matrix may be selected to optimize identity, similarity or homology scores. Similarly, w % ben using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The term "locus" refers to a position (e.g., of a gene, a genetic marker, or the like) on a chromosome of a given species.

The term "primer", as used herein, refers to an oligonucleotide which is capable of annealing to the amplification target allowing a DNA polymerase to attach, thereby serving as a point of initiation of DNA synthesis when placed under conditions in which synthesis of primer extension product is induced, e.g., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer is generally sufficiently long to prime the synthesis of extension products in the presence of the agent for polymerization. The exact lengths of the primers will depend on many factors, including temperature and composition (A/T and G/C content) of primer. A pair of bi-directional primers consists of one forward and one reverse primer as commonly used in the art of DNA amplification such as in PCR amplification. It will be understood that "primer," as used herein, may refer to more than one primer, particularly in the case where there is some ambiguity in the information regarding the terminal sequence(s) of the target region to be amplified. Hence, a "primer" includes a collection of primer oligonucleotides containing sequences representing the possible variations in the sequence or includes nucleotides which allow a typical base pairing. The oligonucleotide primers may be prepared by any suitable method. Methods for preparing oligonucleotides of specific sequence are known in the art, and include, for example, cloning and restriction of appropriate sequences, and direct chemical synthesis. Chemical synthesis methods may include, for example, the phospho di- or tri-ester method, the diethylphosphoramidate method and the solid support method disclosed in, for example, U.S. Pat. No. 4,458,066. The primers may be labeled, if desired, by incorporating means detectable by, for instance, spectroscopic, fluorescence, photochemical, biochemical, immunochemical, or chemical means. Template-dependent extension of the oligonucleotide primer(s) is catalyzed by a polymerizing agent in the presence of adequate amounts of the four deoxyribonucleotide triphosphates (dATP, dGTP, dCTP and dTTP, i.e. dNTPs) or analogues, in a reaction medium which is comprised of the appropriate salts, metal cations, and pH buffering system. Suitable polymerizing agents are enzymes known to catalyze primer- and template-dependent DNA synthesis. Known DNA polymerases include, for example, *E. coli* DNA polymerase 1 or its Klenow fragment, T4 DNA polymerase, and Taq DNA polymerase. The reaction conditions for catalyzing DNA synthesis with these DNA polymerases are known in the art. The products of the synthesis are duplex molecules consisting of the template strands and the primer extension strands, which include the target sequence. These products, in turn, serve as template for another round of replication. In the second round of replication, the primer extension strand of the first cycle is annealed with its complementary primer; synthesis yields a "short" product which is bound on both the 5'- and the 3'-ends by primer sequences or their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount may vary, and is determined by the function which the product polynucleotide is to serve. The PCR method is well described in handbooks and known to the skilled person. After amplification by PCR, the target polynucleotides may be detected by hybridization with a probe polynucleotide which forms a stable hybrid with that of the target sequence under low, moderate or even highly stringent hybridization and wash conditions. If it is expected that the probes will be essentially completely complementary (i.e., about 99% or greater) to the target sequence, highly stringent conditions may be used. If some mismatching is expected, for example if variant strains are expected with the result that the probe will not be completely complementary, the stringency of hybridization may be lessened. However, conditions are typically chosen which rule out nonspecific/adventitious binding. Conditions, which affect hybridization, and which select against non-specific binding are known in the art, and are described in, for example, Sambrook and Russell, 2001. Generally, lower salt concentration and higher temperature increase the stringency of hybridization conditions. "PCR primer" is preferably understood within the scope of the present invention to refer to relatively short fragments of single-stranded DNA used in the PCR amplification of specific regions of DNA.

The terms "protein," "peptide" and "polypeptide" are used interchangeably herein.

The term "promoter" refers to a polynucleotide, usually upstream (5') of its coding polynucleotide, which controls the expression of the coding polynucleotide by providing the recognition for RNA polymerase and other factors required for proper transcription.

The term "site-directed nuclease" refers to any enzyme guided by a nucleotide sequence to a target sequence within a strand of DNA. The site-directed nuclease is preferably CRISPR-based, but could also be a meganuclease, a transcription-activator like effector nuclease (TALEN), or a zinc finger nuclease. Site-directed nuclease(s) may be referred to by the acronym "SDN." SDNs include but are not limited to meganucleases (MNs), zinc-finger nucleases (ZFNs), transcription-activator like effector nucleases (TALENs), Cas9 nuclease, Cpf1 (Cas12a) nuclease, dCas9-FokI, dCpf1-FokI, chimeric Cas9-cytidine deaminase, chimeric Cas9-adenine deaminase, chimeric FEN1-Fok1, and Mega-TALs, a nickase Cas9 (nCas9), chimeric dCas9 non-FokI nuclease and dCpf1 non-FokI nuclease; and further wherein the guide nucleic acid is a guide RNA.

The terms "stringent conditions" or "stringent hybridization conditions" include reference to conditions under which a polynucleotide will hybridize to its target sequence to a detectably greater degree than other sequences (e.g., at least 2-fold over background). Stringent conditions are sequence-dependent and will be different in different circumstances. By controlling the stringency of the hybridization and/or washing conditions, target polynucleotides can be identified which are 100% complementary to the probe (homologous probing). Alternatively, stringency conditions can be adjusted to allow some mismatching in sequences so that lower degrees of similarity are detected (heterologous probing). Typically, stringent conditions will be those in which the salt concentration is less than approximately 1.5 M Na ion, typically about 0.01 to 1.0 M Na ion (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions also may be achieved with the addition of destabilizing agents such as formamide. Exemplary low stringency conditions include hybridization with a buffer solution of 30 to 35% formamide. 1 M NaCl, 1% SDS (w/v; sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the Tm can be approximated from the equation of Meinkoth and Wahl (Anal. Biochem., 138:267-284, 1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays". Elsevier, N.Y. (1993); and Current Protocols in Molecular Biology, Chapter 2, Ausubel, et al., eds., Greene Publishing and Wiley-Interscience, New York (1995). Methods of stringent hybridization are known in the art which conditions can be calculated by means known in the art. This is disclosed in Sambrook et al. Molecular Cloning: A Laboratory Manual, 2nd Ed., Cold Spring Harbor Laboratory Press, 1989, Cold Spring Harbor, N.Y. and Current Protocols in Molecular Biology, Ausebel et al, eds., John Wiley and Sons, Inc., 2000. Methods of determining percent sequence identity are known in the art, an example of which is the GCG computer sequence analysis software (GCG, Inc, Madison Wis.).

As used herein, the term "restored frame shift" ("RFS") refers to a mutation or series of mutations in a gene which, individually or in combination, interrupts the coding sequence of a gene yet does not alter the frame of the coding sequence. This may also be referred to as "restoring frame synchronization." For example, a DNA coding sequence comprises a series of codons. Each codon comprises three nucleotides, and each codon-when transcribed into RNA-codes for one amino acid upon translation. An insertion/deletion mutation ("indel") of one or two nucleotides into the coding sequence will cause a shift in the coding frame (a "frame shift"). However, insertions or deletions, whether individually or in combination, which occur cumulatively as a multiple of three will restore the codons to its original frame, even if the coding sequence itself is altered. See. e.g., B. N. Ames and H. J. Whitfield, Jr., *Frameshift Mutagenesis in Salmonella*, COLD SPRING HARB. SYMP. QUANT. BIOL. 31:221-225 (1966). For example, and within the scope of this definition, a sequence comprising at least two indel mutation deletions—whether consecutive or not—and in which the indel mutations cause the reading frame to be restored to its original frame is a sequence comprising a restored frameshift mutation. The term "engineered restored frame shift" may also be used to describe a RFS mutation which has been created by genome editing or genome modification.

As used herein, the term "large deletion" ("LD") refers to a mutation which causes the loss of several consecutive nucleotides. In particular, a large deletion refers to the loss of 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more nucleotides. In some embodiments, the sequence lost in an LD will be a multiple of 3 (i.e., 3, 6, 9, 12, 15, 18, 21, 24, 27, 30, etc.) In other embodiments, an LD mutation may also occur in conjunction with an indel mutation elsewhere in the same sequence, thereby causing a restored frame shift mutation.

In the context of the present invention, the use of the term "wildtype" or "wildtype plant" refers to a plant which does not carry a mutant CenH3 protein or gene (i.e., does not comprise one or more active mutations taught here) and which endogenously expresses or produces functional CenH3 genes and proteins.

DETAILED DESCRIPTION

Here, we induced alternative splicing in wheat (*Triticum aestivum*) by applying CRISPR-Cas9 to edit cis-splicing sequences including 5' and 3' splice sites. We chose wheat as the target model organism because wheat is hexaploid, which gives wheat functional genomic redundancy. As a target gene, we chose the centromeric protein-encoding gene *CENTROMERIC HISTONE* 3 ("CenH3") because modifications in this gene should produce plants with value for crop breeding. CenH3 is responsible for the faithful segregation of chromosomes during cell division. Unlike H3 and other conventional histones, CENH3 has a long, hypervariable N-terminal tail. See J. Monen, et al. *Separase Cleaves the N-Tail of the CENP-A Related Protein CPAR-1 at the Meiosis I Metaphase-Anaphase Transition in C. elegans*, PLOS ONE 10:e0125382 (2015). Directed or natural modification of the tail triggers compensatory changes in the kinetochore, which may enable CENH3 to drive speciation through impairing meiosis or inhibiting zygotic chromosome segregation. See I. Lermontova, et al., *Knockdown of CENH3 in Arabidopsis reduces mitotic divisions and causes sterility by disturbed meiotic chromosome segregation*, PLANT J 68:40-50 (2011) and M. Ravi and R. Bondada, *Genome Elimination by Tailswap CenH3: In Vivo Haploid Production in Arabidopsis thaliana*, METHODS MOL BIOL 1469:77-99 (2016). Swapping the N-terminal tail with an H3 tail led to haploid induction in *Arabidopsis* (M. Ravi and S. Chan, *Haploid plants produced by centromere-mediated genome elimination*. NATURE 464:615-618 (2010)) and maize (T. Kelliher, et al., *Maternal Haploids are Preferentially Induced by CENH3-tailswap Transgenic Complementation in Maize*, FRONT. PLANT SCI., doi.org/10.3389/fpls.2016.00414 31(7):414 (2016). Haploid induction is an aberrant reproductive process that leads to ploidy reduction from one generation to the next. Haploids can be doubled to produce inbred lines, saving six generations of self-pollination normally required to generate new pure-bred stocks. Delivering the tail-swap approach to crops requires multiple generations to assemble the native allele knockout and stable insertion of transgenes. We were able to induce AS by directly editing N-terminal sequences in wheat CenH3. These novel CenH3 sequences were studied to determine whether and in what combination mutant CENH3 proteins might cause haploid induction in wheat. Under the circumstances we describe, it does.

Therefore, one embodiment of the invention is a wheat plant comprising at least an A genome, a B genome, and a D genome, wherein the B genome comprises a knock-out mutation in a CENH3 gene, and optionally wherein the D genome comprises a knock-out mutation in a CENH3 gene, and further wherein the A genome comprises a mutated CENH3 gene comprising at least one knock-down mutation at a 5' splice site of an intron. In one aspect, the knock-down mutation is a restored frame shift mutation or a large deletion mutation. In another embodiment, the wheat plant is homozygous for a knock-out mutation in a CENH3 gene in the B genome. In an alternate embodiment, the wheat plant is biallelic for a knock-out mutation in a CENH3 gene in the B genome. In another embodiment, the wheat plant is homozygous for a knock-out mutation in a CENH3 gene in the D genome. In an alternate embodiment, the wheat plant is biallelic for a knock-out mutation in a CENH3 gene in the D genome. In yet another embodiment, the wheat plant is homozygous, biallelic, or a combination thereof for a knock-out mutation in a CENH3 gene in the B genome and the D genome. In another embodiment, the wheat plant is homozygous for the restored frame shift CENH3 mutation; or it is heterozygous for the restored frame shift CENH3 mutation; or it is biallelic for the restored frame shift CENH3 mutation.

Another aspect of the invention is a method of generating a haploid-inducing wheat plant, the method comprising: (a) obtaining at least a wheat plant cell comprising at least three genomes; (b) mutating two of the three genomes to obtain homozygous knock-out mutations in a CENH3 gene; (c) mutating the third genome to obtain a homozygous knock-down mutation in a CENH3 gene; and (d) generating a wheat plant therefrom comprising homozygous knock-out mutations in a CENH3 gene of two of the three genomes and further comprising a homozygous knock-down mutation in a CENH3 gene of the third genome; whereby the wheat plant generated from step (d) produces haploid progeny when crossed with a wildtype wheat plant. In one embodiment, the three genomes comprise an A genome, a B genome, and a D genome. In another, the knock-out mutations in a CENH3 gene occur in the B and D genomes. In yet another, the knock-down mutation in a CENH3 gene occurs in the A genome. In one aspect, the knock-down mutations in a CENH3 gene in the A genome are restored frame shift mutations. In another aspect, the restored frame shift mutations are selected from the group consisting of SEQ ID NO: 56, a nucleic acid sequence 70% identical to SEQ ID NO: 56, SEQ ID NO: 63, a nucleic acid sequence 70% identical to SEQ ID NO: 63, SEQ ID NO: 69, and a nucleic acid sequence 70% identical to SEQ ID NO: 69.

Another aspect of the invention is a wheat plant comprising a mutated CENH3 gene comprising at least one deletion mutation in the N-terminal domain resulting in a frame shift, a restored frame shift, or a large deletion. Yet another aspect is a wheat plant comprising a mutated CENH3 gene comprising at least one insertion mutation in the N-terminal domain resulting in a frame shift, a restored frame shift, or a large deletion.

Another aspect of the invention is a method of generating an engineered restored frame shift in a gene of a cell, comprising: (a) contacting the genome with a site-directed nuclease ("SDN") and at least two guide nucleic acids, wherein the at least two guide nucleic acids target at least two target sequences within the gene; (b) permitting the SDN to cut the gene at the at least two target sequences, thereby losing an intervening sequence between the at least two target sequences; and allowing endogenous DNA repairs to occur: whereby the endogenous DNA repairs results in a gene having an engineered restored frame shift. In one embodiment, the lost intervening sequence of step (b) comprises (N) base pairs, where (N) is a multiple of 3.

Yet another aspect of the invention is a method of generating a haploid wheat plant, comprising: (a) obtaining a wheat plant; (b) crossing the wheat plant to the wheat plant comprising a mutated CENH3 gene: and (c) selecting a progeny generated from the crossing step; wherein the progeny is a haploid wheat plant. In one embodiment, the wheat plant of step (a) is the paternal parent. In another embodiment, the wheat plant of step (a) is the maternal parent. In another embodiment, the method comprises a further step of converting the progeny wheat plant into a doubled haploid wheat plant.

It is another aspect of the invention to provide a wheat plant comprising a mutated CENH3 allele comprising a nucleic acid sequence at least 70% identical to a sequence selected from the group consisting of SEQ ID NO; 56-73, wherein the mutation is an restored frame shift mutation, and wherein the wheat plant generates haploid progeny when crossed with a wildtype diploid wheat plant. In one embodiment, the wheat plant comprises at least one copy of the mutated CENH3 allele: in another embodiment, the wheat plant comprises at least two copies of the mutated CENH3 allele; in yet another embodiment, the wheat plant comprises at least three copies of the mutated CENH3 allele. In one embodiment, the mutated CENH3 allele comprises a nucleic acid sequence 80, 90, 95, or 100% identical to SEQ ID NO: 56-73.

EXAMPLES

Example 1: The Theory Behind Using Two N-Terminal Guide RNAs

CENH3-tailswap transgenes, when expressed heterologously in a line where the native CENH3 genes are knocked out, leads to haploid induction. See, e.g., U.S. Patent Application Publication No. 2019/0136250, incorporated herein by reference. This is called the tailswap approach. Importantly, there are no wildtype alleles in tailswap haploid inducer lines. The transgenes are inferred to have partial function and are capable of generating centromeres that are stable enough to get a normally-developing plant when homozygous. However, when the tailswap transgenes are heterologous with wildtype CENH3 in a cell, the tailswap transgenes are unstable and lead to successful haploid induction during outcross. It is critical in these designs of tailswap plants that the native CENH3 genes are knocked out and that the tailswap transgenes have significant alterations of the N-terminal domain combined with only minor, or preferably zero, alterations to the C-terminal domain. Haploid induction will not occur even if the mutant CENH3 genes encode CENH3 proteins that retain normal or near-normal functionality.

In order to achieve haploid induction in wheat, we directly edited the six CENH3α genes to knock out several copies and create modifications to the N-terminal domain (leaving the C-terminal domain intact) in still other copies. Based on our experiments measuring the gene expression of the A, B, & D genomes's CENH3α genes, we particularly focused on creating N-terminal modifications in the A genome, and knockouts in the B and D genome. If our edits were successful, we would leave zero copies of CENH3α normal (intact): All genes would be edited, but the outcomes of the editing would differ. Importantly, our editing design did not include any CENH3 transgenes—we simply wanted to create the partial function, N-terminal modified version of the A genome CENH3α through direct editing.

Typically, large alterations to regions encoding proteins can be achieved through CRISPR SDN II genome editing (also called allele replacement ("AR") or homologous recombination ("HR")), but the efficiency of that technology is extremely low in plants and only rarely achieved in wheat. Therefore, we designed an editing strategy using two guide RNAs ("gRNAs") that had the potential to modify CENH3α to create a partial loss of function allele that had a large alteration (a change of more than 5 amino acids) of the N-terminal domain and a native (unaltered) sequence for the C-terminal domain. This would require specific cuts at both guide RNA sites. We knew that the selected guide RNAs would also edit the B and D genome's copies of CENH3α, and this was intentional. In fact, due to the unpredictability of each specific editing outcome for two guide RNAs, we expected that most edited alleles would be full loss of function alleles (in A, B and D genome copies), due to frame-shifts in the coding sequence that resulted in premature stop codons that truncated the CENH3α protein product and thus were complete knockouts of the native gene. However we also knew that if all copies of the CENH3α gene were knocked out, the plants would die because partial function of CENH3α is required for plant development. If the same guides that created a modified, haploid inducer allele in the A genome could simultaneously (in the same plants) knock out the B and D genome's alleles, it would help us: The result would be a perfectly conceived haploid inducer line. Thus our aim was to use two gRNAs to mimic the tailswap transgenic system by direct editing, but our key inventive step was instead of doing any allele replacement or CENH3α transgene, we generated novel, modified variants through small indels created by the nuclease cutting at the two guide RNAs in the N-terminal domain.

However, not every pair of guides possible had the potential to combine to create an altered N-terminal domain paired with a functional C-terminal domain: Not every pair of guides could produce those "edited N-terminal tail" altered copies with partial functions and haploid induction potential. Many of the guides, after checking what the edits would lead to in terms of the amino acid sequence, would lead to premature stop codons. In other words, we realized that we had to specifically select guide RNAs that we predicted could generate a combination of edits at the target sites that would generate amino acid sequences in the mature CENH3α protein product that contained dramatic alterations to the N-terminal domain, but left the C-terminal domain unaffected. In particular, we planned to screen plants and identify those that contained such productive, N-terminal modified alleles for the A genome's copies of CENH3α, and which also had knock out alleles for the B and D genome's copies of CENH3α. Knowing that site-directed nuclease-mediated editing does not always occur right away during transformation, we reasoned that in the E0 generation, we may generate knockout (full loss of function) alleles for some of the copies and also some partial loss of function (haploid inducer) alleles for still other copies of the CENH3α gene, and that these materials may be able to generate haploids by self-pollination-assuming the male and female gametes (sperm and egg cells) have different edits or different combinations of alleles and thus potentially different centromeres. In other words, we thought we may find some haploids in the E1 generation plants. We hoped to let those observations guide us towards selecting certain E1 plants to genotype (i.e., genotype diploid siblings from populations that gave rise to some haploids upon self-pollination) and identify the E1 plants that had the partial loss of function alleles in a homozygous state. If we could do that then we would use those particular plants to test the haploid induction rate via outcrossing. In summary, we thought that once we created stably-mutated lines we would be able to test whether they were really haploid inducers, but we knew that we could not do that in the first generation because the editing may not be 'complete' by that point in time—and that we needed to test and retest haploid induction in diverse genotypes in the E1 and E2 generations.

There were many guide RNAs that we could choose from that had appropriate PAM sites, but only a select couple of pairs that could create our desired haploid inducer alleles. Regarding the desired alleles, one way that a pair of guide RNAs could generate such alleles would be for the editing of the first gRNA target site to generate a frameshift which is then restored by a compensatory mutation at the second target site that puts the transcript back into the correct (native) frame. This would result in an altered N-terminal domain amino acid sequence for the intervening string of amino acids between the two guide RNA target sites, and would restore a "native" sequence for the C-terminal domain. Such alleles we decided to call restored frame-shift ("RFS") alleles. Alternatively, simultaneous or near-simultaneous cutting at both guide RNA target sites could result in a deletion of the intervening nucleic acid sequence. In many cases that deletion would produce a frameshift in the downstream sequence, but in some cases such a deletion could happen to leave the 3' sequence of the transcript in the normal frame, such that a significant part of the N-terminal domain amino acid sequence is absent from the resulting protein product, but again the C-terminal domain is left intact. We decided to call these large deletion ("LD") alleles. Finally, in some cases, we designed the gRNAs to target the splice site junctions, and edits at these target sites may generate alternative splicing patterns (for instance, it could lead to intron retention or exon skipping). These alternatively spliced ("AS") alleles in most cases would lead to premature stop codons and genetic knock outs, but we also found one guide RNA that, if the right edits and the right splicing happened, would not lead to any premature stop codons in frame. Instead it could result in a large insertion in the mature transcript, resulting in a significant alteration in the N-terminal domain by inserting a long stretch of amino acids, but then a specific edit at the second target site could put the sequence back into frame for the C-terminal domain. In other words, with smart design of the gRNAs, splice site mutation may be predicted to generate mature mRNA transcript variants that alter the amino acid code of the N-terminal domain but restore the normal frame and sequence of the C-terminal domain.

In the following examples, we describe in detail the specific guide RNAs and edits we recovered, and the combinations of edits in specific plants. We show in detail how we generated haploid inducer lines in wheat by direct-editing the native CENH3 genes using two guide RNAs targeted to the hypervariable N-terminal domain. As designed, the plants having mutations at both target sites in some cases produced protein products that contained significant alterations to the N-terminal domain amino acid sequence, without affecting the C-terminal domain amino acid sequence. We selected and maintained edited lines that had these type of edited N-terminal tail altered alleles CENH3 alleles and made sure that the other copies of the CenH3 genes (from the A, B, and D genome) were knocked out by mutations produced by those same guide RNAs. We recovered and tested haploid induction in lines that had the desired mutations, including the combination of A genome RFS alleles with B and D genome knockouts. These same lines, with the right combination of edits that we had predicted to generate haploids, indeed led to haploid induction.

Example 2: Determining the gRNA Sequences to Edit the Fielder Genome's CENH3α Genes There are two CenH3 genes in hexaploid wheat, TaCen3α and TaCenH3β. The A, B, and D genomes's copies of both genes were cloned in the wheat variety "Fielder" with primers designed against genome sequence of the variety "Chinese Spring_v2". The sequences are given (SEQ ID NOs: 1-12). Previous studies have shown that viral-induced gene silencing ("VIGS") of TaCenH3α led to dwarfism and reduced root prolificacy, whereas silencing of TaCenH3β reduced seed set (Yuan et al., New Phytol. 206(2):839-51. 2015). As is the case for most wheat genes, the specific expression patterns and functions of each of the A, B, and D genomes's homologues are not well studied. For genome editing, we opted to modify TaCenH3α in the Fielder spring wheat variety, reasoning that mutations in this gene should not have as much of an impact on seed setting as mutations in TaCenH3β. Homologue-specific Taqman qPCR assays were used to query the expression level of TaCENH3α-A, -B. and -D (SEQ ID NOs: 13-21), in reproductive tissues (pollen, ovary, and anther) as well as juvenile leaf tissue. TaCenH3α-A and -B were expressed at high levels in anthers, pollen and ovaries while the TaCenH3α-D expression transcript was nearly absent (Table 2). In leaf, TaCenH3α-A was the predominant transcript, which may indicate that loss of function of this gene contributes to the dwarf phenotype after TaCenH3α silencing.

TABLE 2

Relative expression of TaCenH3α-A, TaCenH3α-B, and TaCenH3α-D.

| Tissue | Relative expression (Mean ± SD) | | |
|---|---|---|---|
| | TaCenH3α-A | TaCenH3α-B | TaCenH3α-D |
| Leaf | 1.88 ± 0.36 | 0.00 ± 0.00 | 0.01 ± 0.00 |
| Anther | 44.08 ± 19.62 | 46.66 ± 18.83 | 0.47 ± 0.12 |
| Pollen | 43.62 ± 23.69 | 54.21 ± 17.28 | 4.03 ± 1.38 |
| Ovary | 22.39 ± 11.50 | 15.54 ± 2.73 | 0.19 ± 0.05 |

The guide RNAs were picked using NGG PAM sites and by our predictions of the types of amino acid sequences that would result in the CENH3 protein product if certain edits were made at those target sites. Importantly, most of the guide RNAs that we considered would not able to generate combinations of edits that produced RFS or AS alleles. We focused on selecting the few pairs of gRNAs that could conceivable do so. Guide RNA1 (ACGTCGGCGACACCGGTGCG: SEQ ID NO: 25) (underlined is the approximate site of double stranded break cut induced by the CRISPR-Cas9 complex) is located at the exon 2-intron 2 junction region. This gRNA1 was driven by the TaU6 promoter. Guide RNA2 (CTTGTGG-GAGCAGGGGCAAC; SEQ ID NO: 26) targets just after the intron 3-exon 4 junction, driven by TaU6. Guide RNA2 will not edit the 3' splice acceptor site of intron 3 in most cases. The choice to use two guide RNAs was made so that we could produce significant alterations, e.g., RFS, LDs. or AS alleles, in the N-terminal domain while still leaving the C-terminal domain in frame. For instance, in some plants and edited alleles, both gRNAs will cut at the same time, resulting in a deletion of the intervening sequence. In some cases, the resulting repair will produce a frameshift which will knockout the protein. In other cases, it will produce a shortened LD transcript that lacks intron 2, all of exon 3, and a portion of exon 4, removing approximately the amino acid sequence RAGRAAAPGGAQGA (SEQ ID NO: 76) from the protein product, constituting a significant alteration of the N-terminal domain.

Alternatively, a non-simultaneous cut at both sites could generate a frameshift at gRNA1 (for instance, any indel that hits the coding sequence and is not a multiple of 3) which is restored at the gRNA2 site by a complimentary indel, thus putting the coding sequence back in its normal frame. For example, a 1 nucleotide ("nt") deletion at gRNA1 and a 1 nt insertion at gRNA2 would restore the coding frame, leading to an RFS allele. This allele would likely not be a loss of function, assuming there are no stop codons generated in the intervening frameshifted sequence. From our evaluation of the potential changes, we could see that at least one combination of edits would generate an RFS between gRNA1 and gRNA2 that did not have any stop codon in the intervening sequence. Thus, we could predict which pairs of small indels at gRNA1 and gRNA2 would combine to give us a functional RFS allele.

The two guide RNAs could generate alternatively spliced ("AS") alleles that also have the capacity to act as RFS or large insertion alleles. Guide RNA1 will cut between the GT (SEQ ID NO. 25, underlined above). That is the 5' splice donor site at the end of exon 2. AS alleles could be generated if the GT is modified such that intron 2 is not correctly spliced, leading to the retention of intron 2 in the coding sequence. Upon translation, the ribosome would read through this intron and generate a novel insertion of 44-47 amino acids, depending on the nature of the indels at gRNA1 and gRNA2. This novel insertion can be predicted by reading the new coding frame after factoring in the indels and the translation of the new mature mRNA. For instance, if gRNA1 and gRNA2 generate insertions of a single A nucleotide at both sites of TaCENH3α-A, the transcript may be alternatively spliced leading to an insertion of the amino acid sequence "VARDLPGSLPFRFVLFSVFWSDLLVTC-STECRGEPGGRRPQGGLKGQ" (SEQ ID NO: 77) with removal of the WT sequence "RRAGRAAAPGGAQGA" (SEQ ID NO: 76) from exon 3 before the normal sequence is restored by the gRNA mutation. Likewise, a different mutation at gRNA1 (for example, the deletion of GTG) combined with gRNA2 (deletion of a C) can similarly be predicted to cause alternative splicing to generate a novel insertion of "GTFPGRFLFVSSCFLFFGLTCSSPVRR-NAEASRAGGGPRGGSRG" (SEQ ID NO: 78) with the removal of the native sequence "RAGRAAAPGGAQGA" (SEQ ID NO: 76). We can also predict that other mutation combinations at gRNA1 and gRNA2 would generate frameshifts that are not put back into frame, leading to loss of function alleles. Similarly, alternative spliced alleles induced at other sites in the N-terminal region of CenH3 would not be able to generate modified mRNA sequences with a C-terminal domain restored to the normal amino acid sequence, because there would be stop codons generated in the introns retained, or after skipping one or more exons. Therefore, the gRNAs can be selected specifically for their capacity to generate large changes in the N-terminal domain while leaving the C-terminal domain intact and translated normally.

Example 3: Construct Design and Plant Transformation

After cloning the specific sequences of TaCENH3α-A, —B, and -D in the Fielder variety with primers designed against genome sequence of Chinese Spring, we selected the gRNAs according to PAM sites. gRNA1 (ACGTCGGCGACACCGGTGCG: SEQ ID NO: 25) locates in exon 2-intron 2 junction region (FIG. 1). gRNA2 (CTTGTGGGAGCAGGGGCAAC; SEQ ID NO: 26) targets just after the intron 3-exon 4 junction. SpCas9 gene was wheat codon-optimized with two NLSs at both ends and driven by sugarcane Ubi promoter with two enhancers. The gRNA cassettes including the wheat U6 promoter and gRNA scaffolds was synthesized by GenScript (www.genscript.com) and cloned into a binary vector, Construct 24194 (SEQ ID NO: 74).

Fielder was used for transformation, a spring wheat inbred. Immature embryos about 2.0-2.5 mm in diameter were harvested, sterilized with 70% ethanol for 1 min and 1% sodium hypochlorite for 10 min. After sterilization, immature embryos were isolated by scalpel and spatula into a small tube and centrifuged at 20,000×g at 4° C. for 10 min in inoculation medium. The isolated embryos were infected with *Agrobacterium* for 5 min, then transferred to co-cultivation medium at 23° C. in the dark for 2 days. The embryo axis was excised from the immature embryos before transferring to resting medium, cultured at 25° C. in the dark for 5 days, then transferred to selection medium containing mannose 15 g/L. See Y. Ishida, et al., *Wheat (Triticum aestivum* L.) *Transformation Using Immature Embryos*, METHODS IN MOLECULAR BIOLOGY 1223: 189-198 (2015). After 4 weeks, the vigorously grown calli were transferred to regeneration media to generate green plants. Surviving plants went through Taqman check, which analyzed the presence or absence of DNA segments from the transgenic DNA insertion: of these, only plants positive for 35S and PMI Taqman assays were sent to the greenhouse.

Example 4: Sequencing E0 Edited Plants

Genomic DNA was isolated from juvenile leaves of Taqman positive E0 plants. Sequencing was performed with high fidelity DNA polymerase, namely KOD-Plus-Neo (source; TOYOBO Life Science). TaCenH3α-A allele specific primers were used (FA, SEQ ID NO: 50; R3, SEQ ID NO: 51). PCR was performed as follows: 95° C. 5 min: 35 cycles of 95° C. 30 sec, 65° C. 30 sec, 68° C. 1min: 68° C. 10 min. PCR reaction mixture comprises 11.5 µl distilled water, 2.5 µl 10×PCR buffer for KOD-Plus-Neo, 1 µl 2 mM dNTPs, 1 µl 25 mM MgSO$_4$, 1 µl KOD-Plus-Neo DNA polymerase, 1 µl forward primer FA (10 µM), 1 µl reverse primer R3 (10 µM), and 1 µl genomic DNA. PCR products were sequenced directly via SQ-1 primer (SEQ ID NO: 79) or cloned into pEASY-Blunt Zero cloning vector (Transgen Biotech). M13R (SEQ ID NO: 52) and M13F (SEQ ID NO: 53) were used for colony sequencing.

Example 5: Wheat Event A004A

The wheat event A004A exhibited haploid induction. The event number A004A is one of hundreds of transgenic plants that were produced via transformation of construct 24194. Taqman assay followed by direct sequencing indicated that the genotype for the TaCENH3α genes were AA*BBdd at E0 seedling stage. Here, a capital letter indicates a wild-type TaCENH3α allele without editing, a lower-case letter indicates a loss-of-function of allele, and a capital letter with an asterisk (*) indicates a restored frame shift (RFS), large deletion (LD) or alternatively spliced (AS) allele, which means a putative haploid inducer allele. The A004A plant A* allele contains an adenine insertion at the target site for gRNA 1, and another adenine insertion at the target site of gRNA2 (SEQ ID NO:56). The adenine insertion at gRNA1 is actually in the intron, 3 bp downstream from the end of Exon 2, and right after the 5' splice junction. It does not itself disrupt the coding sequence, but it may alter the splicing pattern in some instances. The adenine insertion at gRNA2 is in Exon 3, and shifts the frame of the coding sequence. Prediction of the splicing pattern induced by the insertion of an Adenine at the gRNA1 target site indicates that this may be an AS allele that exhibits intron retention (IR) of intron number 2, because having an extra adenine after the 5' splice donor site can alter the initiation of intron removal, triggering alternative splicing. Alternative splicing in this case would to an insertion of many amino acids leading into exon 3. If there were alternative splicing, analysis of the outcome indicates that the sequences in exon 3 would be out of frame until the gRNA2 edit, which is another insertion of an adenine, restores the normal frame and amino acid code for the C-terminal domain.

To verify that the A004A A* allele is alternatively spliced and produces a putative haploid inducer allele, we examined the mature mRNA sequences of the CENH3α-A gene in A004A juvenile stage E0 leaf Total RNA of juvenile leaves was extracted using INVITROGEN TRIzol following manufacturer's instructions. cDNA was synthesized from 1 mg of total RNA via Superscript III first-strand synthesis system (Invitrogen) with oligo-dT primer. KOD-Plus-Neo (TOYOBO) was used to amplify TaCenH3α-A transcripts with primers F1 (SEQ ID NO:54) and RI (SEQ ID NO:55). PCR performed according to manufacturers instructions and as follows: 95° C. 5 min; 35 cycles of 95° C. 30 sec, 62° C. 20 sec, 68° C. 20 sec, 35 cycles; 68° C. 10 min. PCR reaction mixture comprises 11.5 µl distilled water, 2.5 µl 10×PCR buffer for KOD-Plus-Neo, 1 µl 2 mM dNTPs, 1 µl 25 mM MgSO$_4$, 1 µl KOD-Plus-Neo, 1 µl F1 primer (10 µM), 1 µl R1 primer (10 µM), and 1 µl cDNA. PCR product was purified by GeneJET PCR Purification Kit (Thermo Scientific) and cloned into pEASY-Blunt Zero cloning vector (Transgen Biotech). Primers M13R and M13F were used for colony sequencing. Several clones per PCR product were sequenced and analyzed by Vector NTI software (Invitrogen). Relative expression of splicing variants were calculated by number of clones. Analysis of the PCR sequencing of the colonies indicated the TaCENH3α-A mRNA in A004A has two transcripts, indicative of alternative splicing. One of the transcripts (SEQ ID NO:58), found in 8 out of 18 (44%) of colonies, was spliced using the canonical 5' splice site. For these transcripts, normal splicing of Intron 2 means that the gRNA1 edit did not impact the amino acid translation of the mature mRNA; however, the gRNA2 edit caused a frame-shift. So, in this instance the constitutively spliced mature mRNAs are actually knockout transcripts. On the other hand, 10 out of 18 (56%) of the colonies had mature mRNA transcripts with intron 2 retained (SEQ ID NO:57), leading to an N terminal RFS allele which contains 47 new amino acids, thus 32 amino acids were inserted from intron 2 along with 15 amino acids that are altered by the frame-shift in exon 3. This 32aa insertion and 47aa overall change severely alters the N terminal domain of the proteins produced by translation of the RFS mRNA. Importantly, the mature mRNA sequence that we obtained in our AS allele A004A-TaCENH3α-A* is the exact mature mRNA sequence outcome that we predicted would happen. A004A E0 plant was maintained through flowering. We did not observe any abnormal phenotypes, and the E1 seeds (after self-pollination) were harvested from the spikes produced by this plant.

The ploidy level of E1 progeny seeds, produced by self-pollination of the A004A plant, was checked. The seeds were planted and the seedlings that germinated were sampled and analyzed for DNA content by flow cytometry. Haploids were obtained in the first batch of progeny plants sowed; the haploid induction rate ("HIR") was 3.8%. In the second batch of seedlings, haploids were observed again, and the HIR was 4.2%. Wheat haploids are smaller than their diploid counterparts, similar to haploids in rice and corn. Importantly, these plants either did not have both copies of the "B" allele knocked out, or did not have a restored frameshift induced by a mutation at gRNA2 target site. This suggests that only the right combination of edits at both the target sites at gRNA1 and gRNA2 in the CENH3α-A gene, when paired with a knockout of both copies of the "B" allele, is sufficient to trigger haploid induction.

In the first batch, we observed two twin-seedling plants; both seedlings were haploids based on flow cytometry check. This indicates there are two haploid embryos in one seed. Twin embryos may be caused by a disruption of ovule development, which may be triggered in part by the edits in CENH3α, although more experimental work is needed to confirm this.

While we were slightly surprised that we observed haploids after self-pollination (because normally haploids are only induced in CENH3 modifications during outcross), the continuous capacity for editing the E0 plants mean that the male and female sex cells may inherit different sequences (edits) and thus have different centromere binding and kinetochore construction than each other, leading to haploidy after selfing.

Example 6: Wheat Event C003A

Plant C003A is edited such that the TaCenH3α genotype is A*abbdd at E0 plant stage. A* is introduced by deleting a guanine in gRNA1 and inserting an adenine in gRNA2. At the protein level, there is an eleven amino acid difference in N-terminal domain compared to the wildtype sequence. SEQ ID NOs: 63-65 show the A* genomic CenH3 sequence, the A* CDS sequence, and the A* protein sequence, respectively, for C003A.

E1 seeds were produced by selfing C003A E0 plant. E1 plants with A*A*bbdd genotype were grown in the greenhouse to determine its ability to induce haploids upon outcross. A wildtype plant (Tester 03S0352-22) was selected as pollen donor. E1 C003A was manually emasculated, and pollinated with the wildtype pollen. Haploids were detected by SNP markers (SEQ ID #29-43), which can tell difference between Fielder and 03S0352-22, then confirmed by flow cytometry check. In 208 F1 plants, we obtained one haploid. This showed paternal-only genotypes for four markers but maternal genotype for one marker (KW11091).

Example 7: Wheat Event A073A

Plant A073A had the genotype AA*B*bdd for TaCENH3α at the E0 seedling stage. The A073A A* allele has an adenine insertion, caused by gRNA 3, and a guanine deletion, caused by gRNA4 in the genomic DNA. This triggers a restored frameshift at the protein level, with a thirty-one amino acid difference between the wild type and edited versions in the N-terminal domain. This plant was highlighted as a potential progenitor of haploid inducer lines because of its capacity to generate offspring that were A*A*bbdd—an ideal genetic combination for triggering haploid induction. SEQ ID NOs: 69-71 show the A* genomic CenH3 sequence, the A* CDS sequence, and the A* protein sequence, respectively, for A073A.

E1 seeds were produced by allowing self-pollination of the A073A E0 plant. E1 plants were sequenced and those with the genotypic combination AA*bbdd were selected to be grown further in the greenhouse for determining haploid induction potential upon outcrossing. Using the tester line 03S0352-22 selected as the pollen donor, E1 edited plants were manually emasculated and hand pollinated. Haploids were detected by SNP markers that can distinguish Fielder and 03S0352-22 genotypically. The putative haploids, as identified by homozygousity for these markers, were then confirmed by flow cytometry check of total DNA content. Among 57 F1 plants. 53 were predominantly heterozygous for the SNP markers and were diploid by ploidy check, indicating that they were hybrids. In contrast, four had only paternal genomic SNP markers and were haploids by flow cytometry, amounting to a 7% outcross haploid induction rate.

E1 plants with AA*bbdd also led to E2 haploids during selfing (Table 3). We observed one haploid from 13 E2 plants (a 7.7% haploid induction rate). Meanwhile we observed several plants with partially chromosome elimination.

TABLE 3:

| Ploidy level of selfed E2 plants derived from A073A. | |
|---|---|
| F1 plant ID | Ploidy |
| 001-11 | 1n + X (Aneuploidy) |
| 001-13 | 1n + X (Aneuploidy) |
| 001-14 | 1n + X (Aneuploidy) |
| 001-17 | 1n + X (Aneuploidy) |
| 001-18 | 1n + X (Aneuploidy) |
| 001-19 | 2n (Diploid) |
| 001-22 | 1n + X (Aneuploidy) |
| 001-23 | 1n + X (Aneuploidy) |
| 001-24 | 2n (Diploid) |
| 001-26 | 1n + X (Aneuploidy) |
| 001-27 | 2n (Diploid) |
| 001-28 | 1n (Haploid) |
| 001-30 | 2n (Diploid) |

What is claimed is:

1. A wheat plant comprising at least an A genome, a B genome, and a D genome, wherein the B genome comprises a knock-out mutation in a CENH3α gene, and wherein the D genome comprises a knock-out mutation in a CENH3α gene, and further wherein the A genome comprises a mutated CENH3α gene comprising at least one knock-down mutation at a 5' splice site of an intron.

2. The wheat plant of claim 1, wherein the knock-down mutation is a restored frame shift mutation or a large deletion mutation.

3. The wheat plant of claim 1, wherein the wheat plant is homozygous for a knock-out mutation in a CENH3α gene in the B genome.

4. The wheat plant of claim 1, wherein the wheat plant is biallelic for a knock-out mutation in a CENH3α gene in the B genome.

5. The wheat plant of claim 1, wherein the wheat plant is homozygous for a knock-out mutation in a CENH3α gene in the D genome.

6. The wheat plant of claim 1, wherein the wheat plant is biallelic for a knock-out mutation in a CENH3α gene in the D genome.

7. The wheat plant of claim 1, wherein the wheat plant is homozygous, biallelic, or a combination thereof for a knock-out mutation in a CENH3α gene in the B genome and the D genome.

8. The wheat plant of claim 2, wherein the wheat plant is homozygous for the restored frame shift CENH3α mutation.

9. The wheat plant of claim 2, wherein the wheat plant is heterozygous for the restored frame shift CENH3α mutation.

10. The wheat plant of claim 1, wherein the wheat plant is homozygous for a knock-down mutation in a CENH3α gene of the A genome and homozygous for a knock-out mutation in a CENH3α gene in the B genome and the D genome.

11. The wheat plant of claim 10, wherein the knock-down mutation in a CENH3α gene of the A genome comprises a sequence selected from the group consisting of SEQ ID NOs: 69, 70, and 71.

* * * * *

SEQUENCE LISTING

```
<160> NUMBER OF SEQ ID NOS: 79

<210> SEQ ID NO 1
<211> LENGTH: 20
<212> TYPE: DNA
<213> ORGANISM: Triticum aestivum

<400> SEQUENCE: 1
agcgaatgaa acaacacacg                                              20

<210> SEQ ID NO 2
```

-continued

```
<211> LENGTH: 20
<212> TYPE: DNA
<213> ORGANISM: Triticum aestivum

<400> SEQUENCE: 2
gaagtcggtg acctccttga                                               20

<210> SEQ ID NO 3
<211> LENGTH: 20
<212> TYPE: DNA
<213> ORGANISM: Triticum aestivum

<400> SEQUENCE: 3
caaggaggtc accgacttct                                               20

<210> SEQ ID NO 4
<211> LENGTH: 20
<212> TYPE: DNA
<213> ORGANISM: Triticum aestivum

<400> SEQUENCE: 4
gccttgcaag ctgtatgtcc                                               20

<210> SEQ ID NO 5
<211> LENGTH: 20
<212> TYPE: DNA
<213> ORGANISM: Triticum aestivum

<400> SEQUENCE: 5
actagacgag tcgggacgaa                                               20

<210> SEQ ID NO 6
<211> LENGTH: 20
<212> TYPE: DNA
<213> ORGANISM: Triticum aestivum

<400> SEQUENCE: 6
gaagtcggtg acctccttga                                               20

<210> SEQ ID NO 7
<211> LENGTH: 20
<212> TYPE: DNA
<213> ORGANISM: Triticum aestivum

<400> SEQUENCE: 7
caaggaggtc accgacttct                                               20

<210> SEQ ID NO 8
<211> LENGTH: 18
<212> TYPE: DNA
<213> ORGANISM: Triticum aestivum

<400> SEQUENCE: 8
acgcctcgcg agctgtat                                                 18

<210> SEQ ID NO 9
<211> LENGTH: 20
<212> TYPE: DNA
<213> ORGANISM: Triticum aestivum

<400> SEQUENCE: 9
gggtccaaga aagacacacg                                               20
```

```
<210> SEQ ID NO 10
<211> LENGTH: 20
<212> TYPE: DNA
<213> ORGANISM: Triticum aestivum

<400> SEQUENCE: 10
gaagtcggtg acctccttga                                                 20

<210> SEQ ID NO 11
<211> LENGTH: 20
<212> TYPE: DNA
<213> ORGANISM: Triticum aestivum

<400> SEQUENCE: 11
caaggaggtc accgacttct                                                 20

<210> SEQ ID NO 12
<211> LENGTH: 18
<212> TYPE: DNA
<213> ORGANISM: Triticum aestivum

<400> SEQUENCE: 12
acgcctcgcg agctgtat                                                   18

<210> SEQ ID NO 13
<211> LENGTH: 17
<212> TYPE: DNA
<213> ORGANISM: Artificial sequence
<220> FEATURE:
<223> OTHER INFORMATION: primer/probe

<400> SEQUENCE: 13
ggttcaggcc aggcacg                                                    17

<210> SEQ ID NO 14
<211> LENGTH: 19
<212> TYPE: DNA
<213> ORGANISM: Artificial sequence
<220> FEATURE:
<223> OTHER INFORMATION: primer/probe

<400> SEQUENCE: 14
caaatggtgc aaacgggat                                                  19

<210> SEQ ID NO 15
<211> LENGTH: 15
<212> TYPE: DNA
<213> ORGANISM: Artificial Sequence
<220> FEATURE:
<223> OTHER INFORMATION: primer/probe

<400> SEQUENCE: 15
aggtatcaga agtcg                                                      15

<210> SEQ ID NO 16
<211> LENGTH: 30
<212> TYPE: DNA
<213> ORGANISM: Artificial Sequence
<220> FEATURE:
<223> OTHER INFORMATION: primer/probe

<400> SEQUENCE: 16
gtcgttagaa agtattgtag gtgtatcatt                                      30

<210> SEQ ID NO 17
```

<211> LENGTH: 23
<212> TYPE: DNA
<213> ORGANISM: Artificial Sequence
<220> FEATURE:
<223> OTHER INFORMATION: primer/probe

<400> SEQUENCE: 17
ctgaatgcaa aagtcgaatg atc                                              23

<210> SEQ ID NO 18
<211> LENGTH: 19
<212> TYPE: DNA
<213> ORGANISM: Artificial Sequence
<220> FEATURE:
<223> OTHER INFORMATION: primer/probe

<400> SEQUENCE: 18
tagatgtgtc ttcaaagtt                                                   19

<210> SEQ ID NO 19
<211> LENGTH: 21
<212> TYPE: DNA
<213> ORGANISM: Artificial Sequence
<220> FEATURE:
<223> OTHER INFORMATION: primer/probe

<400> SEQUENCE: 19
cgttcgactc gctggagtag t                                                21

<210> SEQ ID NO 20
<211> LENGTH: 23
<212> TYPE: DNA
<213> ORGANISM: Artificial Sequence
<220> FEATURE:
<223> OTHER INFORMATION: primer/probe

<400> SEQUENCE: 20
cctgccgatt gtttgtttta ctg                                              23

<210> SEQ ID NO 21
<211> LENGTH: 24
<212> TYPE: DNA
<213> ORGANISM: Artificial Sequence
<220> FEATURE:
<223> OTHER INFORMATION: primer/probe

<400> SEQUENCE: 21
tagtagtaac cgcgcctccc gcac                                             24

<210> SEQ ID NO 22
<211> LENGTH: 19
<212> TYPE: DNA
<213> ORGANISM: Artificial Sequence
<220> FEATURE:
<223> OTHER INFORMATION: primer/probe

<400> SEQUENCE: 22
tcgatgccgc tggtaagac                                                   19

<210> SEQ ID NO 23
<211> LENGTH: 18
<212> TYPE: DNA
<213> ORGANISM: Artificial Sequence
<220> FEATURE:
<223> OTHER INFORMATION: primer/probe

<400> SEQUENCE: 23

-continued

```
tccgatggtt gggatggt                                                18

<210> SEQ ID NO 24
<211> LENGTH: 29
<212> TYPE: DNA
<213> ORGANISM: Artificial Sequence
<220> FEATURE:
<223> OTHER INFORMATION: primer/probe

<400> SEQUENCE: 24
ctacaagctc aagctcggag agatcgtca                                    29

<210> SEQ ID NO 25
<211> LENGTH: 20
<212> TYPE: DNA
<213> ORGANISM: Artificial Sequence
<220> FEATURE:
<223> OTHER INFORMATION: sgRNA targetting exon2-intron2 junction

<400> SEQUENCE: 25
acgtcggcga caccggtgcg                                              20

<210> SEQ ID NO 26
<211> LENGTH: 20
<212> TYPE: DNA
<213> ORGANISM: Artificial Sequence
<220> FEATURE:
<223> OTHER INFORMATION: sgRNA targetting intron3-exon4 junction

<400> SEQUENCE: 26
cttgtgggag cagggggcaac                                             20

<210> SEQ ID NO 27
<211> LENGTH: 20
<212> TYPE: DNA
<213> ORGANISM: Artificial Sequence
<220> FEATURE:
<223> OTHER INFORMATION: sgRNA targetting exon1

<400> SEQUENCE: 27
gccttggtct tcctgacggc                                              20

<210> SEQ ID NO 28
<211> LENGTH: 20
<212> TYPE: DNA
<213> ORGANISM: Artificial Sequence
<220> FEATURE:
<223> OTHER INFORMATION: sgRNA targetting intron2-exon3 junction

<400> SEQUENCE: 28
gacggaatgc agaggcgagc                                              20

<210> SEQ ID NO 29
<211> LENGTH: 23
<212> TYPE: DNA
<213> ORGANISM: Artificial Sequence
<220> FEATURE:
<223> OTHER INFORMATION: primer

<400> SEQUENCE: 29
ggatcttgct ctgcctgcct gtt                                          23

<210> SEQ ID NO 30
<211> LENGTH: 26
<212> TYPE: DNA
```

```
<213> ORGANISM: Artificial Sequence
<220> FEATURE:
<223> OTHER INFORMATION: primer

<400> SEQUENCE: 30
gcagctcatt tcagttacaa acttag                                    26

<210> SEQ ID NO 31
<211> LENGTH: 26
<212> TYPE: DNA
<213> ORGANISM: Artificial Sequence
<220> FEATURE:
<223> OTHER INFORMATION: primer

<400> SEQUENCE: 31
gcagctcatt tcagttacaa acttac                                    26

<210> SEQ ID NO 32
<211> LENGTH: 25
<212> TYPE: DNA
<213> ORGANISM: Artificial Sequence
<220> FEATURE:
<223> OTHER INFORMATION: primer

<400> SEQUENCE: 32
tcggagttca ctattgcctc aggaa                                     25

<210> SEQ ID NO 33
<211> LENGTH: 23
<212> TYPE: DNA
<213> ORGANISM: Artificial Sequence
<220> FEATURE:
<223> OTHER INFORMATION: primer

<400> SEQUENCE: 33
gcccatcact tggctgatct ctt                                       23

<210> SEQ ID NO 34
<211> LENGTH: 22
<212> TYPE: DNA
<213> ORGANISM: Artificial Sequence
<220> FEATURE:
<223> OTHER INFORMATION: primer

<400> SEQUENCE: 34
cccatcactt ggctgatctc tc                                        22

<210> SEQ ID NO 35
<211> LENGTH: 27
<212> TYPE: DNA
<213> ORGANISM: Artificial Sequence
<220> FEATURE:
<223> OTHER INFORMATION: primer

<400> SEQUENCE: 35
cggaccagtt aatgtgattc gacagat                                   27

<210> SEQ ID NO 36
<211> LENGTH: 27
<212> TYPE: DNA
<213> ORGANISM: Artificial Sequence
<220> FEATURE:
<223> OTHER INFORMATION: primer

<400> SEQUENCE: 36
aaatcagcaa acccaaaatg gcatgat                                   27
```

<210> SEQ ID NO 37
<211> LENGTH: 25
<212> TYPE: DNA
<213> ORGANISM: Artificial Sequence
<220> FEATURE:
<223> OTHER INFORMATION: primer

<400> SEQUENCE: 37
atcagcaaac ccaaaatggc atgac                                        25

<210> SEQ ID NO 38
<211> LENGTH: 22
<212> TYPE: DNA
<213> ORGANISM: Artificial Sequence
<220> FEATURE:
<223> OTHER INFORMATION: primer

<400> SEQUENCE: 38
gtggttgttc tgctcggcca ct                                           22

<210> SEQ ID NO 39
<211> LENGTH: 23
<212> TYPE: DNA
<213> ORGANISM: Artificial Sequence
<220> FEATURE:
<223> OTHER INFORMATION: primer

<400> SEQUENCE: 39
cagactgaat caagtgcatc cct                                          23

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
cagactgaat caagtgcatc ccc                                          23

<210> SEQ ID NO 41
<211> LENGTH: 25
<212> TYPE: DNA
<213> ORGANISM: Artificial Sequence
<220> FEATURE:
<223> OTHER INFORMATION: primer

<400> SEQUENCE: 41
tgttttcctt ggcgctggcg atttt                                        25

<210> SEQ ID NO 42
<211> LENGTH: 21
<212> TYPE: DNA
<213> ORGANISM: Artificial Sequence
<220> FEATURE:
<223> OTHER INFORMATION: primer

<400> SEQUENCE: 42
cagagacaag aatcaggagc a                                            21

<210> SEQ ID NO 43
<211> LENGTH: 23
<212> TYPE: DNA
<213> ORGANISM: Artificial Sequence
<220> FEATURE:

```
<223> OTHER INFORMATION: primer

<400> SEQUENCE: 43
ctcagagaca agaatcagga gcg                                              23

<210> SEQ ID NO 44
<211> LENGTH: 21
<212> TYPE: DNA
<213> ORGANISM: Artificial Sequence
<220> FEATURE:
<223> OTHER INFORMATION: primer

<400> SEQUENCE: 44
gacagtggtc ccaaagatgg a                                                21

<210> SEQ ID NO 45
<211> LENGTH: 22
<212> TYPE: DNA
<213> ORGANISM: Artificial Sequence
<220> FEATURE:
<223> OTHER INFORMATION: primer

<400> SEQUENCE: 45
cgtggttgga acgtcttctt tt                                               22

<210> SEQ ID NO 46
<211> LENGTH: 21
<212> TYPE: DNA
<213> ORGANISM: Artificial Sequence
<220> FEATURE:
<223> OTHER INFORMATION: probe

<400> SEQUENCE: 46
ccccacccac gaggagcatc g                                                21

<210> SEQ ID NO 47
<211> LENGTH: 19
<212> TYPE: DNA
<213> ORGANISM: Artificial Sequence
<220> FEATURE:
<223> OTHER INFORMATION: primer

<400> SEQUENCE: 47
ccctatcccc gttgacgac                                                   19

<210> SEQ ID NO 48
<211> LENGTH: 23
<212> TYPE: DNA
<213> ORGANISM: Artificial Sequence
<220> FEATURE:
<223> OTHER INFORMATION: primer

<400> SEQUENCE: 48
ctgatagtgg tctccttgtc gct                                              23

<210> SEQ ID NO 49
<211> LENGTH: 23
<212> TYPE: DNA
<213> ORGANISM: Artificial Sequence
<220> FEATURE:
<223> OTHER INFORMATION: probe

<400> SEQUENCE: 49
ttcgccttca gcctgcacga cct                                              23
```

```
<210> SEQ ID NO 50
<211> LENGTH: 31
<212> TYPE: DNA
<213> ORGANISM: Artificial Sequence
<220> FEATURE:
<223> OTHER INFORMATION: primer

<400> SEQUENCE: 50
caaaacagat aaaacaaaat gtagggaatg t                            31

<210> SEQ ID NO 51
<211> LENGTH: 23
<212> TYPE: DNA
<213> ORGANISM: Artificial Sequence
<220> FEATURE:
<223> OTHER INFORMATION: primer

<400> SEQUENCE: 51
ggtgcaaacg ggatgagaaa gtc                                     23

<210> SEQ ID NO 52
<211> LENGTH: 17
<212> TYPE: DNA
<213> ORGANISM: Artificial Sequence
<220> FEATURE:
<223> OTHER INFORMATION: primer

<400> SEQUENCE: 52
gtaaaacgac ggccagt                                            17

<210> SEQ ID NO 53
<211> LENGTH: 17
<212> TYPE: DNA
<213> ORGANISM: Artificial Sequence
<220> FEATURE:
<223> OTHER INFORMATION: primer

<400> SEQUENCE: 53
caggaaacag ctatgac                                            17

<210> SEQ ID NO 54
<211> LENGTH: 15
<212> TYPE: DNA
<213> ORGANISM: Artificial Sequence
<220> FEATURE:
<223> OTHER INFORMATION: primer

<400> SEQUENCE: 54
tggcccgcac caagc                                              15

<210> SEQ ID NO 55
<211> LENGTH: 23
<212> TYPE: DNA
<213> ORGANISM: Artificial Sequence
<220> FEATURE:
<223> OTHER INFORMATION: primer

<400> SEQUENCE: 55
gctgtatgtc cttttgcatg acg                                     23

<210> SEQ ID NO 56
<211> LENGTH: 4401
<212> TYPE: DNA
<213> ORGANISM: Triticum aestivum

<400> SEQUENCE: 56
```

-continued

| | |
|---|---|
| atggcccgca ccaagcaccc ggccgtcagg aagaccaagg cgccgcccaa gaagcagctc | 60 |
| gggccccgcc ccgcgcagcg gcggcaggag acaggtcagc ccttccctcc ttcctccccc | 120 |
| cgtctcccgc ctctcgagcg aacgccgtcg ccatttcgtc gcgagagatg gacggacgga | 180 |
| cgccccacgc atgacgctaa tgtgctcttc ctctcccttt gcagatggcg cgggcacgtc | 240 |
| ggcgacaccg gtagcgcggg accttcccgg gtcgcttcct tttcgtttcg tcttgttttc | 300 |
| tgttttttgg tctgacttgc tcgtcacctg ttcgacggaa tgcagaggcg agccgggcgg | 360 |
| gcggcggccc caggggggc tcaaggtgcg gccttctttg cgcttttcgg ttttccgccg | 420 |
| cgtgtttagg gccatttccg tcttgtttgg gggtgcgcgg ggcgggggct tgttttttt | 480 |
| cctccccct tcgttgttgc gcacattgct cgggaatgct gccaggagcg gttgcggttc | 540 |
| ttctttgacc cttcgggagg gctggatcgg cagtttcttc gcttccttgc tccagatttt | 600 |
| agttcatctt gtaccagtac agtagcaaga tgatggatgg gggcttgttt tttctttctc | 660 |
| cttccttgtt ccggacattt ctctggagcg acttttatgc atttcccagt attgtccttt | 720 |
| gtccttagag ggtagtggat cggcagtttt cttcgcctca ttggtccaga ttttagttta | 780 |
| tcttgtacgg taccaagatg atggatgtgg cacaaagttc tcagtttggg ggttgcgctc | 840 |
| ttccgggcag ttgttatttt ggtctgtgat gactaactcg tatctattct tgtgggagca | 900 |
| ggggcaaaact gggcaaccca agcagaggaa accacaccgg ttcaggccag gcacggtggc | 960 |
| actgcgggag atcaggaggt atcagaagtc ggtcgacttt ctcatcccgt ttgcaccatt | 1020 |
| tgtccgtctg gtgggtacct ctgtctgtca tatcctctcg ctctctctac aaacgatctg | 1080 |
| cagtgcagag tgtaattgga atattttgtt cctgacaaat ttgcagatca aggaggtcac | 1140 |
| cgacttcttc tgtcctgaaa tcagccgctg gactccccaa gcgctcgtcg cgattcaaga | 1200 |
| ggtcagtgct aaaacctggc atgtactatt agatctgatg gtttgattag agtactacaa | 1260 |
| tgcagatgaa ttcaatatcc gaaaaccatg aactgtgggg tagatacatg tatcgcctta | 1320 |
| attcatggtt tctgaatgct ctgctattaa ttcagtttga tatatttatt tagcagcatg | 1380 |
| gtattgtttt ggtggctggt aaatcaaaac tgaaatgtga ttacgagcaa aacggtatcg | 1440 |
| attgtcgatc ctgtgtgttt ttgtgcacat ctggttgttt ggtcaagatg tgtttgtgca | 1500 |
| catcttgcaa catgatcctg cccacacact caaaactgac tattggttag gttccatttg | 1560 |
| tcttatggaa tttagggtgt aactgagagg tgagcaagtg gtagtaacgt tcaattttga | 1620 |
| ttcaggatga ggatattgtg atccagaaaa ttgcatgtta tggttatgtg tccaaacgcc | 1680 |
| aaatgattat gtctatatcc agtactttag aaccagtaca acaacaaaaa gtactttaga | 1740 |
| accagtcaag tttattgtgc atttatacaa gagtgttgtt tgcacaatag acttgcttta | 1800 |
| gtcgtctctt gccagaaatg ccttcttctg cacaacgagc aaaaataaca taagttgac | 1860 |
| tatactcagt gtggcctaag aaatgagttg tacttttag tcactggcct gtgtatttgc | 1920 |
| tttgaattga cacataattc ccttttcctt tccctctgca ggctgcagag tatcacctcg | 1980 |
| tcgacgtatt tgaaagggca aatcactgtg ccatccatgc aaagcgtgtt accgtcagta | 2040 |
| agttctcact gaatgaaaac tccctttctt ttacaatatt gcgcagaagg aaacatgcca | 2100 |
| gttatgaaag agtttcaatt acaggatcac ctttgctttc atttgatgtg atatctagtt | 2160 |
| ttgatgttgt ttcaaggttc aagaattcta atgataaatg ataggatcca caattgttat | 2220 |
| atctctgcag ctcctcgtat ctgttgtcca cgaacaaaca tatcaaacaa ttcattaaaa | 2280 |
| agatgaagaa gtcaaacaaa cagtatatgt gcactgcata ttagatatca aacctggtta | 2340 |
| ctatacgact gatctggcct gacccccgcg tcgcctctcc ctggcggcac gggggggaacc | 2400 |

```
actccggcgc cgccaccttc cctcctccct ccacccccca cctcgccgcc gcctgaggag    2460
ttcgccggcg aagcccggtc tggctccagg gagggtggcg gcggggcatc tctctgcgag    2520
gcgtgagggc gcatctcgtg cgcgggcgcg gcgagcttgg gcgggatcgc gggcgcggct    2580
ctggctcggg ctggtgaggc tccggcggtc cgaggggtgt cgcggcgcgg cgggggtctc    2640
gctccggcgc gggcggtccg agggcgcgcg ggatctggcg ctccagcagg ggcgccgtca    2700
aggggagccg gcagggaag ctcgtcaggc gggctcgtca ggcaggcgtg acgcggggcg    2760
gcggccgcgg gctggaagcc atggcgtttt ggccatggtg tcgtgtgcgc tcgcttctca    2820
ttcgcagctt gaggtgctgc tgctgagggt ggtgcgcggt gaagcttggt ggtcggcgtt    2880
ggagagtgca aggcgcaaca ggaatggctc caatgatctc cacgcttctg ggtggatcag    2940
atctgcggcc ctccataggg gtgtgttccg ggcgaaagcc ttgacccgac tttgtcggtg    3000
ccgtcgacgg cggcgctttc gggcgtcgtt tccctccttg gaggcgtcgt tgtggaactc    3060
atcttcttct atgtggggct cgggctctcc gggtgaaaac ctaagctcca gattttccgg    3120
agcgggcgat ggcggcgtct tcgtcgtttc cctcttgggg gcgttgcttg ggagagttag    3180
cttgtgcttg gtgcgtttgg ttttctccta cgtcgggttt ggtggatgcc ggggcagcgg    3240
ccccggacgg ctgatgaacg ccgaggcggc ggcctcggaa agtgatgcgc ggtgcggctc    3300
catggggcgg ggcggtggct cggccttcac ttgggtggca atcttgggcc acttgggtgg    3360
caggcttgtc ggtccggtcg acgcgttcca gaggggcgg tctgactttg cgtcggggcg    3420
gcggccccgg atgtggtgcg acgttcgtgg tctgcgagcg gttgccttga gcagcgtggg    3480
ctgcgggcag ctgggtcgcg cggcgttgct gctcgagcgg agcggtggta cgtcggggcg    3540
gcggccccgg aaggtgatgc cggttgattg cgctgggcgt gacggagcgg tggatgtcgg    3600
ggcggcggcc ccgagaaaat cactgtggcg tccagatttc tgtggcaacg atgatggtgg    3660
gagcgatgtc ggcgacgcgg caatggttgc gatagtcggc tcttctccgg cgtgtccacg    3720
atattgcctc ggtttgtttg ttgctgtgga gtcgaagctg cggcggcgag gccctgtggt    3780
atacgatgac tggttccagg tgtcctttcg tcgatcttcc gtggcgccag ccgtgcctgg    3840
tttcgttctt ccgagttctc cgtcagaatc ggagctgcgt tgtctgtccg caggtcgaca    3900
tgttgtcgag aagggtgggc tttgccctgt gtgtttcagt ctatgcgagt gggctcggcc    3960
cttgttgttc tggttttgc ccggttttcc gtaattaact gggcaattct cttctgctta    4020
attaatagat gaggcaatct ttgcctccct ttcaaaaaaa aacctggtta ctatagcagg    4080
aaattcaggg ttgattactt tatttcttat ctgaaggata acattgtat caaatcagaa    4140 ttttatttgt aagttacatt ttttttact tataaaactt ggaaactgtt ttactgtgac    4200
aaatagatgc cactagaatc atgatcacat cgtggctgtt gctattctaa caaataaatg    4260
ctcctgaaca aatgggaact atatatgaag atgtatggac cagcatgttc ctgttaacct    4320 gaccttttc cttttttgc tgctgcagtg caaaaggaca tacagcttgc aaggcgtatc    4380
ggcgggagga ggctttggtg a                                                4401
```

<210> SEQ ID NO 57
<211> LENGTH: 588
<212> TYPE: DNA
<213> ORGANISM: Triticum aestivum

<400> SEQUENCE: 57

```
atggcccgca ccaagcaccc ggccgtcagg aagaccaagg cgccgcccaa gaagcagctc     60
```

```
gggccccgcc ccgcgcagcg gcggcaggag acagatggcg cgggcacgtc ggcgacaccg    120
gtagcgcggg accttcccgg gtcgcttcct tttcgtttcg tcttgttttc tgtttttgg    180 tctgacttgc tcgtcacctg ttcgacggaa tgcagaggcg agccgggcgg gcggcggccc    240 caggggggc tcaaggggca aactgggcaa cccaagcaga ggaaaccaca ccggttcagg    300
ccaggcacgg tggcactgcg ggagatcagg aggtatcaga agtcggtcga ctttctcatc    360
ccgtttgcac catttgtccg tctgatcaag gaggtcaccg acttcttctg tcctgaaatc    420
agccgctgga ctccccaagc gctcgtcgcg attcaagagg ctgcagagta tcacctcgtc    480
gacgtatttg aaagggcaaa tcactgtgcc atccatgcaa agcgtgttac cgtcatgcaa    540
aaggacatac agcttgcaag gcgtatcggc gggaggaggc tttggtga              588

<210> SEQ ID NO 58
<211> LENGTH: 493
<212> TYPE: DNA
<213> ORGANISM: Triticum aestivum

<400> SEQUENCE: 58
atggcccgca ccaagcaccc ggccgtcagg aagaccaagg cgccgcccaa gaagcagctc     60
gggccccgcc ccgcgcagcg gcggcaggag acagatggcg cgggcacgtc ggcgacaccg    120
aggcgagccg gcgggcggc ggccccaggg ggggctcaag gggcaaactg gcaacccaa    180 gcagaggaaa ccacaccggt tcaggccagg cacgtggca ctgcgggaga tcaggaggta    240
tcagaagtcg gtcgactttc tcatcccgtt tgcaccattt gtccgtctga tcaaggaggt    300
caccgacttc ttctgtcctg aaatcagccg ctggactccc caagcgctcg tcgcgattca    360
agaggctgca gagtatcacc tcgtcgacgt atttgaaagg gcaaatcact gtgccatcca    420
tgcaaagcgt gttaccgtca tgcaaaagga catacagctt gcaaggcgta tcggcgggag    480
gaggctttgg tga                                                     493

<210> SEQ ID NO 59
<211> LENGTH: 195
<212> TYPE: PRT
<213> ORGANISM: Triticum aestivum

<400> SEQUENCE: 59

Met Ala Arg Thr Lys His Pro Ala Val Arg Lys Thr Lys Ala Pro Pro
1               5                   10                  15

Lys Lys Gln Leu Gly Pro Arg Pro Ala Gln Arg Arg Gln Glu Thr Asp
            20                  25                  30

Gly Ala Gly Thr Ser Ala Thr Pro Val Ala Arg Asp Leu Pro Gly Ser
        35                  40                  45

Leu Pro Phe Arg Phe Val Leu Phe Ser Val Phe Trp Ser Asp Leu Leu
    50                  55                  60

Val Thr Cys Ser Thr Glu Cys Arg Gly Glu Pro Gly Gly Arg Pro
65                  70                  75                  80

Gln Gly Gly Leu Lys Gly Gln Thr Gly Gln Pro Lys Gln Arg Lys Pro
                85                  90                  95

His Arg Phe Arg Pro Gly Thr Val Ala Leu Arg Glu Ile Arg Arg Tyr
            100                 105                 110

Gln Lys Ser Val Asp Phe Leu Ile Pro Phe Ala Pro Phe Val Arg Leu
        115                 120                 125

Ile Lys Glu Val Thr Asp Phe Cys Pro Glu Ile Ser Arg Trp Thr
    130                 135                 140
```

Pro Gln Ala Leu Val Ala Ile Gln Glu Ala Ala Glu Tyr His Leu Val
145                 150                 155                 160

Asp Val Phe Glu Arg Ala Asn His Cys Ala Ile His Ala Lys Arg Val
            165                 170                 175

Thr Val Met Gln Lys Asp Ile Gln Leu Ala Arg Arg Ile Gly Gly Arg
        180                 185                 190

Arg Leu Trp
        195

<210> SEQ ID NO 60
<211> LENGTH: 106
<212> TYPE: PRT
<213> ORGANISM: Triticum aestivum

<400> SEQUENCE: 60

Met Ala Arg Thr Lys His Pro Ala Val Arg Thr Lys Ala Pro Pro
1               5                   10                  15

Lys Lys Gln Leu Gly Pro Arg Pro Ala Gln Arg Gln Glu Thr Asp
            20                  25                  30

Gly Ala Gly Thr Ser Ala Thr Pro Arg Arg Ala Gly Arg Ala Ala Ala
        35                  40                  45

Pro Gly Gly Ala Gln Gly Ala Asn Trp Ala Thr Gln Ala Glu Glu Thr
    50                  55                  60

Thr Pro Val Gln Ala Arg His Gly Gly Thr Ala Gly Asp Gln Glu Val
65                  70                  75                  80

Ser Glu Val Gly Arg Leu Ser His Pro Val Cys Thr Ile Cys Pro Ser
                85                  90                  95

Asp Gln Gly Gly His Arg Leu Leu Leu Ser
            100                 105

<210> SEQ ID NO 61
<211> LENGTH: 2618
<212> TYPE: DNA
<213> ORGANISM: Triticum aestivum

<400> SEQUENCE: 61
atggcccgca ccaagcaccc ggccgtcagg aagaccaagg cgctgcccaa gaagcagctc      60
gggacgcgcc cctcggccgg gacgccgcgg cggcaggaga caggtgagcc cgcccctcct     120
tccttcctcc ccccatctc gagcgaacgc cgtcgcctcg tcgcgagaga tggacgcccc     180
acgcgtgatg ctaatgtgtt cttcctctcc ctttgcagat ggcgcgggca cgtcggcgac     240
tccggtgcgc gggccttcct gggtcacttc cttttgtttc gtcttgtttt ctgttttgg     300 tctgacttgc tcgtctcctg ttcgacggaa tgcagaggcg agccgggcgg gcggcggccc     360
caggggcggc tgaaggtgcg cccttctttg tgcttttcgg ttttccgccg cgtgtttagg     420
gctatttccg tcttgtttgg ggcgggggact tgtatcttct cccccttcg ttgttgcgca     480 catttctcgg gaatgctacc aggagcagtt gcggttcttt gcccttagg gagggctgca     540 ccggcaattt cttcgcttcc ttgctccaga ttttagttta tcttctacag tagcaagatg     600
atggatgggg acttgcgttt ttcttttccc ttccttgttc cgggcatttc tctggagcaa     660
tgtttatgca tttcccagta ttgtcctttg ccctcagagg ggaggggatc ggcagttttc     720
ttcgcttcat cggtccagat tttagtttat cttgtacagt agcaagatga tggatgtgac     780
acaaagttct cagtttgggg gttgcgctct tccgggtagt tgttaatttc gtctgtgact     840
gactcgtatc tattcttgtg ggagcagggg caactgggca acccaagcag aggaagccac     900

-continued

| | |
|---|---|
| accggttcag gccaggcacg gtggcactgc gggagatcag gaagtaccag aaatcggtcg | 960 |
| actttctcat cccgtttgca ccatttgttc gtctggtggg tacctctgtc atatcctctc | 1020 |
| gctctctcta ccaacgatct ggagtgcgga gtgtaaattg gaatcttttg ttcctgacaa | 1080 |
| atttgtagat caaggaggtc accgacttct tctgtcctga atcagccgc tggactcccc | 1140 |
| aagcgctcgt tgcaattcaa gaggtcagtg ctcaaacctg gcatgtacta ttagatctga | 1200 |
| tggtttgatt agagtactac aatgcagatg aattcaagat ctgaaaacca tgaactgtgg | 1260 |
| ggtagatgca tgtatcatag tgtctgaatg ctctggtatt aattcagttt gatatattta | 1320 |
| tttagcagca tggtattgtt ttggtggctg gtaacccaaa actgaaacgt gattacgagc | 1380 |
| aaaatggtat caattgtctt ttctgtgtgt ttgtgcaaat ctggttgttt ggtcaagata | 1440 |
| tacagtcttg caacatgaat acatgatcct gcccacacac tcaaaactga actattggtt | 1500 |
| agatgccata tgtcttatgg aatttagggt gtaactgaga ggtgagcaag tggtagtgac | 1560 |
| gttcaatttt gattcaggat gaggatattg tgatccagaa aattgcatgt tatggttatg | 1620 |
| tgtccgaacg ccaaatgatt atgtctatat ccactacatg cttatgtgtc caacccccca | 1680 |
| aatgattatc tctgtttcca gtacaacaac aaaaagtact ttagaaccag tcaagtttat | 1740 |
| tgtgcattta tacgagattg ttgtttgcac aatagactta ctttagtcgc ctcttgccag | 1800 |
| aaatgccttc ttctgcacaa cgagcaaaaa taacataaag ttgactatac tcagtgtggc | 1860 |
| ctaagaaatg agttagtact tttagtcact ggcctgtgta tttgctttga attgacgcat | 1920 |
| aattcccttt tcctttccct ctgcaggctg cagagtatca cctcgtcgac gtatttgaaa | 1980 |
| gggcaaatca ctgtgccatc catgcaaagc gtgttaccgt cagtaagttc tcactgaatg | 2040 |
| aaaacttcct tccatttaca atattatgca gaaggaaaca tgccagttat gaaagagttt | 2100 |
| caattacagg atcaccttg ctttcatttg atgtgatatc tagttttgat gttgtttcaa | 2160 |
| ggttcaagaa ttctaacgat taatgatagg atccacaatt gttatatctc tgcagctcct | 2220 |
| cgtatctgtt gtcaacgaac aaacatgtca acaattcat taaaaaaaac gaagatgtca | 2280 |
| aaccgggtta ctatagcagg aaattcaggg ttgattacct atttattcag ggttgattac | 2340 |
| ctatttattt cttatctgaa ggataaacat tatataaaat cagaattta tttgtaggtt | 2400 |
| acatttttg tttccttata aaacttggaa actgttgaga atcatcatca tcatggctgt | 2460 |
| tgctattcta acaaataaaa cggatgctcc tgaataaatg gaactatata tgaagatgta | 2520 |
| tttactagca tgttcctgtt aacctgactt tttttgctgc tacagtgcaa aaggacatac | 2580 |
| agctcgcgag gcgtatcggc gggaggaggc tttggtga | 2618 |

<210> SEQ ID NO 62
<211> LENGTH: 2676
<212> TYPE: DNA
<213> ORGANISM: Triticum aestivum

<400> SEQUENCE: 62

| | |
|---|---|
| atggcccgta ccaagcaccc ggccgtcagg aagaccaagg cgccgcccaa gaagcagctc | 60 |
| gggccccgtc ccgcgcagcg gcggcaggag acaggtcagc ccgcccgccc gtcgctcctc | 120 |
| ccttccttcc ccccccgtc tcccgcctct cgaccgaacg ccgccgcctt gtttgttgcg | 180 |
| gtacagaggt gcccgtccgt gatgctaaca ggttcttcct ctcctttgca gatggcgcgg | 240 |
| gcacgtcggc gacaccggtg gcggggtctt cccgggtcgc ttccttttgt ttcgtcttgt | 300 |
| tttctgtttt ttggtctgac ttgctcgtca cctgttcgac ggaatgcaga ggcgagccgg | 360 |
| gcgggcggcg gccccagggg gcgctgaagg tgcggccttc tttgcgcttt tcggttttcc | 420 |

-continued

```
gccgcgtgtt tagggccatt tccgtcttgt ttgggggtgg gtggggcggg ggcttgattt      480
ttttcctcct cccttcgttg ttgcgcacat ttctcgggaa tgcttccagg agcggttgca      540
gttcttcttt ggccttaggg agggctggat cggcagtttc ttcgcttcct tgctccagat      600
tttagtttat cttgtagtag tacagtagca agatgatgga tggggacttg tttttcttt       660 cccttcctt gttccggaca tttctttgga gcaacttta tgcatttccc ggtattgtcc       720 tttgcccta gagtggagtg gatcggcagt tttcttcgct tccctggtcc agattttagt      780
ttatctttac agtagcaaga tgatgtatgt gacacaaagt tctcagtttg ggggttgcgc      840
tcttccaggt gtagttgtta ttttcgtct gtgactgact cgtatctatt cttgtgggag      900
caggggcaaa ctgggcaacc caagcagagg aagccacacc ggttcaggcc aggcacggtg      960
gcactgcggg agatcaggag gtaccagaag tcggtcgact ttctcatccc gtttgcacca     1020
tttgtccgtc tggtgggtac ctctgtctgt catatcctct cgctctctct accaacaatc     1080
tggagtgcgg ggtgtaaact ggaatctttt gttcctgaca aatttgcaga tcaaggaggt     1140
caccgacttc ttctgtcctg aaatcagccg ctggactccc caagcgctcg tcgcgattca     1200
agaggtcagt gctcaaacct ggcatgtact attagatctg atggtttgat tagagtacta     1260
caatgcagat gaattcaaga tctgaaaacc atgaactgtg gggtagatgc atgtatcgcc     1320
ttaattcata gttctgaat gctctggtat taattcagtt tgatatattt atttagctgc      1380
atggtattgt tttggtggct ggtaattcaa aactgaaatg tgattacgag caaaatggta     1440
tcaattgtct tttctgtgca catctggttg tttggtcaag atatacagtc ttgcaacatg     1500
atcctgccca cacactcaaa actgaactat tggttagatt ccattttgct tatggaattt     1560
agggtgtaac tgagaggtga gcaggtggca gtgaccagag ctacgttcaa ttttgattca     1620
ggaagaggat cttgcgatcc agaaaattgc atgttatggt tatgtgtccg aaggccaaat     1680
gattatctct atatccagta catgcttatg tgtccgaacc cccaaatgat tatctctata     1740
tccagtacat gcttatgtgt ccgaaccatt caagttattg tgcatttatt caagattgtt     1800
gtttgcacaa tagacttact ttagtcgcct cttgccagaa atgcctcctt ctgcacaatg     1860
agcaaaaata acataaagtt gattatgctc agtgtggcct aattgtactt tcagttactg     1920
gcctgtgtat ttgctttgaa ttgacacata attcccttt cctttccctc tgcaggctgc     1980
agagtatcac ctcgtcgacg tatttgaaag ggcaaatcac tgtgccatcc atgcaaagcg     2040
tgttaccgtc agtaagttct cactgaatga aaacttcctt tcttttacaa tattatgcag     2100
aaggaaacat gccagttatg aaagagtttc aattacaaga tcacctttgc tttcatttga     2160
tgtggtatct agttttgatg ttgtttcaag gttcaagaat tctaatgatt aatgatagga     2220
tccacaattg ttatatctct gcagctcctc gtatctgacg aacaaacatg tcaaacaatt     2280
cattaaaaaa tgaagatgtc aaacaaacag tatatgcact gcatattgga tatcaaacct     2340
ggttactaca gcaggaagtt cagggttgat tactttattt cttatctgaa ggataaacat     2400
tgtatcaaat cagaatttta tttgtaagtt gcattttttg tttactcata aaacttggaa     2460
actgttttac tgtgagaaat agatgcccac tagaatcatg atcatcatca tggctgttgc     2520
tattctaaca aataaaacgg atgctcctga acaaatggaa ctatgtatga agatgtatgg     2580
actagcatgt tcctgttaac ctgactttt tttgctgcta cagtgcaaaa ggacatacag     2640
ctcgcgaggc gtatcggtgg gaggaggctt tggtga                              2676
```

<210> SEQ ID NO 63

<211> LENGTH: 4399
<212> TYPE: DNA
<213> ORGANISM: Triticum aestivum

<400> SEQUENCE: 63

```
atggcccgca ccaagcaccc ggccgtcagg aagaccaagg cgccgcccaa gaagcagctc      60
gggccccgcc ccgcgcagcg gcggcaggag acaggtcagc ccttccctcc ttcctcccccc    120
cgtctcccgc ctctcgagcg aacgccgtcg ccatttcgtc gcgagagatg gacgacgga     180
cgccccacgc atgacgctaa tgtgctcttc ctctcccttt gcagatggcg cgggcacgtc    240
ggcgacaccg tgcgcgggac cttcccgggt cgcttccttt cgtttcgtc ttgttttctg     300
ttttttggtc tgacttgctc gtcacctgtt cgacggaatg cagaggcgag ccgggcgggc    360
ggcggcccca gggggggctc aaggtgcggc cttctttgcg cttttcggtt ttccgccgcg    420
tgtttagggc catttccgtc ttgtttgggg gtgcgcgggg cggggcttg tttttttcc      480
tcccccttc gttgttgcgc acattgctcg ggaatgctgc caggagcggt tgcggttctt     540
ctttgacct tcgggagggc tggatcggca gtttcttcgc ttccttgctc cagattttag    600
ttcatcttgt accagtacag tagcaagatg atggatgggg gcttgttttt tctttctcct   660
tccttgttcc ggacatttct ctggagcgac ttttatgcat ttcccagtat tgtcctttgt    720
ccttagaggg tagtggatcg gcagttttct tcgcctcatt ggtccagatt ttagtttatc   780
ttgtacggta ccaagatgat ggatgtggca caaagtctc agtttggggg ttgcgctctt    840
ccgggcagtt gttatttggg tctgtgatga ctaactcgta tctattcttg tgggagcagg    900
ggcaaactgg gcaacccaag cagaggaaac cacaccggtt caggccaggc acggtggcac    960
tgcgggagat caggaggtat cagaagtcgg tcgactttct catcccgttt gcaccatttg   1020
tccgtctggt gggtacctct gtctgtcata tcctctcgct ctctctacaa cgatctgca    1080
gtgcagagtg taattggaat attttgttcc tgacaaattt gcagatcaag gaggtcaccg   1140
acttcttctg tcctgaaatc agccgctgga ctcccccaagc gctcgtcgcg attcaagagg   1200
tcagtgctaa aacctggcat gtactattag atctgatggt ttgattagag tactacaatg   1260
cagatgaatt caatatccga aaaccatgaa ctgtggggta gatacatgta tcgccttaat   1320
tcatggtttc tgaatgctct gctattaatt cagtttgata tatttattta gcagcatggt   1380
attgttttgg tggctggtaa atcaaaactg aaatgtgatt acgagcaaaa cggtatcgat   1440
tgtcgatcct gtgtgttttt gtgcacatct ggttgtttgg tcaagatgtg tttgtgcaca   1500
tcttgcaaca tgatcctgcc cacacactca aaactgacta ttggttaggt tccatttgtc   1560
ttatggaatt tagggtgtaa ctgagaggtg agcaagtggt agtaacgttc aattttgatt   1620
caggatgagg atattgtgat ccagaaaatt gcatgttatg gttatgtgtc caaacgccaa   1680
atgattatgt ctatatccag tactttagaa ccagtacaac aacaaaaagt actttagaac   1740
cagtcaagtt tattgtgcat ttatacaaga gtgttgtttg cacaatagac ttgctttagt   1800
cgtctcttgc cagaaatgcc ttcttctgca caacgagcaa aaataacata agttgacta   1860
tactcagtgt ggcctaagaa atgagttgta ctttttagtc actggcctgt gtatttgctt   1920
tgaattgaca cataattccc ttttcctttc cctctgcagg ctgcagagta tcacctcgtc   1980
gacgtatttg aaagggcaaa tcactgtgcc atccatgcaa agcgtgttac cgtcagtaag   2040
ttctcactga atgaaaactc cctttctttt acaatattgc gcagaaggaa acatgccagt   2100
tatgaaagag tttcaattac aggatcacct ttgctttcat ttgatgtgat atctagtttt   2160
gatgttgttt caaggttcaa gaattctaat gataaatgat aggatccaca attgttatat   2220
```

```
ctctgcagct cctcgtatct gttgtccacg aacaaacata tcaaacaatt cattaaaaag    2280
atgaagaagt caaacaaaca gtatatgtgc actgcatatt agatatcaaa cctggttact    2340
atacgactga tctggcctga cccccgcgtc gcctctccct ggcggcacgg ggggaaccac    2400
tccggcgccg ccaccttccc tcctccctcc acccccacc tcgccgccgc ctgaggagtt    2460
cgccggcgaa gcccggtctg gctccaggga gggtggcggc ggggcatctc tctgcgaggc    2520
gtgagggcgc atctcgtgcg cgggcgcggc gagcttgggc gggatcgcgg gcgcggctct    2580
ggctcgggct ggtgaggctc cggcggtccg aggggtgtcg cggcgcggcg gggtctcgc    2640 tccggcgcgg gcggtccgag ggcgcgcggg atctggcgct ccagcagggg cgccgtcaag    2700
gggagccggg cagggaagct cgtcaggcgg gctcgtcagg caggcgtgac gcggggcggc    2760
ggccgcgggc tggaagccat ggcgttttgg ccatggtgtc gtgtgcgctc gcttctcatt    2820
cgcagcttga ggtgctgctg ctgagggtgg tgcgcggtga agcttggtgg tcggcgttgg    2880
agagtgcaag gcgcaacagg aatggctcca atgatctcca cgcttctggg tggatcagat    2940
ctgcggccct ccataggggt gtgttccggg cgaaagcctt gacccgactt tgtcggtgcc    3000
gtcgacggcg gcgctttcgg gcgtcgtttc cctccttgga ggcgtcgttg tggaactcat    3060
cttcttctat gtggggctcg ggctctccgg gtgaaaacct aagctccaga ttttccggag    3120
cgggcgatgg cggcgtcttc gtcgtttccc tcttgggggc gttgcttggg agagttagct    3180
tgtgcttggt gcgtttggtt ttctcctacg tcggqttttgg tggatgccgg ggcagcggcc    3240
ccggacggcg gatgaacgcc gaggcggcgg cctcggaaag tgatgcgcgg tgcggctcca    3300
tggggcgggg cggtggctcg gccttcactt gggtggcaat cttgggccac ttgggtggca    3360
ggcttgtcgg tccggtcgac gcgttccaga ggggcggtc tgactttgcg tcggggcggc    3420
ggccccggat gtggtgcgac gttcgtggtc tgcgagcggt gccttgagc agcgtgggct    3480 gcgggcagct gggtcgcgcg gcgttgctgc tcgagcggag cggtggtacg tcggggcggc    3540
ggccccggaa ggtgatgccg gttgattgcg ctgggcgtga cggagcggtg gatgtcgggg    3600
cggcggcccc gagaaaatca ctgtggcgtc cagatttctg tggcaacgat gatggtggga    3660
gcgatgtcgg cgacgcggca atggttgcga tagtcggctc ttctccggcg tgtccacgat    3720
attgcctcgg tttgtttgtt gctgtggagt cgaagctgcg gcggcgaggc cctgtggtat    3780
acgatgactg gttccaggtg tcctttcgtc gatcttccgt ggcgcagcc gtgcctggtt    3840 tcgttcttcc gagttctccg tcagaatcgg agctgcgttg tctgtccgca ggtcgacatg    3900
ttgtcgagaa gggtgggctt tgccctgtgt gtttcagtct atgcgagtgg gctcggccct    3960
tgttgttctg gttttgccc ggttttccgt aattaactgg gcaattctct tctgcttaat    4020
taatagatga ggcaatcttt gcctcccttt caaaaaaaaa cctggttact atagcaggaa    4080
attcagggtt gattacttta tttcttatct gaaggataaa cattgtatca aatcagaatt    4140
ttatttgtaa gttacatttt tttttactta taaaacttgg aaactgtttt actgtgacaa    4200
atagatgcca ctagaatcat gatcacatcg tggctgttgc tattctaaca aataaatgct    4260
cctgaacaaa tgggaactat atatgaagat gtatggacca gcatgttcct gttaacctga    4320 ccttttcct tttttgctg ctgcagtgca aaggacata cagcttgcaa ggcgtatcgg    4380
cgggaggagg ctttggtga                                                 4399
```

<210> SEQ ID NO 64
<211> LENGTH: 492
<212> TYPE: DNA

<213> ORGANISM: Triticum aestivum

<400> SEQUENCE: 64

| | |
|---|---|
| atggcccgca ccaagcaccc ggccgtcagg aagaccaagg cgccgcccaa gaagcagctc | 60 |
| gggccccgcc ccgcgcagcg gcggcaggag acagatggcg cgggcacgtc ggcgacacca | 120 |
| ggcgagccgg gcgggcggcg gccccagggg gggctcaagg ggcaaactgg caacccaag | 180 |
| cagaggaaac acaccggtt caggccaggc acggtggcac tgcgggagat cagaggtat | 240 |
| cagaagtcgg tcgactttct catcccgttt gcaccatttg tccgtctgat caaggaggtc | 300 |
| accgacttct tctgtcctga atcagccgc tggactcccc aagcgctcgt cgcgattcaa | 360 |
| gaggctgcag agtatcacct cgtcgacgta tttgaaaggg caaatcactg tgccatccat | 420 |
| gcaaagcgtg ttaccgtcat gcaaaaggac atacagcttg caaggcgtat cggcgggagg | 480 |
| aggctttggt ga | 492 |

<210> SEQ ID NO 65
<211> LENGTH: 163
<212> TYPE: PRT
<213> ORGANISM: Triticum aestivum

<400> SEQUENCE: 65

Met Ala Arg Thr Lys His Pro Ala Val Arg Lys Thr Lys Ala Pro Pro
1               5                   10                  15

Lys Lys Gln Leu Gly Pro Arg Pro Ala Gln Arg Arg Gln Glu Thr Asp
            20                  25                  30

Gly Ala Gly Thr Ser Ala Thr Pro Gly Glu Pro Gly Gly Arg Arg Pro
        35                  40                  45

Gln Gly Gly Leu Lys Gly Gln Thr Gly Gln Pro Lys Gln Arg Lys Pro
    50                  55                  60

His Arg Phe Arg Pro Gly Thr Val Ala Leu Arg Glu Ile Arg Arg Tyr
65                  70                  75                  80

Gln Lys Ser Val Asp Phe Leu Ile Pro Phe Ala Pro Phe Val Arg Leu
                85                  90                  95

Ile Lys Glu Val Thr Asp Phe Phe Cys Pro Glu Ile Ser Arg Trp Thr
            100                 105                 110

Pro Gln Ala Leu Val Ala Ile Gln Glu Ala Ala Glu Tyr His Leu Val
        115                 120                 125

Asp Val Phe Glu Arg Ala Asn His Cys Ala Ile His Ala Lys Arg Val
    130                 135                 140

Thr Val Met Gln Lys Asp Ile Gln Leu Ala Arg Arg Ile Gly Gly Arg
145                 150                 155                 160

Arg Leu Trp

<210> SEQ ID NO 66
<211> LENGTH: 2619
<212> TYPE: DNA
<213> ORGANISM: Triticum aestivum

<400> SEQUENCE: 66

| | |
|---|---|
| atggcccgca ccaagcaccc ggccgtcagg aagaccaagg cgctgcccaa gaagcagctc | 60 |
| gggacgcgcc cctcggccgg gacgccgcgg cggcaggaga caggtgagcc cgcccctcct | 120 |
| tccttcctcc cccccatctc gagcgaacgc cgtcgcctcg tcgcgagaga tggacgcccc | 180 |
| acgcgtgatg ctaatgtgtt cttcctctcc ctttgcagat ggcgcgggca cgtcggcgac | 240 |
| tccggtgcgc gggccttcct gggtcacttc cttttgtttc gtcttgtttt ctgttttttgg | 300 |

```
tctgacttgc tcgtctcctg ttcgacggaa tgcagaggcg agccgggcgg cggcggccc      360 cagggggcggc tgaaggtgcg cccttctttg tgcttttcgg ttttccgccg cgtgtttagg     420
gctatttccg tcttgtttgg ggcggggact tgtatcttct cccccttcg ttgttgcgca       480 catttctcgg gaatgctacc aggagcagtt gcggttcttt ggcccttagg gagggctgca     540
ccggcaattt cttcgcttcc ttgctccaga ttttagttta tcttctacag tagcaagatg     600
atggatgggg acttgcgttt ttcttttcccc ttccttgttc cgggcatttc tctggagcaa    660
tgtttatgca tttcccagta ttgtcctttg ccctcagagg ggaggggatc ggcagttttc     720
ttcgcttcat cggtccagat tttagtttat cttgtacagt agcaagatga tggatgtgac     780
acaaagttct cagtttgggg gttgcgctct ccgggtagt tgttaatttc gtctgtgact       840
gactcgtatc tattcttgtg ggagcagggg caaactgggc aacccaagca gaggaagcca     900
caccggttca ggccaggcac ggtggcactg cgggagatca ggaagtacca gaaatcggtc    960
gactttctca tcccgtttgc accatttgtt cgtctggtgg gtacctctgt catatcctct    1020
cgctctctct accaacgatc tggagtgcgg agtgtaaatt ggaatctttt gttcctgaca   1080
aatttgtaga tcaaggaggt caccgacttc ttctgtcctg aaatcagccg ctggactccc    1140
caagcgctcg ttgcaattca agaggtcagt gctcaaacct ggcatgtact attagatctg    1200
atggtttgat tagagtacta caatgcagat gaattcaaga tctgaaaacc atgaactgtg    1260
gggtagatgc atgtatcata gtgtctgaat gctctggtat taattcagtt tgatatattt    1320
atttagcagc atggtattgt tttggtggct ggtaacccaa aactgaaacg tgattacgag    1380
caaaatggta tcaattgtct tttctgtgtg tttgtgcaaa tctggttgtt tggtcaagat    1440
atacagtctt gcaacatgaa tacatgatcc tgcccacaca ctcaaaactg aactattggt    1500
tagatgccat atgtcttatg gaatttaggg tgtaactgag aggtgagcaa gtggtagtga   1560
cgttcaattt tgattcagga tgaggatatt gtgatccaga aaattgcatg ttatggttat    1620
gtgtccgaac gccaaatgat tatgtctata tccactacat gcttatgtgt cccaaccccc    1680
aaatgattat ctctgtttcc agtacaacaa caaaaagtac tttagaacca gtcaagttta   1740
ttgtgcattt atacgagatt gttgtttgca caatagactt actttagtcg cctcttgcca    1800
gaaatgcctt cttctgcaca acgagcaaaa ataacataaa gttgactata ctcagtgtgg    1860
cctaagaaat gagttagtac ttttagtcac tggcctgtgt atttgctttg aattgacgca    1920
taattccctt ttcctttccc tctgcaggct gcagagtatc acctcgtcga cgtatttgaa    1980
agggcaaatc actgtgccat ccatgcaaag cgtgttaccg tcagtaagtt ctcactgaat    2040
gaaaacttcc ttccatttac aatattatgc agaaggaaac atgccagtta tgaaagagtt    2100
tcaattacag gatcaccttt gctttcattt gatgtgtatat ctagttttga tgttgtttca    2160
aggttcaaga attctaacga ttaatgatag gatccacaat tgttatatct ctgcagctcc    2220
tcgtatctgt tgtcaacgaa caaacatgtc aaacaattca ttaaaaaaaa cgaagatgtc    2280
aaaccgggtt actatagcag gaaattcagg gttgattacc tatttattca gggttgatta    2340
cctatttatt tcttatctga aggataaaca ttatataaaa tcagaatttt atttgtaggt    2400 tacattttt gtttccttat aaaacttgga aactgttgag aatcatcatc atcatggctg      2460
ttgctattct aacaaataaa acggatgctc ctgaataaat ggaactatat atgaagatgt    2520
atttactagc atgttcctgt taacctgact ttttttgctg ctacagtgca aaaggacata    2580
cagctcgcga ggcgtatcgg cgggaggagg ctttggtga                           2619
```

<210> SEQ ID NO 67
<211> LENGTH: 502
<212> TYPE: DNA
<213> ORGANISM: Triticum aestivum

<400> SEQUENCE: 67

| | | | | | | |
|---|---|---|---|---|---|---|
| atggcccgca | ccaagcaccc | ggccgtcagg | aagaccaagg | cgctgcccaa | gaagcagctc | 60 |
| gggacgcgcc | cctcggccgg | gacgccgcgg | cggcaggaga | cagatggcgc | gggcacgtcg | 120 |
| gcgactccga | ggcgagccgg | gcgggcggcg | gccccagggg | cggctgaagg | gcaaactgg | 180 |
| gcaacccaag | cagaggaagc | cacaccggtt | caggccaggc | acggtggcac | tgcgggagat | 240 |
| caggaagtac | cagaaatcgg | tcgactttct | catcccgttt | gcaccatttg | ttcgtctgat | 300 |
| caaggaggtc | accgacttct | tctgtcctga | aatcagccgc | tggactcccc | aagcgctcgt | 360 |
| tgcaattcaa | gaggctgcag | agtatcacct | cgtcgacgta | tttgaaaggg | caaatcactg | 420 |
| tgccatccat | gcaaagcgtg | ttaccgtcat | gcaaaaggac | atacagctcg | cgaggcgtat | 480 |
| cggcgggagg | aggctttggt | ga | | | | 502 |

<210> SEQ ID NO 68
<211> LENGTH: 2676
<212> TYPE: DNA
<213> ORGANISM: Triticum aestivum

<400> SEQUENCE: 68

| | | | | | | |
|---|---|---|---|---|---|---|
| atggcccgta | ccaagcaccc | ggccgtcagg | aagaccaagg | cgccgcccaa | gaagcagctc | 60 |
| gggcccgtc | ccgcgcagcg | gcggcaggag | acaggtcagc | ccgcccgccc | gtcgctcctc | 120 |
| ccttccttcc | cccccccgtc | tcccgcctct | cgaccgaacg | ccgccgcctt | gtttgttgcg | 180 |
| gtacagaggt | gcccgtccgt | gatgctaaca | ggttcttcct | ctcctttgca | gatggcgcgg | 240 |
| gcacgtcggc | gacaccggtg | cgcgggtctt | cccgggtcgc | ttccttttgt | ttcgtcttgt | 300 |
| tttctgtttt | ttggtctgac | ttgctcgtca | cctgttcgac | ggaatgcaga | ggcgagccgg | 360 |
| gcgggcggcg | gccccagggg | gcgctgaagg | tgcggccttc | tttgcgcttt | tcggttttcc | 420 |
| gccgcgtgtt | tagggccatt | tccgtcttgt | ttggggggtgg | gtggggcggg | ggcttgattt | 480 |
| ttttcctcct | cccttcgttg | ttgcgcacat | ttctcgggaa | tgcttccagg | agcggttgca | 540 |
| gttcttcttt | ggccttaggg | agggctggat | cggcagtttc | ttcgcttcct | tgctccagat | 600 |
| tttagtttat | cttgtagtag | tacagtagca | agatgatgga | tggggacttg | ttttttcttt | 660 |
| cccccttcctt | gttccggaca | tttctttgga | gcaacttttta | tgcattttcc | ggtattgtcc | 720 |
| tttgccctta | gagtggagtg | gatcggcagt | tttcttcgct | tccctggtcc | agattttagt | 780 |
| ttatctttac | agtagcaaga | tgatgtatgt | gacacaaagt | tctcagtttg | ggggttgcgc | 840 |
| tcttccaggt | gtagttgtta | tttttcgtct | gtgactgact | cgtatctatt | cttgtgggag | 900 |
| caggggcaaa | ctgggcaacc | caagcagagg | aagccacacc | ggttcaggcc | aggcacggtg | 960 |
| gcactgcggg | agatcaggag | gtaccagaag | tcggtcgact | ttctcatccc | gtttgcacca | 1020 |
| tttgtccgtc | tggtgggtac | ctctgtctgt | catatcctct | cgctctctct | accaacaatc | 1080 |
| tggagtgcgg | ggtgtaaact | ggaatctttt | gttcctgaca | aatttgcaga | tcaaggaggt | 1140 |
| caccgacttc | ttctgtcctg | aaatcagccg | ctggactccc | caagcgctcg | tcgcgattca | 1200 |
| agaggtcagt | gctcaaacct | ggcatgtact | attagatctg | atggtttgat | tagagtacta | 1260 |
| caatgcagat | gaattcaaga | tctgaaaacc | atgaactgtg | gggtagatgc | atgtatcgcc | 1320 |
| ttaattcata | gtttctgaat | gctctggtat | taattcagtt | tgatatattt | atttagctgc | 1380 |

```
atggtattgt tttggtggct ggtaattcaa aactgaaatg tgattacgag caaaatggta   1440
tcaattgtct tttctgtgca catctggttg tttggtcaag atatacagtc ttgcaacatg   1500
atcctgccca cacactcaaa actgaactat tggttagatt ccattttgct tatggaattt   1560
agggtgtaac tgagaggtga gcaggtggca gtgaccagag ctacgttcaa ttttgattca   1620
ggaagaggat cttgcgatcc agaaaattgc atgttatggt tatgtgtccg aaggccaaat   1680
gattatctct atatccagta catgcttatg tgtccgaacc cccaaatgat atctctata    1740 tccagtacat gcttatgtgt ccgaaccatt caagttattg tgcatttatt caagattgtt   1800
gtttgcacaa tagacttact ttagtcgcct cttgccagaa atgcctcctt ctgcacaatg   1860
agcaaaaata acataaagtt gattatgctc agtgtggcct aattgtactt tcagttactg   1920
gcctgtgtat ttgctttgaa ttgacacata attccctttt cctttccctc tgcaggctgc   1980
agagtatcac ctcgtcgacg tatttgaaag gcaaatcac tgtgccatcc atgcaaagcg     2040
tgttaccgtc agtaagttct cactgaatga aaacttcctt tcttttacaa tattatgcag   2100
aaggaaacat gccagttatg aaagagtttc aattacaaga tcacctttgc tttcatttga   2160
tgtggtatct agttttgatg ttgtttcaag gttcaagaat tctaatgatt aatgataggc   2220
tccacaattg ttatatctct gcagctcctc gtatctgacg aacaaacatg tcaaacaatt   2280
cattaaaaaa tgaagatgtc aaacaaacag tatatgcact gcatattgga tatcaaacct   2340
ggttactaca gcaggaagtt cagggttgat tactttattt cttatctgaa ggataaacat   2400
tgtatcaaat cagaatttta tttgtaagtt gcattttttg tttactcata aaacttggaa   2460
actgttttac tgtgagaaat agatgcccac tagaatcatg atcatcatca tggctgttgc   2520
tattctaaca aataaaacgg atgctcctga acaaatggaa ctatgtatga agatgtatgg   2580
actagcatgt tcctgttaac ctgactttt tttgctgcta cagtgcaaaa ggacatacag    2640
ctcgcgaggc gtatcggtgg gaggaggctt tggtga                             2676
```

<210> SEQ ID NO 69
<211> LENGTH: 4399
<212> TYPE: DNA
<213> ORGANISM: Triticum aestivum

<400> SEQUENCE: 69

```
atggcccgca ccaagcaccc ggccagtcag gaagaccaag gcgccgccca agaagcagct    60
cgggccccgc ccgcgcagc ggcggcagga gacaggtcag cccttccctc cttcctcccc    120
ccgtctcccg cctctcgagc gaacgccgtc gccatttcgt cgcgagagat ggacggacgg   180
acgccccacg catgacgcta atgtgctctt cctctccctt gcagatggc gcgggcacgt    240 cggcgacacc ggtgcgcggg accttccgg gtcgcttcct tttcgtttcg tcttgttttc     300
tgttttttgg tctgacttgc tcgtcacctg ttcgacggaa tgcagaggca gccgggcggg   360
cggcggcccc agggggggct caaggtgcgc ccttctttgc gcttttcggt tttccgccgc   420
gtgtttaggg ccatttccgt cttgtttggg ggtgcgcggg gcggggggctt gttttttttc  480 ctccccccctt cgttgttgcg cacattgctc gggaatgctg ccaggagcgg ttgcggttct  540
tctttgaccc ttcggggaggg ctggatcggc agtttcttcg cttccttgct ccagattta    600 gttcatcttg taccagtaca gtagcaagat gatggatggg ggcttgttt ttctttctcc    660 ttccttgttc cggacatttc tctggagcga cttttatgca tttttccagta ttgtcctttg   720 tccttagagg gtagtggatc ggcagttttc ttcgcctcat tggtccagat tttagtttat    780
```

```
cttgtacggt accaagatga tggatgtggc acaaagttct cagtttgggg gttgcgctct    840
tccgggcagt tgttattttg gtctgtgatg actaactcgt atctattctt gtgggagcag    900
gggcaactgg gcaacccaag cagaggaaac cacaccggtt caggccaggc acggtggcac    960
tgcgggagat caggaggtat cagaagtcgg tcgactttct catcccgttt gcaccatttg   1020
tccgtctggt gggtacctct gtctgtcata tcctctcgct ctctctacaa acgatctgca   1080
gtgcagagtg taattggaat attttgttcc tgacaaattt gcagatcaag gaggtcaccg   1140
acttcttctg tcctgaaatc agccgctgga ctccccaagc gctcgtcgcg attcaagagg   1200
tcagtgctaa aacctggcat gtactattag atctgatggt ttgattagag tactacaatg   1260
cagatgaatt caatatccga aaaccatgaa ctgtggggta gatacatgta tcgccttaat   1320
tcatggtttc tgaatgctct gctattaatt cagtttgata tatttattta gcagcatggt   1380
attgttttgg tggctggtaa atcaaaactg aaatgtgatt acgagcaaaa cggtatcgat   1440
tgtcgatcct gtgtgttttt gtgcacatct ggttgtttgg tcaagatgtg tttgtgcaca   1500
tcttgcaaca tgatcctgcc cacacactca aaactgacta ttggttaggt tccatttgtc   1560
ttatggaatt tagggtgtaa ctgagaggtg agcaagtggt agtaacgttc aattttgatt   1620
caggatgagg atattgtgat ccagaaaatt gcatgttatg ttatgtgtc caaacgccaa    1680 atgattatgt ctatatccag tactttagaa ccagtacaac aacaaaaagt actttagaac   1740
cagtcaagtt tattgtgcat ttatacaaga gtgttgtttg cacaatagac ttgctttagt   1800
cgtctcttgc cagaaatgcc ttcttctgca caacgagcaa aaataacata aagttgacta   1860
tactcagtgt ggcctaagaa atgagttgta ctttttagtc actggcctgt gtatttgctt   1920
tgaattgaca cataattccc ttttcctttc cctctgcagg ctgcagagta tcacctcgtc   1980
gacgtatttg aaagggcaaa tcactgtgcc atccatgcaa agcgtgttac cgtcagtaag   2040
ttctcactga atgaaaactc ccttttctttt acaatattgc gcagaaggaa acatgccagt   2100
tatgaaagag tttcaattac aggatcacct ttgctttcat ttgatgtgat atctagtttt   2160
gatgttgttt caaggttcaa gaattctaat gataaatgat aggatccaca attgttatat   2220
ctctgcagct cctcgtatct gttgtccacg aacaaacata tcaaacaatt cattaaaaag   2280
atgaagaagt caaacaaaca gtatatgtgc actgcatatt agatatcaaa cctggttact   2340
atacgactga tctggcctga cccccgcgtc gcctctccct ggcggcacgg ggggaaccac   2400
tccggcgccg ccaccttccc tcctccctcc acccccccacc tcgccgccgc ctgaggagtt   2460
cgccggcgaa gcccggtctg gctccaggga gggtggcggc ggggcatctc tctgcgaggc   2520
gtgagggcgc atctcgtgcg cgggcgcggc gagcttgggc gggatcgcgg gcgcggctct   2580
ggctcgggct ggtgaggctc cggcggtccg aggggtgtcg cggcgcggcg ggggtctcgc   2640
tccggcgcgg gcggtccgag ggcgcgcggg atctggcgct ccagcagggg cgccgtcaag   2700
gggagccggg cagggaagct cgtcaggcgg gctcgtcagg caggcgtgac gcggggcggc   2760
ggccgcgggc tggaagccat ggcgttttgg ccatggtgtc gtgtgcgctc gcttctcatt   2820
cgcagcttga ggtgctgctg ctgagggtgg tgcgcggtga agcttggtgg tcggcgttgg   2880
agagtgcaag gcgcaacagg aatggctcca atgatctcca cgcttctggg tggatcagat   2940
ctgcggccct ccatagggt gtgttccggg cgaaagcctt gacccgactt tgtcggtgcc    3000
gtcgacggcg gcgctttcgg gcgtcgtttc cctccttgga ggcgtcgttg tggaactcat   3060
cttcttctat gtgggctcg ggctctccgg gtgaaaacct aagctccaga ttttccggag    3120
cgggcgatgg cggcgtcttc gtcgtttccc tcttggggggc gttgcttggg agagttagct   3180
```

```
tgtgcttggt gcgtttggtt ttctcctacg tcgggtttgg tggatgccgg ggcagcggcc    3240
ccggacggct gatgaacgcc gaggcggcgg cctcggaaag tgatgcgcgg tgcggctcca    3300
tggggcgggg cggtggctcg gccttcactt gggtggcaat cttgggccac ttgggtggca    3360
ggcttgtcgg tccggtcgac gcgttccaga gggggcggtc tgactttgcg tcggggcggc    3420
ggccccggat gtggtgcgac gttcgtggtc tgcgagcggt tgccttgagc agcgtgggct    3480
gcgggcagct gggtcgcgcg gcgttgctgc tcgagcggag cggtggtacg tcggggcggc    3540
ggccccggaa ggtgatgccg gttgattgcg ctgggcgtga cggagcggtg gatgtcgggg    3600
cggcggcccc gagaaaatca ctgtggcgtc cagatttctg tggcaacgat gatggtggga    3660
gcgatgtcgg cgacgcggca atggttgcga tagtcggctc ttctccggcg tgtccacgat    3720
attgcctcgg tttgtttgtt gctgtggagt cgaagctgcg gcggcgaggc cctgtggtat    3780
acgatgactg gttccaggtg tcctttcgtc gatcttccgt ggcgccagcc gtgcctggtt    3840
tcgttcttcc gagttctccg tcagaatcgg agctgcgttg tctgtccgca ggtcgacatg    3900
ttgtcgagaa gggtgggctt tgccctgtgt gtttcagtct atgcgagtgg gctcggccct    3960
tgttgttctg gttttttgccc ggttttccgt aattaactgg gcaattctct tctgcttaat    4020
taatagatga ggcaatcttt gcctcccttt caaaaaaaaa cctggttact atagcaggaa    4080 attcaggggtt gattacttta tttcttatct gaaggataaa cattgtatca aatcagaatt    4140
ttatttgtaa gttacatttt tttttactta taaaacttgg aaactgtttt actgtgacaa    4200
atagatgcca ctagaatcat gatcacatcg tggctgttgc tattctaaca aataaatgct    4260
cctgaacaaa tgggaactat atatgaagat gtatggacca gcatgttcct gttaacctga    4320
cctttttcct ttttttgctg ctgcagtgca aaaggacata cagcttgcaa ggcgtatcgg    4380
cgggaggagg ctttggtga                                                 4399

<210> SEQ ID NO 70
<211> LENGTH: 492
<212> TYPE: DNA
<213> ORGANISM: Triticum aestivum

<400> SEQUENCE: 70
atggcccgca ccaagcaccc ggccagtcag gaagaccaag gcgccgccca agaagcagct     60
cgggccccgc cccgcgcagc ggcggcagga gacagatggc gcgggcacgt cggcgacacc    120
gaggcagccg gcgggcggc gggcccccaggg ggggctcaag gggcaactgg caacccaag    180 cagaggaaac cacaccggtt caggccaggc acggtggcac tgcgggagat cagaggtat     240 cagaagtcgg tcgactttct catcccgttt gcaccatttg tccgtctgat caaggaggtc    300
accgacttct tctgtcctga atcagccgc tggactcccc aagcgctcgt cgcgattcaa     360
gaggctgcag agtatcacct cgtcgacgta tttgaaaggg caaatcactg tgccatccat    420
gcaaagcgtg ttaccgtcat gcaaaaggac atacagcttg caaggcgtat cggcgggagg    480
aggctttggt ga                                                        492

<210> SEQ ID NO 71
<211> LENGTH: 163
<212> TYPE: PRT
<213> ORGANISM: Triticum aestivum

<400> SEQUENCE: 71

Met Ala Arg Thr Lys His Pro Ala Ser Gln Glu Asp Gln Gly Ala Ala
1               5                   10                  15
```

```
Gln Glu Ala Ala Arg Ala Pro Pro Arg Ala Ala Ala Gly Asp Arg
            20                  25                  30

Trp Arg Gly His Val Gly Asp Thr Glu Ala Ala Gly Arg Ala Ala Ala
        35                  40                  45

Pro Gly Gly Ala Gln Ala Thr Gly Gln Pro Lys Gln Arg Lys Pro
    50                  55                  60

His Arg Phe Arg Pro Gly Thr Val Ala Leu Arg Glu Ile Arg Arg Tyr
 65                  70                  75                  80

Gln Lys Ser Val Asp Phe Leu Ile Pro Phe Ala Pro Phe Val Arg Leu
                85                  90                  95

Ile Lys Glu Val Thr Asp Phe Phe Cys Pro Glu Ile Ser Arg Trp Thr
            100                 105                 110

Pro Gln Ala Leu Val Ala Ile Gln Glu Ala Ala Glu Tyr His Leu Val
        115                 120                 125

Asp Val Phe Glu Arg Ala Asn His Cys Ala Ile His Ala Lys Arg Val
    130                 135                 140

Thr Val Met Gln Lys Asp Ile Gln Leu Ala Arg Arg Ile Gly Gly Arg
145                 150                 155                 160

Arg Leu Trp

<210> SEQ ID NO 72
<211> LENGTH: 2619
<212> TYPE: DNA
<213> ORGANISM: Triticum aestivum

<400> SEQUENCE: 72
atggcccgca ccaagcaccc ggccgtcagg aagaccaagg cgctgcccaa gaagcagctc      60
gggacgcgcc cctcggccgg gacgccgcgg cggcaggaga caggtgagcc cgcccctcct     120
tccttcctcc cccccatctc gagcgaacgc cgtcgcctcg tcgcgagaga tggacgcccc     180
acgcgtgatg ctaatgtgtt cttcctctcc ctttgcagat ggcgcgggca cgtcggcgac     240
tccggtgcgc gggccttcct gggtcacttc cttttgtttc gtcttgtttt ctgttttggg     300
tctgacttgc tcgtctcctg ttcgacggaa tgcagaggcg aagccgggcg gcggcggcc      360
ccaggggcgg ctgaaggtgc gcccttcttt gtgcttttcg gttttccgcc gcgtgtttag     420
ggctatttcc gtcttgtttg gggcggggac ttgtatcttc tccccccttc gttgttgcgc     480
acatttctcg ggaatgctac caggagcagt tgcggttctt tggcccttag ggagggctgc     540
accggcaatt tcttcgcttc cttgctccag atttttagttt atcttctaca gtagcaagat     600
gatggatggg gacttgcgtt tttctttccc cttccttgtt ccgggcattt ctctggagca     660
atgtttatgc atttcccagt attgtccttt gccctcagag ggagggat cggcagtttt       720
cttcgcttca tcggtccaga ttttagttta tcttgtacag tagcaagatg atggatgtga     780
cacaaagttc tcagtttggg ggttgcgctc ttccgggtag ttgttaattt cgtctgtgac     840
tgactcgtat ctattcttgt gggagcaggg gcaactgggc aacccaagca gaggaagcca     900
caccggttca ggccaggcac ggtggcactg cgggagatca ggaagtacca gaaatcggtc     960
gactttctca tcccgtttgc accatttgtt cgtctggtgg gtacctctgt catatcctct    1020
cgctctctct accaacgatc tggagtgcgg agtgtaaatt ggaatctttt gttcctgaca    1080
aatttgtaga tcaaggaggt caccgacttc ttctgtcctg aaatcagccg ctggactccc    1140
caagcgctcg ttgcaattca agaggtcagt gctcaaacct ggcatgtact attagatctg    1200
atggtttgat tagagtacta caatgcagat gaattcaaga tctgaaaacc atgaactgtg    1260
```

```
gggtagatgc atgtatcata gtgtctgaat gctctggtat taattcagtt tgatatattt    1320
atttagcagc atggtattgt tttggtggct ggtaacccaa aactgaaacg tgattacgag    1380
caaaatggta tcaattgtct tttctgtgtg tttgtgcaaa tctggttgtt tggtcaagat    1440
atacagtctt gcaacatgaa tacatgatcc tgcccacaca ctcaaaactg aactattggt    1500
tagatgccat atgtcttatg gaatttaggg tgtaactgag aggtgagcaa gtggtagtga    1560
cgttcaattt tgattcagga tgaggatatt gtgatccaga aaattgcatg ttatggttat    1620
gtgtccgaac gccaaatgat tatgtctata tccactacat gcttatgtgt cccaacccca    1680
aaatgattat ctctgtttcc agtacaacaa caaaaagtac tttagaacca gtcaagttta    1740
ttgtgcattt atacgagatt gttgtttgca caatagactt actttagtcg cctcttgcca    1800
gaaatgcctt cttctgcaca acgagcaaaa ataacataaa gttgactata ctcagtgtgg    1860
cctaagaaat gagttagtac ttttagtcac tggcctgtgt atttgctttg aattgacgca    1920
taattcccct ttccttttccc tctgcaggct gcagagtatc acctcgtcga cgtatttgaa    1980
agggcaaatc actgtgccat ccatgcaaag cgtgttaccg tcagtaagtt ctcactgaat    2040
gaaaacttcc ttccatttac aatattatgc agaaggaaac atgccagtta tgaaagagtt    2100
tcaattacag gatcacccttt gctttcattt gatgtgatat ctagttttga tgttgtttca    2160
aggttcaaga attctaacga ttaatgatag gatccacaat tgttatatct ctgcagctcc    2220
tcgtatctgt tgtcaacgaa caaacatgtc aaacaattca ttaaaaaaaa cgaagatgtc    2280
aaaccgggtt actatagcag gaaattcagg gttgattacc tatttattca gggttgatta    2340
cctatttatt tcttatctga aggataaaca ttatataaaa tcagaatttt atttgtaggt    2400 tacattttttt gtttccttat aaaacttgga aactgttgag aatcatcatc atcatggctg    2460
ttgctattct aacaaataaa acggatgctc ctgaataaat ggaactatat atgaagatgt    2520
atttactagc atgttcctgt taacctgact tttttttgctg ctacagtgca aaaggacata    2580
cagctcgcga ggcgtatcgg cgggaggagg ctttggtga                          2619

<210> SEQ ID NO 73
<211> LENGTH: 2673
<212> TYPE: DNA
<213> ORGANISM: Triticum aestivum

<400> SEQUENCE: 73
atggcccgta ccaagcaccc ggccaggaag accaaggcgc cgcccaagaa gcagctcggg     60
ccccgtcccg cgcagcggcg gcaggagaca ggtcagcccg cccgcccgtc gctcctccct    120
tccttccccc ccccgtctcc cgcctctcga ccgaacgccg ccgccttgtt tgttgcggta    180
cagaggtgcc cgtccgtgat gctaacaggt tcttcctctc ctttgcagat ggcgcgggca    240
cgtcggcgac accggtgcgc gggtcttccc gggtcgcttc cttttgtttc gtcttgttttt   300 ctgtttttttg gtctgacttg ctcgtcacct gttcgacgga atgcagaggc gaagccgggc    360
gggcggcggc cccagggggc gctgaaggtg cggccttctt tgcgcttttc ggttttccgc    420
cgcgtgttta gggccatttc cgtcttgttt gggggtgggt ggggcggggg cttgattttt    480
ttcctcctcc cttcgttgtt gcgcacattt ctcgggaatg cttccaggag cggttgcagt    540
tcttctttgg ccttagggag ggctggatcg gcagtttctt cgcttccttg ctccagattt    600
tagtttatct tgtagtagta cagtagcaag atgatggatg gggacttgtt ttttctttcc    660
ccttccttgt tccggacatt tctttggagc aacttttatg catttcccgg tattgtcctt    720
```

| | |
|---|---|
| tgcccttaga gtggagtgga tcggcagttt tcttcgcttc cctggtccag attttagttt | 780 |
| atctttacag tagcaagatg atgtatgtga cacaaagttc tcagtttggg ggttgcgctc | 840 |
| ttccaggtgt agttgttatt tttcgtctgt gactgactcg tatctattct tgtgggagca | 900 |
| ggggcaactg gcaacccaa gcagaggaag ccacaccggt tcaggccagg cacggtggca | 960 |
| ctgcgggaga tcaggaggta ccagaagtcg gtcgactttc tcatcccgtt tgcaccattt | 1020 |
| gtccgtctgg tgggtacctc tgtctgtcat atcctctcgc tctctctacc aacaatctgg | 1080 |
| agtgcgggt gtaaactgga atcttttgtt cctgacaaat ttgcagatca aggaggtcac | 1140 |
| cgacttcttc tgtcctgaaa tcagccgctg gactccccaa gcgctcgtcg cgattcaaga | 1200 |
| ggtcagtgct caaacctggc atgtactatt agatctgatg gtttgattag agtactacaa | 1260 |
| tgcagatgaa ttcaagatct gaaaaccatg aactgtgggg tagatgcatg tatcgcctta | 1320 |
| attcatagtt tctgaatgct ctggtattaa ttcagtttga tatatttatt tagctgcatg | 1380 |
| gtattgtttt ggtggctggt aattcaaaac tgaaatgtga ttacgagcaa atggtatca | 1440 |
| attgtctttt ctgtgcacat ctggttgttt ggtcaagata tacagtcttg caacatgatc | 1500 |
| ctgcccacac actcaaaact gaactattgg ttagattcca ttttgcttat ggaatttagg | 1560 |
| gtgtaactga gaggtgagca ggtggcagtg accagagcta cgttcaattt tgattcagga | 1620 |
| agaggatctt gcgatccaga aaattgcatg ttatggttat gtgtccgaag gccaaatgat | 1680 |
| tatctctata tccagtacat gcttatgtgt ccgaaccccc aaatgattat ctctatatcc | 1740 |
| agtacatgct tatgtgtccg aaccattcaa gttattgtgc atttattcaa gattgttgtt | 1800 |
| tgcacaatag acttacttta gtcgcctctt gccagaaatg cctccttctg cacaatgagc | 1860 |
| aaaaataaca taaagttgat tatgctcagt gtggcctaat tgtactttca gttactggcc | 1920 |
| tgtgtatttg ctttgaattg acacataatt ccctttcct ttccctctgc aggctgcaga | 1980 |
| gtatcacctc gtcgacgtat ttgaaagggc aaatcactgt gccatccatg caaagcgtgt | 2040 |
| taccgtcagt aagttctcac tgaatgaaaa cttccttttct tttacaatat tatgcagaag | 2100 |
| gaaacatgcc agttatgaaa gagtttcaat tacaagatca cctttgcttt catttgatgt | 2160 |
| ggtatctagt tttgatgttg tttcaaggtt caagaattct aatgattaat gataggatcc | 2220 |
| acaattgtta tatctctgca gctcctcgta tctgacgaac aaacatgtca aacaattcat | 2280 |
| taaaaaatga agatgtcaaa caaacagtat atgcactgca tattggatat caaacctggt | 2340 |
| tactacagca ggaagttcag ggttgattac tttatttctt atctgaagga taaacattgt | 2400 |
| atcaaatcag aattttattt gtaagttgca ttttttgttt actcataaaa cttggaaact | 2460 |
| gttttactgt gagaaataga tgcccactag aatcatgatc atcatcatgg ctgttgctat | 2520 |
| tctaacaaat aaaacggatg ctcctgaaca aatggaacta tgtatgaaga tgtatggact | 2580 |
| agcatgttcc tgttaacctg actttttttt gctgctacag tgcaaaagga catacagctc | 2640 |
| gcgaggcgta tcggtgggag gaggctttgg tga | 2673 |

<210> SEQ ID NO 74
<211> LENGTH: 18400
<212> TYPE: DNA
<213> ORGANISM: Artificial Sequence
<220> FEATURE:
<223> OTHER INFORMATION: Construct 24195
<220> FEATURE:
<221> NAME/KEY: misc_feature
<222> LOCATION: (4)..(259)
<223> OTHER INFORMATION: bNRB-05
<220> FEATURE:
<221> NAME/KEY: misc_feature -continued

```
<222> LOCATION: (101)..(125)
<223> OTHER INFORMATION: bNRB-01-01
<220> FEATURE:
<221> NAME/KEY: enhancer
<222> LOCATION: (168)..(259)
<223> OTHER INFORMATION: eNOS-01
<220> FEATURE:
<221> NAME/KEY: enhancer
<222> LOCATION: (292)..(485)
<223> OTHER INFORMATION: eFMV-06
<220> FEATURE:
<221> NAME/KEY: enhancer
<222> LOCATION: (492)..(784)
<223> OTHER INFORMATION: e35S-11
<220> FEATURE:
<221> NAME/KEY: promoter
<222> LOCATION: (791)..(2592)
<223> OTHER INFORMATION: prSoUbi4-02
<220> FEATURE:
<221> NAME/KEY: misc_feature
<222> LOCATION: (1170)..(1234)
<223> OTHER INFORMATION: u5SoUbi4-02
<220> FEATURE:
<221> NAME/KEY: Intron
<222> LOCATION: (1235)..(2592)
<223> OTHER INFORMATION: iSoUbi4-02
<220> FEATURE:
<221> NAME/KEY: misc_feature
<222> LOCATION: (2607)..(2657)
<223> OTHER INFORMATION: NLS
<220> FEATURE:
<221> NAME/KEY: gene
<222> LOCATION: (2607)..(6827)
<223> OTHER INFORMATION: CRISPR associated 9
<220> FEATURE:
<221> NAME/KEY: misc_feature
<222> LOCATION: (2610)..(2610)
<223> OTHER INFORMATION: +4G
<220> FEATURE:
<221> NAME/KEY: misc_feature
<222> LOCATION: (2611)..(2611)
<223> OTHER INFORMATION: +5C
<220> FEATURE:
<221> NAME/KEY: mutation
<222> LOCATION: (6147)..(6149)
<223> OTHER INFORMATION: L to V mutation
<220> FEATURE:
<221> NAME/KEY: mutation
<222> LOCATION: (6192)..(6194)
<223> OTHER INFORMATION: I to V mutation
<220> FEATURE:
<221> NAME/KEY: misc_feature
<222> LOCATION: (6762)..(6824)
<223> OTHER INFORMATION: NLS
<220> FEATURE:
<221> NAME/KEY: terminator
<222> LOCATION: (6834)..(7835)
<223> OTHER INFORMATION: tZmMTL-01
<220> FEATURE:
<221> NAME/KEY: misc_feature
<222> LOCATION: (7836)..(7847)
<223> OTHER INFORMATION: xSTOPS-01
<220> FEATURE:
<221> NAME/KEY: promoter
<222> LOCATION: (7855)..(8216)
<223> OTHER INFORMATION: prTau6-01
<220> FEATURE:
<221> NAME/KEY: misc_feature
<222> LOCATION: (8217)..(8236)
<223> OTHER INFORMATION: xTaCenh3 target-03
<220> FEATURE:
<221> NAME/KEY: misc_feature
<222> LOCATION: (8217)..(8321)
<223> OTHER INFORMATION: gRNA TaCenH3-03
<220> FEATURE:
<221> NAME/KEY: misc_feature
<222> LOCATION: (8237)..(8248)
<223> OTHER INFORMATION: crRNA-01
<220> FEATURE:
```

```
<221> NAME/KEY: misc_feature
<222> LOCATION: (8253)..(8321)
<223> OTHER INFORMATION: tracrRNA-01
<220> FEATURE:
<221> NAME/KEY: promoter
<222> LOCATION: (8322)..(8683)
<223> OTHER INFORMATION: prTaU6-01
<220> FEATURE:
<221> NAME/KEY: misc_feature
<222> LOCATION: (8684)..(8703)
<223> OTHER INFORMATION: xTaCenH3 target-04
<220> FEATURE:
<221> NAME/KEY: misc_feature
<222> LOCATION: (8684)..(8788)
<223> OTHER INFORMATION: guide RNA TaCenH3-04
<220> FEATURE:
<221> NAME/KEY: misc_feature
<222> LOCATION: (8704)..(8715)
<223> OTHER INFORMATION: crRNA-01
<220> FEATURE:
<221> NAME/KEY: misc_feature
<222> LOCATION: (8720)..(8788)
<223> OTHER INFORMATION: tracrRNA-01
<220> FEATURE:
<221> NAME/KEY: misc_feature
<222> LOCATION: (8795)..(8806)
<223> OTHER INFORMATION: xSTOPS-01
<220> FEATURE:
<221> NAME/KEY: promoter
<222> LOCATION: (8807)..(10799)
<223> OTHER INFORMATION: prUbi1-10
<220> FEATURE:
<221> NAME/KEY: TATA_signal
<222> LOCATION: (9677)..(9685)
<223> OTHER INFORMATION: TATA box
<220> FEATURE:
<221> NAME/KEY: Intron
<222> LOCATION: (9790)..(10799)
<223> OTHER INFORMATION: iUbi1-02-01
<220> FEATURE:
<221> NAME/KEY: gene
<222> LOCATION: (10811)..(11989)
<223> OTHER INFORMATION: cPMI-12
<220> FEATURE:
<221> NAME/KEY: terminator
<222> LOCATION: (11994)..(13028)
<223> OTHER INFORMATION: tUbi1-01
<220> FEATURE:
<221> NAME/KEY: misc_feature
<222> LOCATION: (13072)..(13083)
<223> OTHER INFORMATION: xSTOPS-01
<220> FEATURE:
<221> NAME/KEY: misc_feature
<222> LOCATION: (13084)..(13123)
<223> OTHER INFORMATION: xTAG-02
<220> FEATURE:
<221> NAME/KEY: misc_feature
<222> LOCATION: (13132)..(13261)
<223> OTHER INFORMATION: bNLB-05
<220> FEATURE:
<221> NAME/KEY: misc_feature
<222> LOCATION: (13167)..(13191)
<223> OTHER INFORMATION: bNLB-01-01
<220> FEATURE:
<221> NAME/KEY: gene
<222> LOCATION: (13541)..(14329)
<223> OTHER INFORMATION: cSpec-03
<220> FEATURE:
<221> NAME/KEY: promoter
<222> LOCATION: (14424)..(14554)
<223> OTHER INFORMATION: prVirG-01
<220> FEATURE:
<221> NAME/KEY: gene
<222> LOCATION: (14629)..(15354)
<223> OTHER INFORMATION: cVirG-01
<220> FEATURE:
<221> NAME/KEY: gene
<222> LOCATION: (15384)..(16457)
<223> OTHER INFORMATION: cRepA-03
```

<220> FEATURE:
<221> NAME/KEY: misc_feature
<222> LOCATION: (16500)..(16904)
<223> OTHER INFORMATION: oVS1-02
<220> FEATURE:
<221> NAME/KEY: misc_feature
<222> LOCATION: (17582)..(18388)
<223> OTHER INFORMATION: oCOLE-06

<400> SEQUENCE: 74

```
attcctgtgg ttggcatgca catacaaatg gacgaacgga taaaccttttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg acccccgccg atgacgcggg acaagccgtt ttacgtttgg     240
aactgacaga accgcaacgc tgcaggaatt ggccgcagcg gccatttaaa tagctgcttg     300
tggggaccag acaaaaaagg aatggtgcag aattgttagg cgcacctacc aaaagcaact     360
ttgcctttat tgcaaagata aagcagattc ctctagtaca agtggggaac aaaataacgt     420
ggaaaagagc tgtcctgaca gcccactcac tattgcgttt gacgaacgca gtgacgacca     480
caaaactcga gacttttcaa caagggtat atccggaaa cctcctcgga ttccattgcc     540
cagctatctg tcactttatt gtgaagatag tggaaaagga aggtggctcc tacaaatgcc     600
atcattgcga taaggaaag gctatcgttg aagatgcctc tgccgacagt ggtcccaaag     660
atggacccc acccacgagg agcatcgtgg aaaaagaaga cgttccaacc acgtcttcaa     720
agcaagtgga ttgatgtgat atctccactg acgtaagggt tgacgaacaa tcccactatc     780
cttcggaccc gaattcatta tgtggtctag gtaggttcta tatataagaa aacttgaaat     840
gttctaaaaa aaaattcaag cccatgcatg attgaagcaa acggtatagc aacggtgtta     900
acctgatcta gtgatctctt gcaatcctta acggccacct accgcaggta gcaaacggcg     960
tccccctcct cgatatctcc gcggcgacct ctggcttttt ccgcggaatt gcgcggtggg    1020
gacggattcc acgagaccgc gacgcaaccg cctctcgccg ctgggcccca caccgctcgg    1080
tgccgtagcc tcacgggact ctttctcct cctccccgt tataaattgg cttcatcccc    1140
tccttgcctc atccatccaa atcccagtcc ccaatcccat cccttcgtag gagaaattca    1200
tcgaagctaa gcgaatcctc gcgatcctct caaggtactg cgagttttcg atccccctct    1260
cgacccctcg tatgtttgtg tttgtcgtag cgtttgatta ggtatgcttt ccctgttgt    1320
gttcgtcgta gcgtttgatt aggtatgctt tccctgttcg tgttcatcgt agtgtttgat    1380
taggtcgtgt gaggcgatgg cctgctcgcg tccttcgatc tgtagtcgat ttgcgggtcg    1440
tggtgtagat ctgcgggctg tgatgaagtt atttggtgtg atctgctcgc ctgattctgc    1500
gggttggctc gagtagatat gatggttgga ccggttggtt cgtttaccgc gctagggttg    1560
ggctgggatg atgttgcatg cgccgttgcg cgtgatcccg cagcaggact tgcgtttgat    1620
tgccagatct cgttacgatt atgtgatttg gtttggactt tttagatctg tagcttctgc    1680
ttatgtgcca gatgcgccta ctgctcatat gcctgatgat aatcataaat ggctgtggaa    1740
ctaactagtt gattgcggag tcatgtatca gctacaggtg tagggactag ctacaggtgt    1800
agggacttgc gtctaattgt ttggtccttt actcatgttg caattatgca atttagttta    1860
gattgtttgt tccactcatc taggctgtaa aagggacact gcttagattg ctgtttaatc    1920
tttttagtag attatattat attggtaact tattacccct attacatgcc atacgtgact    1980
tctgctcatg cctgatgata atcatagatc actgtggaat taattagttg attgttgaat    2040
```

```
catgtttcat gtacatacca cggcacaatt gcttagttcc ttaacaaatg caaattttac    2100
tgatccatgt atgatttgcg tggttctcta atgtgaaata ctatagctac ttgttagtaa    2160
gaatcaggtt cgtatgctta atgctgtatg tgccttctgc tcatgcctga tgataatcat    2220
atatcactgg aattaattag ttgatcgttt aatcatatat caagtacata ccatgccaca    2280 attttagtc acttaaccca tgcagattga actggtccct gcatgttttg ctaaattgtt    2340
ctattctgat tagaccatat atcatgtatt ttttttggt aatggttctc ttattttaaa    2400
tgctatatag ttctggtact tgttagaaag atctgcttca tagtttagtt gcctatccct    2460
cgaattagga tgctgagcag ctgatcctat agctttgttt catgtatcaa ttcttttgtg    2520
ttcaacagtc agttttgtt agattcattg taacttatgg tcgcttactc ttctggtcct    2580
caatgcttgc agcctagtaa gccgccatgg ccccaaagaa gaagaggaag gtcggcatcc    2640
acggcgtccc agctgcgatg gacaagaagt actccatcgg cctcgacatc ggcaccaaca    2700
gcgtgggctg ggccgtcatc accgacgagt acaaggtgcc atccaagaag ttcaaggtcc    2760
tgggcaacac cgaccgccac agcatcaaga gaaacctcat cggcgctctc ctgttcgact    2820
ccggcgagac ggctgaggct accaggctca gcgcaccgc caggaggagg tacaccagga    2880
ggaagaacag gatctgctac ctccaagaga tcttctccaa cgagatggcc aaggtggacg    2940
actccttctt ccaccgcctg gaggagagct cctcgtcga ggaggacaag aagcacgaga    3000
ggcacccaat cttcggcaac atcgtggacg aggtcgccta ccacgagaag tacccaacca    3060
tctaccacct gaggaagaag ctcgtggact ccaccgacaa ggccgacctc cgcctgatct    3120
acctcgccct ggcccacatg atcaagttca gggccactt cctgatcgag ggcgacctca    3180
acccagacaa cagcgacgtg gacaagctgt tcatccaact cgtccagacc tacaaccagc    3240
tcttcgagga gaacccgatc aacgcttccg gcgtggacgc taaggctatc ctgagcgcta    3300
ggctctccaa gagcaggagg ctcgagaacc tgatcgccca gctcccaggc gagaagaaga    3360
acggcctgtt cggcaacctc atcgctctct ccctgggcct cacccaaac ttcaagagca    3420 acttcgacct cgccgaggac gccaagctgc aactctccaa ggacacctac gacgacgacc    3480
tggacaacct cctggcccag atcggcgacc aatacgccga cctgttcctc gccgccaaga    3540
acctgtccga cgccatcctc ctgagcgaca tcctccgcgt gaacaccgag atcaccaagg    3600 cccactctc cgccagcatg atcaagcgct acgacgagca ccaccaggac ctgaccctcc    3660
tgaaggccct ggtcaggcaa cagctcccag agaagtacaa ggagatcttc ttcgaccaga    3720
gcaagaacgg ctacgctggc tacatcgacg gcggcgcctc ccaagaggag ttctacaagt    3780
tcatcaagcc aatcctggag aagatggacg gcaccgagga gctcctggtg aagctcaaca    3840
gggaggacct cctgaggaag cagcgcacct tcgacaacgg cagcatccca caccaaatcc    3900
acctcggcga gctgcacgct atcctgagga ggcaagagga cttctaccca ttcctcaagg    3960
acaacaggga gaagatcgag aagatcctga ccttccgcat ccctactac gtcggcccac    4020 tcgctagggg caactccagg ttcgcttgga tgacccgcaa gagcgaggag acgatcaccc    4080
cgtggaactt cgaggaggtc gtcgacaagg cgcttccgc tcagagcttc atcgagagga    4140
tgaccaactt cgacaagaac ctgccaaacg agaaggtgct cccaaagcac tccctcctgt    4200
acgagtactt caccgtctac aacgagctca ccaaggtgaa gtatgtgacc gagggcatgc    4260
gcaagccagc cttcctgagc ggcgagcaga agaaggccat cgtggacctc ctgttcaaga    4320
ccaacaggaa ggtgaccgtc aagcaactca aggaggacta cttcaagaag atcgagtgct    4380
tcgactccgt ggagatcagc ggcgtcgagg accgcttcaa cgcctccctc ggcacctacc    4440
```

```
acgacctcct gaagatcatc aaggacaagg acttcctgga caacgaggag aacgaggaca      4500
tcctcgagga catcgtgctg accctcaccc tgttcgagga cagggagatg atcgaggagc      4560
gcctgaagac ctacgcccac ctcttcgacg acaaggtcat gaagcaactc aagaggagga      4620
ggtacaccgg ctggggcagg ctgagccgca agctcatcaa cggcatccgc gacaagcagt      4680
ccggcaagac catcctcgac ttcctgaaga gcgacggctt cgccaacagg aacttcatgc      4740
aactgatcca cgacgactcc ctcaccttca aggaggacat ccaaaaggct caggtgtccg      4800
gccagggcga cagcctgcac gagcacatcg ctaacctcgc tggcagccca gccatcaaga      4860
agggcatcct gcagaccgtg aaggtcgtcg acgagctcgt gaaggtcatg ggcaggcaca      4920
agccagagaa catcgtcatc gagatggccc gcgagaacca gaccacccag aagggccaaa      4980
agaactccag ggagcgcatg aagcgcatcg aggagggcat caaggagctg ggcagccaaa      5040
tcctcaagga gcacccagtg gagaacaccc aactgcagaa cgagaagctc tacctgtact      5100
acctccagaa cggcagggac atgtatgtgg accaagagct ggacatcaac cgcctctccg      5160
actacgacgt ggaccacatc gtcccacagt ccttcctgaa ggacgacagc atcgacaaca      5220
aggtgctcac caggagcgac aagaaccgcg gcaagtccga caacgtccca agcgaggagg      5280
tggtcaagaa gatgaaaaac tactggaggc agctcctgaa cgccaagctg atcacccaaa      5340
ggaagttcga caacctcacc aaggctgaga ggggcggcct ctccgagctg acaaggccg       5400 gcttcattaa aaggcagctg gtggagacgc gccaaatcac caagcacgtc gcccaaatcc      5460
tcgacagccg catgaacacc aagtacgacg agaacgacaa gctgatcagg gaggtgaagg      5520
tcatcaccct gaagtccaag ctcgtgagcg acttcaggaa ggacttccag ttctacaagg      5580
tccgcgagat caataattac caccacgccc acgacgctta cctcaacgct gtggtcggca      5640
ccgccctgat taaaaagtac ccaaagctcg agtccgagtt cgtgtacggc gactacaagg      5700
tgtacgacgt ccgcaagatg atcgccaagt ccgagcaaga gatcggcaag gccaccgcca      5760
agtacttctt ctacagcaac atcatgaact tcttcaagac cgagatcacc ctggccaacg      5820
gcgagatcag gaagcgccca ctcatcgaga cgaacggcga gacgggcgag atcgtgtggg      5880
acaagggcag ggacttcgcc accgtgcgca aggtcctctc catgccacag gtgaacatcg      5940
tcaagaagac cgaggtccaa accggcggct ctccaaggga gagcatcctg ccaaagagga      6000
acagcgacaa gctcatcgcc cgcaagaagg actgggatcc aaagaagtac ggcggcttcg      6060 actcccaac cgtggcctac agcgtcctcg tggtcgccaa ggtggagaag ggcaagtcca       6120
agaagctgaa gagcgtgaag gagctcgtcg gcatcaccat catggagagg tccagcttcg      6180
agaagaaccc agtggacttc ctcgaggcca agggctacaa ggaggtcaag aaggacctga      6240
tcattaaact cccaaagtac agcctcttcg agctggagaa cggcaggaag cgcatgctgg      6300
cttccgctgg cgagctccaa aagggcaacg agctcgccct gccatccaag tatgtgaact      6360
tcctctacct ggcctcccac tacgagaagc tcaaggcag cccagaggac aacgagcaaa        6420
agcagctgtt cgtcgagcag cacaagcact acctcgacga gatcatcgag caaatctccg      6480
agttcagcaa gcgcgtgatc ctcgccgacg ccaacctgga caaggtcctc tccgcctaca      6540
acaagcacag ggacaagcca atccgcgagc aggccgagaa catcatccac ctcttcaccc      6600
tgaccaacct cggcgctcca gctgccttca gtacttcga caccaccatc gacaggaagc      6660
gctacacctc caccaaggag gtgctggacg ccacccctat cccaccagtcc atcaccggcc    6720 tctacgagac gaggatcgac ctgagccaac tcggcggcga ctccagccca ccaaagaaga     6780
```

```
agaggaaggt cagctggaag gacgcttccg gctggagccg catgtgaggt acctcacatc    6840
gatcgacgac caaggatatg attattatct atctagcttg tggtggtggt tgaacaataa    6900
taagcgaggc cgagctggct gccatacata ggtattgtgt ggtgtgtgtg agagagagag    6960
aaacagagtt cttcagtttg ctatctctct ctgcatgttt ggcgtcagtc tttgtgctca    7020
tgtacgtacg tgtgtctacc tgcatgttgg ttgatccgat tgcatctgct gtaaccatat    7080
attaattggt ccacgatgat atgatttgat actatatata tactaaaacc ggacttctta    7140
ttataatact tgtagtatat aagtttctta cgcccgcaat tgatcgattc agaaggagtt    7200
ctagctagct aaaacatgca gattcagaat atcagatttt taggactact ggagatccag    7260
aaccttcgtg tccttgtacc cgtgattttg gatcccettt ctccccacta caatcgttgg    7320
cgcaatcttg ttctgctcgc ctagaatggt acgccctcac cgaccatgtc ctcgccgatg    7380
cctaccccgc cacgccatct ggatggtgca tgaatgtcgt cgttttgtcc tggatgctag    7440
gcacactctc ccccgagttg atggagcctc ctcgcacctc tggtggcact gcgccgcgcc    7500
tggcttgcca tcgaggagca attcctcggc aatcgcgaag ctcgcacact tcgtctcgac    7560
gccgagttcc atgtcttcat gtaggcgatc tcttcgtcag cgactattgt ctattgacgc    7620
aagatgaagg ggatggacga ggcccttggt gatcttggtg aggtcatcca tgaccgtacc    7680
cttgtcctaa acgtgttgtg tggtctgaat gagaggtttg cccacataaa ggtccacttc    7740
aagcactcga atccgttccc ctccttcacc gacgtttgta atgatctcat ccttgaggag    7800
atcgactcca gcgcgcctcc tccgcctccg accacctaat tagctaaggg acccgaccaa    7860
gcccgttatt ctgacagttc tggtgctcaa cacatttata tttatcaagg agcacattgt    7920
tactcactgc taggagggaa tcgaactagg aatattgatc agaggaacta cgagagagct    7980
gaagataact gccctctagc tctcactgat ctgggtcgca tagtgagatg cagcccacgt    8040
gagttcagca acggtctagc gctgggcttt taggcccgca tgatcgggct tttgtcgggt    8100
ggtcgacgtg ttcacgattg gggagagcaa cgcagcagtt cctcttagtt tagtcccacc    8160
tcgcctgtcc agcagagttc tgaccggttt ataaactcgc ttgctgcatc agacttgcct    8220
tggtcttcct gacggcgttt tagagctaga aatagcaagt taaaataagg ctagtccgtt    8280
atcaacttga aaaagtggca ccgagtcggt gcttttttt tgaccaagcc cgttattctg    8340
acagttctgg tgctcaacac atttatattt atcaaggagc acattgttac tcactgctag    8400
gagggaatcg aactaggaat attgatcaga ggaactacga gagagctgaa gataactgcc    8460
ctctagctct cactgatctg gtcgcatag tgagatgcag cccacgtgag ttcagcaacg    8520
gtctagcgct gggcttttag gcccgcatga tcgggctttt gtcgggtggt cgacgtgttc    8580
acgattgggg agagcaacgc agcagttcct cttagtttag tcccacctcg cctgtccagc    8640
agagttctga ccggtttata aactcgcttg ctgcatcaga cttgacggaa tgcagaggcg    8700
agcgttttag agctagaaat agcaagttaa aataaggcta gtccgttatc aacttgaaaa    8760
agtggcaccg agtcggtgct tttttttcc taggctaatt agctaactgc agtgcagcgt    8820
gacccggtcg tgccctctc tagagataat gagcattgca tgtctaagtt ataaaaaatt    8880
accacatatt tttttgtca cacttgtttg aagtgcagtt tatctatctt tatacatata    8940
tttaaacttt actctacgaa taatataatc tatagtacta caataatatc agtgttttag    9000
agaatcatat aaatgaacag ttagacatgg tctaaaggac aattgagtat tttgacaaca    9060
ggactctaca gttttatctt tttagtgtgc atgtgttctc cttttttttt gcaaatagct    9120
tcacctatat aatacttcat ccatttttatt agtacatcca tttagggttt agggttaatg    9180
```

```
gtttttatag actaattttt ttagtacatc tattttattc tattttagcc tctaaattaa    9240
gaaaactaaa actctatttt agtttttta tttaataatt tagatataaa atagaataaa     9300
ataaagtgac taaaaattaa acaaataccc tttaagaaat taaaaaaact aaggaaacat    9360
ttttcttgtt tcgagtagat aatgccagcc tgttaaacgc cgtcgacgag tctaacggac    9420
accaaccagc gaaccagcag cgtcgcgtcg ggccaagcga agcagacggc acggcatctc    9480
tgtcgctgcc tctggacccc tctcgagagt tccgctccac cgttggactt gctccgctgt    9540
cggcatccag aaattgcgtg gcggagcggc agacgtgagc cggcacggca ggcggcctcc    9600
tcctcctctc acggcaccgg cagctacggg ggattccttt cccaccgctc cttcgctttc    9660
ccttcctcgc ccgccgtaat aaatagacac cccctccaca ccctctttcc ccaacctcgt    9720
gttgttcgga gcgcacacac acacaaccag atctccccca aatccacccg tcggcacctc    9780
cgcttcaagg tacgccgctc gtcctccccc ccccccctc tctaccttct ctagatcggc     9840
gttccggtcc atggttaggg cccggtagtt ctacttctgt tcatgtttgt gttagatccg    9900
tgtttgtgtt agatccgtgc tgctagcgtt cgtacacgga tgcgacctgt acgtcagaca    9960
cgttctgatt gctaacttgc cagtgttct ctttggggaa tcctgggatg gctctagccg     10020
ttccgcagac gggatcgatt tcatgatttt ttttgtttcg ttgcataggg tttggtttgc    10080
ccttttcctt tatttcaata tatgccgtgc acttgtttgt cgggtcatct tttcatgctt    10140 tttttttgtct tggttgtgat gatgtggtct ggttgggcgg tcgttctaga tcggagtaga   10200
attctgtttc aaactacctg gtggatttat taattttgga tctgtatgtg tgtgccatac    10260
atattcatag ttacgaattg aagatgatgg atggaaatat cgatctagga taggtataca    10320
tgttgatgcg ggttttactg atgcatatac agagatgctt tttgttcgct tggttgtgat    10380
gatgtggtgt ggttgggcgg tcgttcattc gttctagatc ggagtagaat actgtttcaa    10440
actacctggt gtatttatta attttggaac tgtatgtgtg tgtcatacat cttcatagtt    10500
acgagtttaa gatggatgga aatatcgatc taggataggt atacatgttg atgtgggttt    10560
tactgatgca tatacatgat ggcatatgca gcatctattc atatgctcta accttgagta    10620
cctatctatt ataataaaca agtatgtttt ataattattt tgatcttgat atacttggat    10680
gatggcatat gcagcagcta tatgtggatt tttttagccc tgccttcata cgctatttat    10740
ttgcttggta ctgtttcttt tgtcgatgct caccctgttg tttggtgtta cttctgcagt    10800
gactaaatag atgcagaagc tgatcaacag cgtgcagaac tacgcctggg gcagcaagac    10860
cgccctgacc gagctgtacg gcatggagaa ccccagcagc cagcccatgg ccgagctgtg    10920
gatgggcgcc caccccaaga gctcaagccg cgtgcagaac gccgccggcg atatcgttag    10980
cctgcgcgag gtgatcgaga cgacaagag caccctgctg ggcgaggccg tggccaagcg     11040
cttcggcgag ctgcccttcc tgttcaaggt gctgtgcgcc gctcagcccc tgagcatcca    11100
ggtgcaccct aacaagcaca acagcgagat cggcttcgcc aaggagaacg ccgccggcat    11160
ccccatggac gccgccgagc gcaactacaa ggaccccaac cacaagcccg agctggtgtt    11220
cgccctgacc cccttcctgg ccatgaacgc cttccgcgag ttcagcgaga tcgttagcct    11280
gctgcagccc gtggccggcg cccacccgc tatcgcccac ttccttcagc agcccgacgc     11340
cgagcgcctg agcgagctgt tcgccagcct gctgaacatg cagggtgagg agaagtcacg    11400
cgccctggca atcctgaaga gcgccctgga cagccagcag ggcgagccct ggcagacaat    11460
ccgcctgatc agcgagttct accccgagga tagcggcctg ttcagccccc tgctgctgaa    11520
```

```
cgtggtgaag ctgaacccocg gcgaggccat gttcctgttc gccgagaccc cccacgccta    11580
cctgcagggc gtggcoctgg aggtgatggc aacagcgac aacgtgctgc gcgccggcct    11640 gaccccaag tacatcgaca tccccgagct ggtggccaac gtgaagttcg aggctaagcc    11700
cgccaaccag ctgctgaccc agcccgtgaa gcagggcgcc gagctggact tccctatccc    11760
cgttgacgac ttcgccttca gcctgcacga cctgagcgac aaggagacca ctatcagcca    11820
gcagagcgcc gcgatcctgt tctgcgtgga gggcgacgcc accctgtgga agggcagcca    11880
gcagctgcag ctgaagcccg gcgagagcgc ctttatcgcc gccaacgaga gccccgtgac    11940
cgtgaagggc cacggccgcc tggcccgcgt gtacaacaag ctgtgatagc tacgtcatgg    12000
gtcgtttaag ctgccgatgt gcctgcgtcg tctggtgccc tctctccata tggaggttgt    12060
caaagtatct gctgttcgtg tcatgagtcg tgtcagtgtt ggtttaataa tggaccggtt    12120
gtgttgtgtg tgcgtactac ccagaactat gacaaatcat gaataagttt gatgtttgaa    12180
attaaagcct gtgctcatta tgttctgtct ttcagttgtc tcctaatatt tgcctgcagg    12240
tactggctat ctaccgtttc ttacttagga ggtgtttgaa tgcactaaaa ctaatagtta    12300
gtggctaaaa ttagttaaaa catccaaaca ccatagctaa tagttgaact attagctatt    12360
tttgaaaaat tagttaatag tgaggtagtt atttgttagc tagctaattc aactaacaat    12420
ttttagccaa ctaacaatta gtttcagtgc attcaaacac ccccttaatg ttaacgtggt    12480
tctatctacc gtctcctaat atatggttga ttgttcggtt tgttgctatg ctattgggtt    12540
ctgattgctg ctagttcttg ctgaatccag aagttctcgt agtatagctc agattcatat    12600
tatttatttg agtgataagt gatccaggtt attactatgt tagctaggtt tttttttacaa    12660 ggataaatta tctgtgatca taattcttat gaaagcttta tgtttcctgg aggcagtggc    12720
atgcaatgca tgacagcaac ttgatcacac cagctgaggt agatacggta acaaggttct    12780
taaatctgtt caccaaatca ttggagaaca cacatacaca ttcttgccag tcttggttag    12840
agaaatttca tgcaaaaatg ccaaagctgt cttgactctt cacttttggc catgagtcgt    12900
gacttagttt ggtttaatgg accggttctc ctagcttgtt ctactcaaaa ctgttgttga    12960
tgcgaataag ttgtgatggt tgatctctgg attttgtttt gctctcaata gtggacgaga    13020
ttagatagct taagcctgca ggcggaccgc ctgcaggccc gggggcgcgc cctaattagc    13080
taacggccag gatcgccgcg tgagccttta gcaactagct agattaatta acgcaatctg    13140
ttattaagtt gtctaagcgt caatttgttt acaccacaat atatcctgcc accagccagc    13200
caacagctcc ccgaccggca gctcggcaca aaatcaccac tcgatacagg cagcccatca    13260
gaattaattc tcatgtttga cagcttatca tcgactgcac ggtgcaccaa tgcttctggc    13320
gtcaggcagc catcggaagc tgtggtatgg ctgtgcaggt cgtaaatcac tgcataattc    13380
gtgtcgctca aggcgcactc ccgttctgga taatgttttt tgcgccgaca tcataacggt    13440
tctggcaaat attctgaaat gagctgttga caattaatca tccggctcgt ataatgtgtg    13500
gaattgtgag cggataacaa tttcacacag gaaacagacc atgagggaag cgttgatcgc    13560
cgaagtatcg actcaactat cagaggtagt tggcgtcatc gagcgccatc tcgaaccgac    13620
gttgctggcc gtacatttgt acggctccgc agtggatggc ggcctgaagc cacacagtga    13680
tattgatttg ctggttacgg tgaccgtaag gcttgatgaa caacgcggc gagctttgat    13740 caacgacctt ttggaaactt cggcttcccc tggagagagc gagattctcc gcgctgtaga    13800
agtcaccatt gttgtgcacg acgacatcat tccgtggcgt tatccagcta agcgcgaact    13860
gcaatttgga gaatggcagc gcaatgacat tcttgcaggt atcttcgagc cagccacgat    13920
```

```
cgacattgat ctggctatct tgctgacaaa agcaagagaa catagcgttg ccttggtagg   13980
tccagcggcg gaggaactct ttgatccggt tcctgaacag gatctatttg aggcgctaaa   14040 tgaaaccttga acgctatgga actcgccgcc cgactgggct ggcgatgagc gaaatgtagt   14100
gcttacgttg tcccgcattt ggtacagcgc agtaaccggc aaaatcgcgc cgaaggatgt   14160
cgctgccgac tgggcaatgg agcgcctgcc ggcccagtat cagcccgtca tacttgaagc   14220
taggcaggct tatcttggac aagaagatcg cttggcctcg cgcgcagatc agttggaaga   14280
atttgttcac tacgtgaaag gcgagatcac caaagtagtc ggcaaataaa gctctagtgg   14340
atctccgtac ccagggatct ggctcgcggc ggacgcacga cgccggggcg agaccatagg   14400
cgatctccta aatcaatagt agctgtaacc tcgaagcgtt tcacttgtaa caacgattga   14460 gaattttttgt cataaaattg aaatacttgg ttcgcatttt tgtcatccgc ggtcagccgc   14520
aattctgacg aactgcccat ttagctggag atgattgtac atccttcacg tgaaaatttc   14580
tcaagcgctg tgaacaaggg ttcagatttt agattgaaag gtgagccgtt gaaacacgtt   14640
cttcttgtcg atgacgacgt cgctatgcgg catcttatta ttgaataccct tacgatccac   14700 gccttcaaag tgaccgcggt agccgacagc acccagttca caagagtact ctcttccgcg   14760
acggtcgatg tcgtggttgt tgatctagat ttaggtcgtg aagatgggct cgagatcgtt   14820
cgtaatctgg cggcaaagtc tgatattcca atcataatta tcagtggcga ccgccttgag   14880
gagacggata aagttgttgc actcgagcta ggagcaagtg attttatcgc taagccgttc   14940
agtatcagag agtttctagc acgcattcgg gttgccttgc gcgtgcgccc caacgttgtc   15000
cgctccaaag accgacggtc tttttgtttt actgactgga cacttaatct caggcaacgt   15060
cgcttgatgt ccgaagctgg cggtgaggtg aaacttacgg caggtgagtt caatcttctc   15120
ctcgcgtttt tagagaaacc ccgcgacgtt ctatcgcgcg agcaacttct cattgccagt   15180
cgagtacgcg acgaggaggt ttatgacagg agtatagatg ttctcatttt gaggctgcgc   15240
cgcaaacttg aggcagatcc gtcaagccct caactgataa aaacagcaag aggtgccggt   15300
tatttctttg acgcggacgt gcaggtttcc cacgggggga cgatggcagc ctgagccaat   15360
tcccagatcc ccgaggaatc ggcgtgagcg gtcgcaaacc atccggcccg gtacaaatcg   15420
gcgcggcgct gggtgatgac ctggtggaga agttgaaggc cgcgcaggcc gcccagcggc   15480
aacgcatcga ggcagaagca cgccccggtg aatcgtggca agcggccgct gatcgaatcc   15540
gcaaagaatc ccggcaaccg ccggcagccg gtgcgccgtc gattaggaag ccgcccaagg   15600
gcgacgagca accagatttt ttcgttccga tgctctatga cgtgggcacc cgcgatagtc   15660
gcagcatcat ggacgtggcc gttttccgtc tgtcgaagcg tgaccgacga gctggcgagg   15720
tgatccgcta cgagcttcca gacgggcacg tagaggtttc gcagggccg gccggcatgg   15780 ccagtgtgtg ggattacgac ctggtactga tggcggtttc ccatctaacc gaatccatga   15840
accgataccg ggaagggaag ggagacaagc ccggccgcgt gttccgtcca cacgttgcgg   15900
acgtactcaa gttctgccgg cgagccgatg gcggaaagca gaaagacgac ctggtagaaa   15960
cctgcattcg gttaaacacc acgcacgttg ccatgcagcg tacgaagaag gccaagaacg   16020
gccgcctggt gacggtatcc gagggtgaag ccttgattag ccgctacaag atcgtaaaga   16080
gcgaaaccgg gcggccggag tacatcgaga tcgagctggc tgattggatg taccgcgaga   16140
tcacagaagg caagaacccg gacgtgctga cggttcaccc cgattacttt ttgatcgatc   16200
ccggcatcgg ccgttttctc taccgcctgg cacgccgcgc cgcaggcaag gcagaagcca   16260
```

```
gatggttgtt caagacgatc tacgaacgca gtggcagcgc cggagagttc aagaagttct  16320
gtttcaccgt gcgcaagctg atcgggtcaa atgacctgcc ggagtacgat ttgaaggagg  16380
aggcggggca ggctggcccg atcctagtca tgcgctaccg caacctgatc gagggcgaag  16440
catccgccgg ttcctaatgt acggagcaga tgctagggca aattgcccta gcaggggaaa  16500
aaggtcgaaa aggtctcttt cctgtggata gcacgtacat tgggaaccca aagccgtaca  16560
ttgggaaccg gaacccgtac attgggaacc caaagccgta cattgggaac cggtcacaca  16620
tgtaagtgac tgatataaaa gagaaaaaag gcgattttc cgcctaaaac tctttaaaac  16680
ttattaaaac tcttaaaacc cgcctggcct gtgcataact gtctggccag cgcacagccg  16740
aagagctgca aaaagcgcct acccttcggt cgctgcgctc cctacgcccc gccgcttcgc  16800
gtcggcctat cgcggccgct ggccgctcaa aaatggctgg cctacggcca ggcaatctac  16860
cagggcgcgg acaagccgcg ccgtcgccac tcgaccgccg gcgctgaggt ctgcctcgtg  16920
aagaaggtgt tgctgactca taccaggcct gaatcgcccc atcatccagc cagaaagtga  16980
gggagccacg gttgatgaga gctttgttgt aggtggacca gttggtgatt ttgaacttt  17040 gctttgccac ggaacggtct gcgttgtcgg gaagatgcgt gatctgatcc ttcaactcag  17100
caaaagttcg atttattcaa caaagccgcc gtcccgtcaa gtcagcgtaa tgctctgcca  17160
gtgttacaac caattaacca attctgatta gaaaaactca tcgagcatca aatgaaactg  17220
caatttattc atatcaggat tatcaatacc atattttga aaaagccgtt tctgtaatga  17280
aggagaaaac tcaccgaggc agttccatag gatggcaaga tcctggtatc ggtctgcgat  17340
tccgactcgt ccaacatcaa tacaacctat taatttcccc tcgtcaaaaa taaggttatc  17400
aagtgagaaa tcaccatgag tgacgactga atccggtgag aatggcaaaa gctctgcatt  17460
aatgaatcgg ccaacgcgcg gggagaggcg gtttgcgtat tgggcgctct tccgcttcct  17520
cgctcactga ctcgctgcgc tcggtcgttc ggctgcggcg agcggtatca gctcactcaa  17580
aggcggtaat acggttatcc acagaatcag gggataacgc aggaaagaac atgtgagcaa  17640
aaggccagca aaaggccagg aaccgtaaaa aggccgcgtt gctggcgttt ttccataggc  17700
tccgcccccc tgacgagcat cacaaaaatc gacgctcaag tcagaggtgg cgaaacccga  17760
caggactata aagataccag gcgtttcccc ctggaagctc cctcgtgcgc tctcctgttc  17820
cgaccctgcc gcttaccgga tacctgtccg cctttctccc ttcgggaagc gtggcgcttt  17880
ctcatagctc acgctgtagg tatctcagtt cggtgtaggt cgttcgctcc aagctgggct  17940
gtgtgcacga acccccgtt cagcccgacc gctgcgcctt atccggtaac tatcgtcttg  18000
agtccaaccc ggtaagacac gacttatcgc cactggcagc agccactggt aacaggatta  18060
gcagagcgag gtatgtaggc ggtgctacag agttcttgaa gtggtggcct aactacggct  18120
acactagaag aacagtattt ggtatctgcg ctctgctgaa gccagttacc ttcggaaaaa  18180
gagttggtag ctcttgatcc ggcaaacaaa ccaccgctgg tagcggtggt ttttttgttt  18240
gcaagcagca gattacgcgc agaaaaaaag gatctcaaga agatcctttg atcttttcta  18300
cggggtctga cgctcagtgg aacgaaaact cacgttaagg gattttggtc atgagattat  18360
caaaaaggat cttcacctag atccttttga tccggaatta                        18400
```

<210> SEQ ID NO 75
<211> LENGTH: 18402
<212> TYPE: DNA
<213> ORGANISM: Artificial Sequence
<220> FEATURE:
<223> OTHER INFORMATION: Construct 24194

-continued

```
<220> FEATURE:
<221> NAME/KEY: misc_feature
<222> LOCATION: (4)..(259)
<223> OTHER INFORMATION: bNRB-05
<220> FEATURE:
<221> NAME/KEY: misc_feature
<222> LOCATION: (101)..(125)
<223> OTHER INFORMATION: bNRB-01-01
<220> FEATURE:
<221> NAME/KEY: enhancer
<222> LOCATION: (168)..(259)
<223> OTHER INFORMATION: eNOS-01
<220> FEATURE:
<221> NAME/KEY: enhancer
<222> LOCATION: (292)..(485)
<223> OTHER INFORMATION: eFMV-06
<220> FEATURE:
<221> NAME/KEY: enhancer
<222> LOCATION: (492)..(784)
<223> OTHER INFORMATION: e35S-11
<220> FEATURE:
<221> NAME/KEY: promoter
<222> LOCATION: (791)..(2592)
<223> OTHER INFORMATION: prSoUbi4-02
<220> FEATURE:
<221> NAME/KEY: misc_feature
<222> LOCATION: (1170)..(1234)
<223> OTHER INFORMATION: u5SoUbi4-02
<220> FEATURE:
<221> NAME/KEY: Intron
<222> LOCATION: (1235)..(2592)
<223> OTHER INFORMATION: iSoUbi4-02
<220> FEATURE:
<221> NAME/KEY: misc_feature
<222> LOCATION: (2607)..(2657)
<223> OTHER INFORMATION: NLS
<220> FEATURE:
<221> NAME/KEY: gene
<222> LOCATION: (2607)..(6827)
<223> OTHER INFORMATION: CRISPR associated 9
<220> FEATURE:
<221> NAME/KEY: misc_feature
<222> LOCATION: (2610)..(2610)
<223> OTHER INFORMATION: +4G
<220> FEATURE:
<221> NAME/KEY: misc_feature
<222> LOCATION: (2611)..(2611)
<223> OTHER INFORMATION: +5C
<220> FEATURE:
<221> NAME/KEY: mutation
<222> LOCATION: (6147)..(6149)
<223> OTHER INFORMATION: L to V mutation
<220> FEATURE:
<221> NAME/KEY: mutation
<222> LOCATION: (6192)..(6194)
<223> OTHER INFORMATION: I to V mutation
<220> FEATURE:
<221> NAME/KEY: misc_feature
<222> LOCATION: (6762)..(6824)
<223> OTHER INFORMATION: NLS
<220> FEATURE:
<221> NAME/KEY: terminator
<222> LOCATION: (6834)..(7835)
<223> OTHER INFORMATION: tZmMTL-01
<220> FEATURE:
<221> NAME/KEY: misc_feature
<222> LOCATION: (7836)..(7847)
<223> OTHER INFORMATION: xSTOPS-01
<220> FEATURE:
<221> NAME/KEY: promoter
<222> LOCATION: (7855)..(8216)
<223> OTHER INFORMATION: prTaU6-01
<220> FEATURE:
<221> NAME/KEY: misc_feature
<222> LOCATION: (8217)..(8322)
<223> OTHER INFORMATION: guide RNA TaCenH3-01
<220> FEATURE:
<221> NAME/KEY: misc_feature
<222> LOCATION: (8218)..(8237)
```

```
<223> OTHER INFORMATION: xTaCenH3 target-01
<220> FEATURE:
<221> NAME/KEY: misc_feature
<222> LOCATION: (8238)..(8249)
<223> OTHER INFORMATION: crRNA-01
<220> FEATURE:
<221> NAME/KEY: misc_feature
<222> LOCATION: (8254)..(8322)
<223> OTHER INFORMATION: tracrRNA-01
<220> FEATURE:
<221> NAME/KEY: promoter
<222> LOCATION: (8323)..(8684)
<223> OTHER INFORMATION: prTaU6-01
<220> FEATURE:
<221> NAME/KEY: misc_feature
<222> LOCATION: (8685)..(8790)
<223> OTHER INFORMATION: guide RNA TaCenH3-02
<220> FEATURE:
<221> NAME/KEY: misc_feature
<222> LOCATION: (8686)..(8705)
<223> OTHER INFORMATION: xTaCenH3 target-02
<220> FEATURE:
<221> NAME/KEY: misc_feature
<222> LOCATION: (8706)..(8717)
<223> OTHER INFORMATION: crRNA-01
<220> FEATURE:
<221> NAME/KEY: misc_feature
<222> LOCATION: (8722)..(8790)
<223> OTHER INFORMATION: tracrRNA-01
<220> FEATURE:
<221> NAME/KEY: misc_feature
<222> LOCATION: (8797)..(8808)
<223> OTHER INFORMATION: xSTOPS-01
<220> FEATURE:
<221> NAME/KEY: promoter
<222> LOCATION: (8809)..(10801)
<223> OTHER INFORMATION: prUbi1-10
<220> FEATURE:
<221> NAME/KEY: TATA_signal
<222> LOCATION: (9679)..(9687)
<223> OTHER INFORMATION: TATA box
<220> FEATURE:
<221> NAME/KEY: Intron
<222> LOCATION: (9792)..(10801)
<223> OTHER INFORMATION: iUbi1-02-01
<220> FEATURE:
<221> NAME/KEY: gene
<222> LOCATION: (10813)..(11991)
<223> OTHER INFORMATION: cPMI-12
<220> FEATURE:
<221> NAME/KEY: terminator
<222> LOCATION: (11996)..(13030)
<223> OTHER INFORMATION: tUbi1-01
<220> FEATURE:
<221> NAME/KEY: misc_feature
<222> LOCATION: (13074)..(13085)
<223> OTHER INFORMATION: xSTOPS-01
<220> FEATURE:
<221> NAME/KEY: misc_feature
<222> LOCATION: (13086)..(13125)
<223> OTHER INFORMATION: xTAG-02
<220> FEATURE:
<221> NAME/KEY: misc_feature
<222> LOCATION: (13134)..(13263)
<223> OTHER INFORMATION: bNLB-05
<220> FEATURE:
<221> NAME/KEY: misc_feature
<222> LOCATION: (13169)..(13193)
<223> OTHER INFORMATION: bNLB-01-01
<220> FEATURE:
<221> NAME/KEY: gene
<222> LOCATION: (13543)..(14331)
<223> OTHER INFORMATION: cSpec-03
<220> FEATURE:
<221> NAME/KEY: promoter
<222> LOCATION: (14426)..(14556)
<223> OTHER INFORMATION: prVirG-01
<220> FEATURE:
<221> NAME/KEY: gene
```

```
<222> LOCATION: (14631)..(15356)
<223> OTHER INFORMATION: cVirG-01
<220> FEATURE:
<221> NAME/KEY: gene
<222> LOCATION: (15386)..(16459)
<223> OTHER INFORMATION: cRepA-03
<220> FEATURE:
<221> NAME/KEY: misc_feature
<222> LOCATION: (16502)..(16906)
<223> OTHER INFORMATION: oVS1-02
<220> FEATURE:
<221> NAME/KEY: misc_feature
<222> LOCATION: (17584)..(18390)
<223> OTHER INFORMATION: oCOLE-06

<400> SEQUENCE: 75
```

| | | | | | |
|---|---|---|---|---|---|
| attcctgtgg | ttggcatgca | catacaaatg | gacgaacgga | taaacctttt | cacgcccttt | 60 |
| taaatatccg | attattctaa | taaacgctct | tttctcttag | gtttacccgc | caatatatcc | 120 |
| tgtcaaacac | tgatagttta | aactgaaggc | gggaaacgac | aatctgatca | tgagcggaga | 180 |
| attaagggag | tcacgttatg | acccccgccg | atgacgcggg | acaagccgtt | ttacgtttgg | 240 |
| aactgacaga | accgcaacgc | tgcaggaatt | ggccgcagcg | gccatttaaa | tagctgcttg | 300 |
| tggggaccaa | acaaaaaagg | aatggtgcag | aattgttagg | cgcacctacc | aaaagcaact | 360 |
| ttgcctttat | tgcaaagata | agcagattc | ctctagtaca | agtggggaac | aaaataacgt | 420 |
| ggaaaagagc | tgtcctgaca | gcccactcac | tattgcgttt | gacgaacgca | gtgacgacca | 480 |
| caaaactcga | gactttcaa | caaagggtat | tatccggaaa | cctcctcgga | ttccattgcc | 540 |
| cagctatctg | tcactttatt | gtgaagatag | tggaaaagga | aggtggctcc | tacaaatgcc | 600 |
| atcattgcga | taaggaaag | gctatcgttg | aagatgcctc | tgccgacagt | ggtcccaaag | 660 |
| atggacccc | acccacgagg | agcatcgtgg | aaaaagaaga | cgttccaacc | acgtcttcaa | 720 |
| agcaagtgga | ttgatgtgat | atctccactg | acgtaagggt | tgacgaacaa | tcccactatc | 780 |
| cttcggaccc | gaattcatta | tgtggtctag | gtaggttcta | tatataagaa | aacttgaaat | 840 |
| gttctaaaaa | aaaattcaag | cccatgcatg | attgaagcaa | acggtatagc | aacggtgtta | 900 |
| acctgatcta | gtgatctctt | gcaatcctta | acggccacct | accgcaggta | gcaaacggcg | 960 |
| tccccctcct | cgatatctcc | gcggcgacct | ctggctttt | ccgcggaatt | gcgcggtggg | 1020 |
| gacggattcc | acgagaccgc | gacgcaaccg | cctctcgccg | ctgggcccca | caccgctcgg | 1080 |
| tgccgtagcc | tcacgggact | ctttctccct | cctccccgt | tataaattgg | cttcatcccc | 1140 |
| tccttgcctc | atccatccaa | atcccagtcc | ccaatcccat | cccttcgtag | gagaaattca | 1200 |
| tcgaagctaa | gcgaatcctc | gcgatcctct | caaggtactg | cgagttttcg | atccccctct | 1260 |
| cgaccctcg | tatgtttgtg | tttgtcgtag | cgtttgatta | ggtatgcttt | ccctgtttgt | 1320 |
| gttcgtcgta | gcgtttgatt | aggtatgctt | tccctgttcg | tgttcatcgt | agtgtttgat | 1380 |
| taggtcgtgt | gaggcgatgg | cctgctcgcg | tccttcgatc | tgtagtcgat | ttgcgggtcg | 1440 |
| tggtgtagat | ctgcgggctg | tgatgaagtt | atttggtgtg | atctgctcgc | ctgattctgc | 1500 |
| gggttggctc | gagtagatat | gatggttgga | ccggttggtt | cgtttaccgc | gctagggttg | 1560 |
| ggctgggatg | atgttgcatg | cgccgttgcg | cgtgatcccg | cagcaggact | tgcgtttgat | 1620 |
| tgccagatct | cgttacgatt | atgtgatttg | gtttggactt | tttagatctg | tagcttctgc | 1680 |
| ttatgtgcca | gatgcgccta | ctgctcatat | gcctgatgat | aatcataaat | ggctgtggaa | 1740 |
| ctaactagtt | gattgcggag | tcatgtatca | gctacaggtg | tagggactag | ctacaggtgt | 1800 |
| agggacttgc | gtctaattgt | ttggtccttt | actcatgttg | caattatgca | atttagttta | 1860 |

```
gattgtttgt tccactcatc taggctgtaa aagggacact gcttagattg ctgtttaatc    1920
tttttagtag attatattat attggtaact tattacccct attacatgcc atacgtgact    1980
tctgctcatg cctgatgata atcatagatc actgtggaat taattagttg attgttgaat    2040
catgtttcat gtacatacca cggcacaatt gcttagttcc ttaacaaatg caaattttac    2100
tgatccatgt atgatttgcg tggttctcta atgtgaaata ctatagctac ttgttagtaa    2160
gaatcaggtt cgtatgctta atgctgtatg tgccttctgc tcatgcctga tgataatcat    2220
atatcactgg aattaattag ttgatcgttt aatcatatat caagtacata ccatgccaca    2280
attttagtc acttaaccca tgcagattga actggtccct gcatgttttg ctaaattgtt     2340
ctattctgat tagaccatat atcatgtatt ttttttggt aatggttctc ttatttaaa      2400
tgctatatag ttctggtact tgttagaaag atctgcttca tagtttagtt gcctatccct    2460
cgaattagga tgctgagcag ctgatcctat agctttgttt catgtatcaa ttcttttgtg    2520
ttcaacagtc agttttttgtt agattcattg taacttatgg tcgcttactc ttctggtcct   2580
caatgcttgc agcctagtaa gccgccatgg ccccaaagaa gaagaggaag gtcggcatcc    2640
acggcgtccc agctgcgatg acaagaagt actccatcgg cctcgacatc ggcaccaaca    2700
gcgtgggctg ggccgtcatc accgacgagt acaaggtgcc atccaagaag ttcaaggtcc    2760
tgggcaacac cgaccgccac agcatcaaga gaaacctcat cggcgctctc ctgttcgact   2820
ccggcgagac ggctgaggct accaggctca gcgcaccgc caggaggagg tacaccagga    2880
ggaagaacag gatctgctac ctccaagaga tcttctccaa cgagatggcc aaggtggacg    2940
actccttctt ccaccgcctg gaggagagct tcctcgtcga ggaggacaag aagcacgaga    3000
ggcacccaat cttcggcaac atcgtggacg aggtcgccta ccacgagaag tacccaacca    3060
tctaccacct gaggaagaag ctcgtggact ccaccgacaa ggccgacctc cgcctgatct    3120
acctcgccct ggcccacatg atcaagttca ggggccactt cctgatcgag ggcgacctca    3180
acccagacaa cagcgacgtg gacaagctgt tcatccaact cgtccagacc tacaaccagc    3240
tcttcgagga gaacccgatc aacgcttccg gcgtggacgc taaggctatc ctgagcgcta    3300
ggctctccaa gagcaggagg ctcgagaacc tgatcgccca gctcccaggc gagaagaaga    3360
acggcctgtt cggcaaccct atcgctctct ccctgggcct caccccaaac ttcaagagca    3420
acttcgacct cgccgaggac gccaagctgc aactctccaa ggacacctac gacgacgacc    3480
tggacaacct cctggcccag atcggcgacc aatacgccga cctgttcctc gccgccaaga    3540
acctgtccga cgccatcctc ctgagcgaca tcctccgcgt gaacaccgag atcaccaagg    3600
ccccactctc cgccagcatg atcaagcgct acgacgagca ccaccaggac ctgaccctcc    3660
tgaaggccct ggtcaggcaa cagctcccag agaagtacaa ggagatcttc ttcgaccaga    3720
gcaagaacgg ctacgctggc tacatcgacg gcggcgcctc ccaagaggag ttctacaagt    3780
tcatcaagcc aatcctggag aagatggacg gcaccgagga gctcctggtg aagctcaaca    3840
gggaggacct cctgaggaag cagcgcacct tcgacaacgg cagcatccca caccaaatcc    3900
acctcggcga gctgcacgct atcctgagga ggcaagagga cttctaccca ttcctcaagg    3960
acaacaggga gaagatcgag aagatcctga ccttccgcat ccctactac gtcggccac     4020
tcgctagggg caactccagg ttcgcttgga tgacccgcaa gagcgaggag acgatcaccc    4080
cgtggaactt cgaggaggtc gtcgacaagg gcgcttccgc tcagagcttc atcgagagga    4140
tgaccaactt cgacaagaac ctgccaaacg agaaggtgct cccaaagcac tccctcctgt    4200
acgagtactt caccgtctac aacgagctca ccaaggtgaa gtatgtgacc gagggcatgc    4260
```

```
gcaagccagc cttcctgagc ggcgagcaga agaaggccat cgtggacctc ctgttcaaga    4320
ccaacaggaa ggtgaccgtc aagcaactca aggaggacta cttcaagaag atcgagtgct    4380
tcgactccgt ggagatcagc ggcgtcgagg accgcttcaa cgcctccctc ggcacctacc    4440
acgacctcct gaagatcatc aaggacaagg acttcctgga caacgaggag aacgaggaca    4500
tcctcgagga catcgtgctg accctcaccc tgttcgagga cagggagatg atcgaggagc    4560
gcctgaagac ctacgcccac ctcttcgacg acaaggtcat gaagcaactc aagaggagga    4620
ggtacaccgg ctggggcagg ctgagccgca agctcatcaa cggcatccgc gacaagcagt    4680
ccggcaagac catcctcgac ttcctgaaga gcgacggctt cgccaacagg aacttcatgc    4740
aactgatcca cgacgactcc ctcaccttca aggaggacat ccaaaaggct caggtgtccg    4800
gccagggcga cagcctgcac gagcacatcg ctaacctcgc tggcagccca gccatcaaga    4860
agggcatcct gcagaccgtg aaggtcgtcg acgagctcgt gaaggtcatg ggcaggcaca    4920
agccagagaa catcgtcatc gagatggccc gcgagaacca gaccacccag aagggccaaa    4980
agaactccag ggagcgcatg aagcgcatcg aggagggcat caaggagctg ggcagccaaa    5040
tcctcaagga gcacccagtg gagaacaccc aactgcagaa cgagaagctc tacctgtact    5100
acctccagaa cggcagggac atgtatgtgg accaagagct ggacatcaac cgcctctccg    5160
actacgacgt ggaccacatc gtcccacagt ccttcctgaa ggacgacagc atcgacaaca    5220
aggtgctcac caggagcgac aagaaccgcg gcaagtccga caacgtccca agcgaggagg    5280
tggtcaagaa gatgaaaaac tactggaggc agctcctgaa cgccaagctg atcacccaaa    5340
ggaagttcga caacctcacc aaggctgaga ggggcggcct ctccgagctg gacaaggccg    5400
gcttcattaa aaggcagctg gtggagacgc gccaaatcac caagcacgtc gcccaaatcc    5460
tcgacagccg catgaacacc aagtacgacg agaacgacaa gctgatcagg gaggtgaagg    5520
tcatcacccT gaagtccaag ctcgtgagcg acttcaggaa ggacttccag ttctacaagg    5580
tccgcgagat caataattac caccacgccc acgacgctta cctcaacgct gtggtcggca    5640
ccgccctgat taaaaagtac ccaaagctcg agtccgagtt cgtgtacggc gactacaagg    5700
tgtacgacgt ccgcaagatg atcgccaagt ccgagcaaga gatcggcaag gccaccgcca    5760
agtacttctt ctacagcaac atcatgaact tcttcaagac cgagatcacc ctggccaacg    5820
gcgagatcag gaagcgccca ctcatcgaga cgaacgcgga gacgggcgag atcgtgtggg    5880
acaagggcag ggacttcgcc accgtgcgca aggtcctctc catgccacag gtgaacatcg    5940
tcaagaagac cgaggtccaa accggcggct tctccaagga gagcatcctg ccaaagagga    6000
acagcgacaa gctcatcgcc cgcaagaagg actgggatcc aaagaagtac ggcggcttcg    6060 actcccaac cgtggcctac agcgtcctcg tggtcgccaa ggtggagaag ggcaagtcca    6120
agaagctgaa gagcgtgaag gagctcgtcg gcatcaccat catggagagg tccagcttcg    6180
agaagaaccc agtggacttc ctcgaggcca gggctacaa ggaggtcaag aaggacctga    6240
tcattaaact cccaaagtac agcctcttcg agctggagaa cggcaggaag cgcatgctgg    6300
cttccgctgg cgagctccaa aagggcaacg agctcgccct gccatccaag tatgtgaact    6360
tcctctacct ggcctcccac tacgagaagc tcaagggcag cccagaggac aacgagcaaa    6420
agcagctgtt cgtcgagcag cacaagcact acctcgacga gatcatcgag caaatctccg    6480
agttcagcaa gcgcgtgatc ctcgccgacg ccaacctgga caaggtcctc tccgcctaca    6540
acaagcacag ggacaagcca atccgcgagc aggccgagaa catcatccac ctcttcaccc    6600
```

```
tgaccaacct cggcgctcca gctgccttca agtacttcga caccaccatc gacaggaagc   6660
gctacacctc caccaaggag gtgctggacg ccaccctcat ccaccagtcc atcaccggcc   6720
tctacgagac gaggatcgac ctgagccaac tcggcggcga ctccagccca ccaaagaaga   6780
agaggaaggt cagctggaag gacgcttccg gctggagccg catgtgaggt acctcacatc   6840
gatcgacgac caaggatatg attattatct atctagcttg tggtggtggt tgaacaataa   6900
taagcgaggc cgagctggct gccatacata ggtattgtgt ggtgtgtgtg agagagagag   6960
aaacagagtt cttcagtttg ctatctctct ctgcatgttt ggcgtcagtc tttgtgctca   7020
tgtacgtacg tgtgtctacc tgcatgttgg ttgatccgat tgcatctgct gtaaccatat   7080
attaattggt ccacgatgat atgatttgat actatatata tactaaaacc ggacttctta   7140
ttataatact tgtagtatat aagtttctta cgcccgcaat tgatcgattc agaaggagtt   7200
ctagctagct aaaacatgca gattcagaat atcagatttt taggactact ggagatccag   7260
aaccttcgtg tccttgtacc cgtgattttg gatccccttt ctccccacta caatcgttgg   7320
cgcaatcttg ttctgctcgc ctagaatggt acgccctcac cgaccatgtc ctcgccgatg   7380
cctaccccgc cacgccatct ggatggtgca tgaatgtcgt cgttttgtcc tggatgctag   7440
gcacactctc ccccgagttg atggagcctc ctcgcacctc tggtggcact cgccgcgcc    7500 tggcttgcca tcgaggagca attcctcggc aatcgcgaag ctcgcacact tcgtctcgac   7560
gccgagttcc atgtcttcat gtaggcgatc tcttcgtcag cgactattgt ctattgacgc   7620
aagatgaagg ggatggacga ggcccttggt gatcttggtg aggtcatcca tgaccgtacc   7680
cttgtcctaa acgtgttgtg tggtctgaat gagaggtttg cccacataaa ggtccacttc   7740
aagcactcga atccgttccc ctccttcacc gacgtttgta atgatctcat ccttgaggag   7800
atcgactcca gcgcgcctcc tccgcctccg accacctaat tagctaaggg acccgaccaa   7860
gcccgttatt ctgacagttc tggtgctcaa cacatttata tttatcaagg agcacattgt   7920
tactcactgc taggagggaa tcgaactagg aatattgatc agaggaacta cgagagagct   7980
gaagataact gccctctagc tctcactgat ctgggtcgca tagtgagatg cagcccacgt   8040
gagttcagca acggtctagc gctgggcttt taggcccgca tgatcgggct tttgtcgggt   8100
ggtcgacgtg ttcacgattg gggagagcaa cgcagcagtt cctcttagtt tagtcccacc   8160
tcgcctgtcc agcagagttc tgaccggttt ataaactcgc ttgctgcatc agacttgacg   8220
tcggcgacac cggtgcggtt ttagagctag aaatagcaag ttaaaataag gctagtccgt   8280
tatcaacttg aaaaagtggc accgagtcgg tgcttttttt ttgaccaagc ccgttattct   8340
gacagttctg gtgctcaaca catttatatt tatcaaggag cacattgtta ctcactgcta   8400
ggagggaatc gaactaggaa tattgatcag aggaactacg agagagctga agataactgc   8460
cctctagctc tcactgatct gggtcgcata gtgagatgca gcccacgtga gttcagcaac   8520
ggtctagcgc tgggctttta ggcccgcatg atcgggcttt tgtcgggtgg tcgacgtgtt   8580
cacgattggg gagagcaacg cagcagttcc tcttagttta gtcccacctc gcctgtccag   8640
cagagttctg accggtttat aaactcgctt gctgcatcag acttgcttgt gggagcaggg   8700
gcaacgtttt agagctagaa atagcaagtt aaaataaggc tagtccgtta tcaacttgaa   8760
aaagtggcac cgagtcggtg cttttttttt cctaggctaa ttagctaact gcagtgcagc   8820
gtgacccggt cgtgcccctc tctagagata atgagcattg catgtctaag ttataaaaaa   8880
ttaccacata tttttttttgt cacacttgtt tgaagtgcag tttatctatc tttatacata   8940
tatttaaact ttactctacg aataatataa tctatagtac tacaataata tcagtgtttt   9000
```

```
agagaatcat ataaatgaac agttagacat ggtctaaagg caaattgagt attttgacaa   9060
caggactcta cagttttatc tttttagtgt gcatgtgttc tcctttttt ttgcaaatag    9120
cttcacctat ataatacttc atccatttta ttagtacatc catttagggt ttagggttaa   9180
tggttttat agactaattt ttttagtaca tctattttat tctattttag cctctaaatt    9240
aagaaaacta aaactctatt ttagttttt tatttaataa tttagatata aaatagaata    9300
aaataaagtg actaaaaatt aaacaaatac cctttaagaa attaaaaaaa ctaaggaaac   9360
attttcttg tttcgagtag ataatgccag cctgttaaac gccgtcgacg agtctaacgg    9420
acaccaacca gcgaaccagc agcgtcgcgt cgggccaagc gaagcagacg gcacggcatc   9480
tctgtcgctg cctctggacc cctctcgaga gttccgctcc accgttggac ttgctccgct   9540
gtcggcatcc agaaattgcg tggcggagcg gcagacgtga gccggcacgg caggcggcct   9600
cctcctcctc tcacggcacc ggcagctacg ggggattcct ttcccaccgc tccttcgctt   9660
tcccttcctc gcccgccgta ataaatagac accccctcca caccctcttt ccccaacctc   9720
gtgttgttcg gagcgcacac acacacaacc agatctcccc caaatccacc cgtcggcacc   9780
tccgcttcaa ggtacgccgc tcgtcctccc cccccccccc tctctacctt ctctagatcg   9840
gcgttccggt ccatggttag ggcccggtag ttctacttct gttcatgttt gtgttagatc   9900
cgtgtttgtg ttagatccgt gctgctagcg ttcgtacacg gatgcgacct gtacgtcaga   9960
cacgttctga ttgctaactt gccagtgttt ctctttgggg aatcctggga tggctctagc   10020
cgttccgcag acgggatcga tttcatgatt ttttttgttt cgttgcatag ggtttggttt   10080
gcccttttcc tttatttcaa tatatgccgt gcacttgttt gtcgggtcat cttttcatgc   10140
tttttttgt cttggttgtg atgatgtggt ctggttgggc ggtcgttcta gatcggagta    10200
gaattctgtt tcaaactacc tggtggattt attaattttg gatctgtatg tgtgtgccat   10260
acatattcat agttacgaat tgaagatgat ggatggaaat atcgatctag ataggtata    10320
catgttgatg cgggttttac tgatgcatat acagagatgc ttttgttcg cttggttgtg    10380
atgatgtggt gtggttgggc ggtcgttcat tcgttctaga tcggagtaga atactgtttc   10440
aaactacctg gtgtatttat taattttgga actgtatgtg tgtgtcatac atcttcatag   10500
ttacgagttt aagatggatg gaaatatcga tctaggatag gtatacatgt tgatgtgggt   10560
tttactgatg catatacatg atggcatatg cagcatctat tcatatgctc taaccttgag   10620
tacctatcta ttataataaa caagtatgtt ttataattat tttgatcttg atatacttgg   10680
atgatggcat atgcagcagc tatatgtgga ttttttttagc cctgccttca tacgctatt    10740
atttgcttgg tactgtttct tttgtcgatg ctcaccctgt tgtttggtgt tacttctgca   10800
gtgactaaat agatgcagaa gctgatcaac agcgtcaga actacgcctg gggcagcaag   10860
accgccctga ccgagctgta cggcatggag aaccccagca gccagcccat ggccgagctg   10920
tggatgggcg cccaccccaa gagctcaagc gcgtcagaa cgccgccgg cgatatcgtt     10980
agcctgcgcg acgtgatcga gagcgacaag agcaccctgc tgggcgaggc cgtggccaag   11040
cgcttcggcg agctgcccctt cctgttcaag gtgctgtgcg ccgctcagcc cctgagcatc   11100
caggtgcacc ctaacaagca caacagcgag atcggcttcg ccaaggagaa cgccgccggc   11160
atccccatgg acgccgccga gcgcaactac aaggaccccca accacaagcc cgagctggtg   11220
ttcgccctga ccccttcct ggccatgaac gccttccgcg agttcagcga gatcgttagc   11280
ctgctgcagc ccgtggccgg cgcccacccc gctatcgccc acttccttca gcagcccgac   11340
```

```
gccgagcgcc tgagcgagct gttcgccagc ctgctgaaca tgcagggtga ggagaagtca   11400
cgcgccctgg ccatcctgaa gagcgccctg gacagccagc agggcgagcc ctggcagaca   11460
atccgcctga tcagcgagtt ctaccccgag gatagcggcc tgttcagccc cctgctgctg   11520
aacgtggtga agctgaaccc cggcgaggcc atgttcctgt cgccgagac cccccacgcc    11580 tacctgcagg gcgtggccct ggaggtgatg gccaacagcg acaacgtgct gcgcgccggc   11640
ctgaccccca agtacatcga catccccgag ctggtggcca acgtgaagtt cgaggctaag   11700
cccgccaacc agctgctgac ccagcccgtg aagcagggcg ccgagctgga cttccctatc   11760
cccgttgacg acttcgcctt cagcctgcac gacctgagcg acaaggagac cactatcagc   11820
cagcagagcg ccgcgatcct gttctgcgtg gagggcgacg ccaccctgtg aagggcagc    11880 cagcagctgc agctgaagcc cggcgagagc gcctttatcg ccgccaacga gagcccccgtg   11940 accgtgaagg gccacggccg cctggcccgc gtgtacaaca agctgtgata gctacgtcat   12000
gggtcgttta agctgccgat gtgcctgcgt cgtctggtgc cctctctcca tatggaggtt   12060
gtcaaagtat ctgctgttcg tgtcatgagt cgtgtcagtg ttggtttaat aatggaccgg   12120
ttgtgttgtg tgtgcgtact acccagaact atgacaaatc atgaataagt ttgatgtttg   12180
aaattaaagc ctgtgctcat tatgttctgt cttctcagttg tctcctaata tttgcctgca   12240
ggtactggct atctaccgtt tcttacttag gaggtgtttg aatgcactaa aactaatagt   12300
tagtggctaa aattagttaa aacatccaaa caccatagct aatagttgaa ctattagcta   12360
tttttggaaa attagttaat agtgaggtag ttatttgtta gctagctaat tcaactaaca   12420 attttagcc aactaacaat tagtttcagt gcattcaaac accccttaa tgttaacgtg     12480 gttctatcta ccgtctccta atatatggtt gattgttcgg tttgttgcta tgctattggg   12540
ttctgattgc tgctagttct tgctgaatcc agaagttctc gtagtatagc tcagattcat   12600 attattat tgagtgataa gtgatccagg ttattactat gttagctagg ttttttttac     12660
aaggataaat tatctgtgat cataattctt atgaaagctt tatgtttcct ggaggcagtg   12720
gcatgcaatg catgacagca acttgatcac accagctgag gtagatacgg taacaaggtt   12780
cttaaatctg ttcaccaaat cattggagaa cacacataca cattcttgcc agtcttggtt   12840
agagaaattt catgacaaaa tgccaaagct gtcttgactc ttcacttttg gccatgagtc   12900
gtgacttagt ttggtttaat ggaccggttc tcctagcttg ttctactcaa aactgttgtt   12960
gatgcgaata agttgtgatg gttgatctct ggattttgtt ttgctctcaa tagtggacga   13020
gattagatag cttaagcctg caggcggacc gcctgcaggc ccgggggcgc gccctaatta   13080
gctaacggcc aggatcgccg cgtgagcctt tagcaactag ctagattaat taacgcaatc   13140
tgttattaag ttgtctaagc gtcaatttgt ttacaccaca atatatcctg ccaccagcca   13200
gccaacagct ccccgaccgg cagctcggca caaaatcacc actcgataca ggcagcccat   13260
cagaattaat tctcatgttt gacagcttat catcgactgc acggtgcacc aatgcttctg   13320
gcgtcaggca gccatcggaa gctgtggtat ggctgtgcag gtcgtaaatc actgcataat   13380
tcgtgtcgct caaggcgcac tcccgttctg gataatgttt tttgcgccga catcataacg   13440
gttctggcaa atattctgaa atgagctgtt gacaattaat catccggctc gtataatgtg   13500
tggaattgtg agcggataac aatttcacac aggaaacaga ccatgaggga agcgttgatc   13560
gccgaagtat cgactcaact atcagaggta gttggcgtca tcgagcgcca tctcgaaccg   13620
acgttgctgg ccgtacattt gtacggctcc gcagtggatg gcggcctgaa gccacacagt   13680
gatattgatt tgctggttac ggtgaccgta aggcttgatg aaacaacgcg gcgagctttg   13740
```

```
atcaacgacc ttttggaaac ttcggcttcc cctggagaga gcgagattct ccgcgctgta   13800
gaagtcacca ttgttgtgca cgacgacatc attccgtggc gttatccagc taagcgcgaa   13860
ctgcaatttg gagaatggca gcgcaatgac attcttgcag gtatcttcga gccagccacg   13920
atcgacattg atctggctat cttgctgaca aaagcaagag aacatagcgt tgccttggta   13980
ggtccagcgg cggaggaact ctttgatccg gttcctgaac aggatctatt tgaggcgcta   14040
aatgaaacct taacgctatg gaactcgccg cccgactggg ctggcgatga gcgaaatgta   14100
gtgcttacgt tgtcccgcat ttggtacagc gcagtaaccg gcaaaatcgc gccgaaggat   14160
gtcgctgccg actgggcaat ggagcgcctg ccggcccagt atcagcccgt catacttgaa   14220
gctaggcagg cttatcttgg acaagaagat cgcttggcct cgcgcgcaga tcagttggaa   14280
gaatttgttc actacgtgaa aggcgagatc accaaagtag tcggcaaata agctctagt   14340 ggatctccgt acccagggat ctggctcgcg gcggacgcac gacgccgggg cgagaccata   14400
ggcgatctcc taaatcaata gtagctgtaa cctcgaagcg tttcacttgt aacaacgatt   14460
gagaattttt gtcataaaat tgaaatactt ggttcgcatt tttgtcatcc gcggtcagcc   14520
gcaattctga cgaactgccc atttagctgg agatgattgt acatccttca cgtgaaaatt   14580
tctcaagcgc tgtgaacaag ggttcagatt ttagattgaa aggtgagccg ttgaaacacg   14640
ttcttcttgt cgatgacgac gtcgctatgc ggcatcttat tattgaatac cttacgatcc   14700
acgccttcaa agtgaccgcg gtagccgaca gcacccagtt cacaagagta ctctcttccg   14760
cgacggtcga tgtcgtggtt gttgatctag atttaggtcg tgaagatggg ctcgagatcg   14820
ttcgtaatct ggcggcaaag tctgatattc caatcataat tatcagtggc gaccgccttg   14880
aggagacgga taaagttgtt gcactcgagc taggagcaag tgattttatc gctaagccgt   14940
tcagtatcag agagtttcta gcacgcattc gggttgcctt gcgcgtgcgc cccaacgttg   15000
tccgctccaa agaccgacgg tcttttttgtt ttactgactg gacacttaat ctcaggcaac   15060
gtcgcttgat gtccgaagct ggcggtgagg tgaaacttac ggcaggtgag ttcaatcttc   15120
tcctcgcgtt tttagagaaa ccccgcgacg ttctatcgcg cgagcaactt ctcattgcca   15180
gtcgagtacg cgacgaggag gtttatgaca ggagtataga tgttctcatt ttgaggctgc   15240
gccgcaaact tgaggcagat ccgtcaagcc ctcaactgat aaaaacagca agaggtgccg   15300
gttatttctt tgacgcggac gtgcaggttt cgcacggggg gacgatggca gcctgagcca   15360
attcccagat ccccgaggaa tcggcgtgag cggtcgcaaa ccatccggcc cggtacaaat   15420
cggcgcggcg ctgggtgatg acctggtgga gaagttgaag gccgcgcagg ccgcccagcg   15480
gcaacgcatc gaggcagaag cacgccccgg tgaatcgtgg caagcggccg ctgatcgaat   15540
ccgcaaagaa tcccggcaac cgccggcagc cggtgcgccg tcgattagga gccgcccaa   15600 gggcgacgag caaccagatt ttttcgttcc gatgctctat gacgtgggca cccgcgatag   15660
tcgcagcatc atggacgtgg ccgttttccg tctgtcgaag cgtgaccgac gagctggcga   15720
ggtgatccgc tacgagcttc cagacgggca cgtagaggtt tccgcagggc cggccggcat   15780
ggccagtgtg tgggattacg acctggtact gatggcggtt tcccatctaa ccgaatccat   15840
gaaccgatac cggaaggga agggagacaa gcccggccgc gtgttccgtc cacacgttgc   15900
ggacgtactc aagttctgcc ggcgagccga tggcggaaag cagaaagacg acctggtaga   15960
aacctgcatt cggttaaaca ccacgcacgt tgccatgcag cgtacgaaga aggccaagaa   16020
cggccgcctg gtgacggtat ccgagggtga agccttgatt agccgctaca agatcgtaaa   16080
```

```
gagcgaaacc gggcggccgg agtacatcga gatcgagctg gctgattgga tgtaccgcga   16140
gatcacagaa ggcaagaacc cggacgtgct gacggttcac cccgattact ttttgatcga   16200
tcccggcatc ggccgttttc tctaccgcct ggcacgccgc gccgcaggca aggcagaagc   16260
cagatggttg ttcaagacga tctacgaacg cagtggcagc gccggagagt tcaagaagtt   16320
ctgtttcacc gtgcgcaagc tgatcgggtc aaatgacctg ccggagtacg atttgaagga   16380
ggaggcgggg caggctggcc cgatcctagt catgcgctac cgcaacctga tcgagggcga   16440
agcatccgcc ggttcctaat gtacggagca gatgctaggg caaattgccc tagcagggga   16500
aaaaggtcga aaggtctct ttcctgtgga tagcacgtac attgggaacc caaagccgta   16560
cattgggaac cggaacccgt acattgggaa cccaaagccg tacattggga accggtcaca   16620
catgtaagtg actgatataa aagagaaaaa aggcgatttt ccgcctaaa actctttaaa   16680 acttattaaa actcttaaaa cccgcctggc ctgtgcataa ctgtctggcc agcgcacagc   16740
cgaagagctg caaaaagcgc ctacccttcg gtcgctgcgc tcctacgcc ccgccgcttc   16800 gcgtcggcct atcgcggccg ctggccgctc aaaaatggct ggcctacggc caggcaatct   16860
accagggcgc ggacaagccg cgccgtcgcc actcgaccgc cggcgctgag gtctgcctcg   16920
tgaagaaggt gttgctgact cataccaggc ctgaatcgcc ccatcatcca gccagaaagt   16980
gagggagcca cggttgatga gagctttgtt gtaggtggac cagttggtga ttttgaactt   17040
ttgctttgcc acggaacggt ctgcgttgtc gggaagatgc gtgatctgat ccttcaactc   17100
agcaaaagtt cgatttattc aacaaagccg ccgtcccgtc aagtcagcgt aatgctctgc   17160
cagtgttaca accaattaac caattctgat tagaaaaact catcgagcat caaatgaaac   17220
tgcaatttat tcatatcagg attatcaata ccatattttt gaaaagccg tttctgtaat   17280 gaaggagaaa actcaccgag gcagttccat aggatggcaa gatcctggta tcggtctgcg   17340
attccgactc gtccaacatc aatacaacct attaatttcc cctcgtcaaa aataaggtta   17400
tcaagtgaga atcaccatg agtgacgact gaatccggtg agaatggcaa aagctctgca   17460
ttaatgaatc ggccaacgcg cggggagagg cggtttgcgt attgggcgct cttccgcttc   17520
ctcgctcact gactcgctgc gctcggtcgt tcggctgcgg cgagcggtat cagctcactc   17580
aaaggcggta atacggttat ccacagaatc aggggataac gcaggaaaga acatgtgagc   17640
aaaaggccag caaaaggcca ggaaccgtaa aaaggccgcg ttgctggcgt ttttccatag   17700
gctccgcccc cctgacgagc atcacaaaaa tcgacgctca agtcagaggt ggcgaaaccc   17760
gacaggacta taaagatacc aggcgtttcc ccctggaagc tccctcgtgc gctctcctgt   17820
tccgaccctg ccgcttaccg gatacctgtc cgcctttctc ccttcgggaa gcgtggcgct   17880
ttctcatagc tcacgctgta ggtatctcag ttcggtgtag tcgttcgct ccaagctggg   17940 ctgtgtgcac gaaccccccg ttcagcccga ccgctgcgcc ttatccggta actatcgtct   18000
tgagtccaac ccggtaagac acgacttatc gccactggca gcagccactg gtaacaggat   18060
tagcagagcg aggtatgtag gcggtgctac agagttcttg aagtggtggc ctaactacgg   18120
ctacactaga agaacagtat ttggtatctg cgctctgctg aagccagtta ccttcggaaa   18180
aagagttggt agctcttgat ccggcaaaca aaccaccgct ggtagcggtg tttttttgt   18240 ttgcaagcag cagattacgc gcagaaaaaa aggatctcaa gaagatcctt tgatcttttc   18300 tacgggtct gacgctcagt ggaacgaaaa ctcacgttaa gggattttgg tcatgagatt   18360
atcaaaaagg atcttcacct agatcctttt gatccggaat ta                     18402
```

```
<210> SEQ ID NO 76
<211> LENGTH: 14
<212> TYPE: PRT
<213> ORGANISM: Triticum aestivum

<400> SEQUENCE: 76

Arg Ala Gly Arg Ala Ala Ala Pro Gly Gly Ala Gln Gly Ala
1               5                   10

<210> SEQ ID NO 77
<211> LENGTH: 47
<212> TYPE: PRT
<213> ORGANISM: Triticum aestivum

<400> SEQUENCE: 77

Val Ala Arg Asp Leu Pro Gly Ser Leu Pro Phe Arg Phe Val Leu Phe
1               5                   10                  15

Ser Val Phe Trp Ser Asp Leu Leu Val Thr Cys Ser Thr Glu Cys Arg
            20                  25                  30

Gly Glu Pro Gly Gly Arg Arg Pro Gln Gly Gly Leu Lys Gly Gln
        35                  40                  45

<210> SEQ ID NO 78
<211> LENGTH: 44
<212> TYPE: PRT
<213> ORGANISM: Triticum aestivum

<400> SEQUENCE: 78

Gly Thr Phe Pro Gly Arg Phe Leu Phe Val Ser Ser Cys Phe Leu Phe
1               5                   10                  15

Phe Gly Leu Thr Cys Ser Ser Pro Val Arg Arg Asn Ala Glu Ala Ser
            20                  25                  30

Arg Ala Gly Gly Gly Pro Arg Gly Gly Ser Arg Gly
        35                  40

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79
cgactcgcct cgcgctagta                                              20
```